(12) United States Patent
Borza et al.

(10) Patent No.: US 10,960,007 B2
(45) Date of Patent: Mar. 30, 2021

(54) PHARMACOLOGICALLY ACTIVE ARYL-SUBSTITUTED PYRAZOLO[1,5-A]PYRIMIDINE DERIVATIVES

(71) Applicant: RICHTER GEDEON NYRT., Budapest (HU)

(72) Inventors: István Borza, Budapest (HU); Viktor Román, Érd (HU); János Éles, Budapest (HU); Zsuzsa Hadady, Debrecen (HU); József Huszár, Budapest (HU)

(73) Assignee: RICHTER GEDEON NYRT., Budapest (HU)

( * ) Notice: Subject to any disclaimer, the term of this patent is extended or adjusted under 35 U.S.C. 154(b) by 0 days.

(21) Appl. No.: 16/493,018

(22) PCT Filed: Mar. 12, 2018

(86) PCT No.: PCT/IB2018/051598
§ 371 (c)(1),
(2) Date: Sep. 11, 2019

(87) PCT Pub. No.: WO2018/167629
PCT Pub. Date: Sep. 20, 2018

(65) Prior Publication Data
US 2020/0061068 A1  Feb. 27, 2020

(30) Foreign Application Priority Data
Mar. 13, 2017  (HU) .................................. P1700107

(51) Int. Cl.
*A61K 31/519* (2006.01)
*C07D 487/04* (2006.01)

(52) U.S. Cl.
CPC .......... *A61K 31/519* (2013.01); *C07D 487/04* (2013.01)

(58) Field of Classification Search
CPC .................................................. C07D 487/04
See application file for complete search history.

(56) References Cited

U.S. PATENT DOCUMENTS

| | | | |
|---|---|---|---|
| 8,461,163 B2 * | 6/2013 | Chang | A61P 7/00 514/259.3 |
| 9,828,381 B2 * | 11/2017 | Faghih | C07D 519/00 |
| 2016/0304527 A1 | 10/2016 | Faghih et al. | |

FOREIGN PATENT DOCUMENTS

WO  WO 2018/167630  9/2018

OTHER PUBLICATIONS

Bettler, B., et al., "Molecular Structure and Physiological Functions of $GABA_B$ Receptors," *Physiol. Rev.* 84:835-867, 2004, American Physiological Society, United States.
Biermann, B., et al., "The Sushi Domains of $GABA_B$ Receptors Function as Axonal Targeting Signals," *J. Neurosci.* 30(4):1385-1394, 2010, Society for Neuroscience, United States.

Binet, V., et al., "The Heptahelical Domain of $GABA_{B2}$ Is Activated Directly by CGP7930, a Positive Allosteric Modulator of the $GABA_B$ Receptor," *J. Biol. Chem.* 279(28):29085-29091, 2004, The American Society for Biochemistry and Molecular Biology, Inc., United States.
Bowery, N.G., et al., "$GABA_A$ and $GABA_B$ Receptor Site Distribution in the Rat Central Nervous System," *Neuroscience* 20(2):365-383, 1987, Pergamon Journals Ltd., England.
Breslow, M.F., et al., "Role of γ-Aminobutyric Acid in Antipanic Drug Efficacy," *Am. J. Psychiatry* 146(3):353-356, 1989, American Psychiatric Association, United States.
Chalifoux, J.R., et al., "$GABA_B$ receptor modulation of synaptic function," *Curr. Opin. Neurobiology* 21:339-344, 2011, Elsevier, United States.
Conn, P.J., et al., "Allosteric modulators of GPCRs: a novel approach for the treatment of CNS disorders," *Nat. Reviews* 8:41-54, 2009, Macmillan Publishers Limited, Germany.
Cryan, J.F., et al., "Behavioral Characterization of the Novel $GABA_B$ Receptor-Positive Modulator GS39783 (N,N'-Dicyclopentyl-2-methylsulfanyl-5-nitro-pyrimidine-4,6-diamine): Anxiolytic-Like Activity without Side Effects Associated with Baclofen or Benzodiazepines," *J. Pharmacol. Exp. Therap.* 310(3):952-963, 2004, The American Society for Pharmacology and Experimental Therapeutics, United States.
Drake, R.G., et al., "Baclofen Treatment for Chronic Posttraumatic Stress Disorder," *Annals of Pharmacother.* 37:1177-1181, 2003, Harvey Whitney Books Company, United States.

(Continued)

*Primary Examiner* — Golam M Shameem
(74) *Attorney, Agent, or Firm* — Sterne, Kessler, Goldstein & Fox P.L.L.C.

(57) ABSTRACT

The present invention relates to new pyrazolo[1,5-a]pyrimidine derivatives of formula (I) or pharmaceutically acceptable salts, biologically active metabolites, pro-drugs, racemates, enantiomers, diastereomers, solvates and hydrates thereof that serve as $GABA_B$ receptor positive allosteric modulators. The invention also relates to the process for producing such compounds. The invention further relates to pharmaceutical compositions comprising such compounds optionally in combination with two or more different therapeutic agents and the use of such compounds in methods for treating diseases and conditions mediated and modulated by the $GABA_B$ receptor positive allosteric mechanism. The invention also provides a method for manufacture of medicaments useful in the treatment of such disorders.

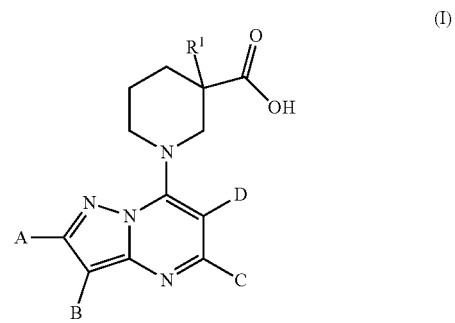

16 Claims, No Drawings

(56) References Cited

OTHER PUBLICATIONS

Dupuis, D.S., et al., "Point Mutations in the Transmembrane Region of $GABA_{B2}$ Facilitate Activation by the Positive Modulator N,N'-Dicyclopentyl-2-methylsulfanyl-5-nitro-pyrimidine-4,6-diamine (GS39783) in the Absence of the $GABA_{B2}$ Subunit," *Mol. Pharmacol.* 70(6):2027-2036, 2006, American Society for Pharmacology and Experimental Therapeutics, United States.

Gassmann, M., et al., "Redistribution of $GABA_{B(1)}$Protein and Atypical $GABA_B$ Responses in $GABA_{B(2)}$-Deficient Mice," *J. Neurosci.* 24(27):6086-6097, 2004, Society for Neuroscience, United States.

Gjoni, T., et al., "Receptor activation involving positive allosteric modulation, unlike full agonism, does not result in $GABA_B$ receptor desensitization," *Neuropharmacol.* 55:1293-1299, 2008, Elsevier, United States.

Hill, D.R. et al "$^3$H-baclofen and $^3$H-GABA bind to bicuculline-insensitive $GABA_B$ sites in rat brain," *Nature* 290:149-152, 1981, Macmillan Journals Ltd., Germany.

Keegan, B.M.T., et al., "Chronic baclofen desensitizes $GABA_B$-mediated G-protein activation and stimulates phosphorylation of kinases in mesocorticolimbic rat brain," *Neuropharmacol.* 95:492-502, 2015, Elsevier, United States.

Leggio, L., et al., "Effectiveness and Safety of Baclofen in the Treatment Dependent Patients," *CNS & Neurol. Disord —Drug Targ.* 9:33-44, 2010, Bentham Science Publishers Ltd., United States.

Mombereau, C., et al., "Genetic and Pharmacological Evidence of a Role for $GABA_B$ Receptors in the Modulation of Anxiety- and Antidepressant-Like Behavior," *Neuropsychopharmacol.* 29:1050-1062, 2004, Nature Publishing Group, United States.

Mombereau, C., et al., "Altered response to benzodiazepine anxiolytics in mice lacking $GABA_{B(1)}$receptors," *Eur. J. Pharmacol.* 496:119-120, 2004, Elsevier, United States.

Mombereau, C., et al., "Altered anxiety and depression-related behavior in mice lacking $GABA_{B(2)}$receptor subunits," *NeuroReport* 16:307-310, 2005, Lippincott Williams & Wilkins, United States.

Perdona, E., et al., "In vitro and in vivo characterization of the novel $GABA_B$ receptor positive allosteric modulator, 2-{1-[2-(4-chlorophenyl)-5-methylpyrozolo[1,5- a]pyrimidin-7-yl]-2-piperidinyl}ethanol (CMPPE)" *Neuropharmacol.* 61:957-966, 2011, Elsevier, United States.

Ross, J.C., et al., "Acute Intrathecal Baclofen Withdrawal: A Brief Review of Treatment Options," *Neurocrit. Care* 14:103-108, 2011, Neurocritical Care Society, United States.

Schuler, V.S., et al., "Epilepsy, Hyperalgesia, Impaired Memory, and Loss of Pre-and Postsynaptic $GABA_B$ Responses in Mice Lacking $GABA_{B(1)}$," *Neuron* 31:47-58, 2001, Cell Press, United States.

Ulrich, D. et al., "$GABA_B$ receptors: synaptic functions and mechanisms of diversity" *Curr. Opin. Neurobiol.* 17:298-303, 2007, Elsevier, United States.

Vacher, C.-M., et al., "$GABA_B$ Receptors as Potential Therapeutic Agents," *Curr. Drug Targets—CNS& Neurol. Disord.* 2:251-263, 2003, Bentham Science Publishers Ltd., United States.

Vigot, R., et al., "Differential Compartmentalization and Distinct Functions of $GABA_B$ Receptor Variants," *Neuron* 50:589-601, 2006, Elsevier, United States.

Wang, L., el al., "Allosteric Modulators of G Protein-Coupled Receptors: Future Therapeutics for Complex Physiological Disorders," *J. Pharmacol. Exper. Therap.* 331(2):340-348, United States (2009).

\* cited by examiner

PHARMACOLOGICALLY ACTIVE ARYL-SUBSTITUTED PYRAZOLO[1,5-A]PYRIMIDINE DERIVATIVES

FIELD OF THE INVENTION

The present invention relates to new pyrazolo[1,5-a] pyrimidine derivatives of formula (I) or pharmaceutically acceptable salts, biologically active metabolites, pro-drugs, racemates, enantiomers, diastereomers, solvates and hydrates thereof that serve as $GABA_B$ receptor positive allosteric modulators. The invention also relates to the process for producing such compounds. The invention further relates to pharmaceutical compositions comprising such compounds optionally in combination with two or more different therapeutic agents and the use of such compounds in methods for treating diseases and conditions mediated and modulated by the $GABA_B$ receptor positive allosteric mechanism. The invention also provides a method for manufacture of medicaments useful in the treatment of such disorders.

BACKGROUND OF THE INVENTION

Gamma-aminobutyric acid (GABA) is the main inhibitory neurotransmitter in the central nervous system and plays a key role in modulating neuronal activity. It exerts its action via three receptor systems, the related ionotropic $GABA_A$ and $GABA_C$ receptors, and the distinct metabotropic $GABA_B$ receptors (Hill and Bowery, Nature 1981, 290, 149-152). The latter $GABA_B$ receptors are widespreadly distributed within the mammalian central nervous system with various expression levels in different brain regions (Bovery et al, Neuroscience 1987, 20, 365-385). $GABA_B$ receptors can be found both pre- and postsynaptically and play an important role in the fine-tuning of neurotransmission. Most $GABA_B$ receptors cluster around excitatory synapses, either at the edge of the presynaptic terminal or on dendritic spines opposite to glutamatergic boutons (Ulrich and Bettler, Curr. Opin. Neurobiol. 2007, 17, 298-303).

$GABA_B$ receptors belong to the Family 3 (C) of G-protein coupled receptors (GPCRs) together with metabotropic glutamate receptors (mGluRs), calcium-sensing receptors, taste receptors and a number of orphan receptors, showing highest, approximately 30% homology to mGluRs (Bettler et al, Physiol. Rev. 2004, 84, 835-867). $GABA_B$ receptors are heterodimers consisting of two similar, yet different subunits, B1 and B2. The B1 subunit has multiple splice variants with only two (B1a and B1b) having clear physiological significance. These isoforms differ only in their extracellular domain containing two Sushi motifs that regulate the subcellular localization of the receptor (Vigot et al, Neuron 2006, 50, 589-601; Biermann et al, J. Neurosci. 2010, 30, 1385-1394). The B1 subunit binds the endogenous neurotransmitter ligand GABA as well as other orthosteric agonists (such as baclofen, SKF97541) and antagonists (such as phaclofen, saclofen). The B2 subunit is responsible for G-protein activation-mediated intracellular signal transduction and is believed to bind allosteric modulators (Binet et al, J. Biol. Chem. 2004, 279, 29085-29091; Dupuis et al, Mol. Pharmacol. 2006, 70, 2027-2036). The site of action for the Novartis $GABA_B$ positive allosteric modulator compounds CGP7930 and GS39783 is the heptahelical transmembrane domain of the B2 subunit; the exact binding site for other, unrelated positive allosteric modulator chemotypes is not known.

The main synaptic effects of $GABA_B$ receptors are the presynaptic blockade of neurotransmitter release (GABA as well as glutamate) and postsynaptic hyperpolarization (Gassmann and Bettler, in Handbook of Contemporary Neuropharmacology 2007). These effects are the result of inhibition of presynaptic calcium influx and stimulation of postsynaptic inwardly rectifying potassium (GIRK) channels, respectively. Ion channel functions are mediated in a membrane-delimited manner through the activation of $\beta\gamma$ subunits of $G_i/G_o$ proteins. In addition to these, $GABA_B$ receptors also signal via the $\alpha$ subunit of the same G-proteins that inhibits adenylate cyclase and retards the recruitment of synaptic vesicles (Chalifoux and Carter, Curr. Opin. Neurobiol. 2011, 21, 339-442). Beside these fast cellular events, $GABA_B$ receptors also regulate cytoplasmic kinases including mitogen-acivated protein kinase and thereby influence synaptic plasticity on the longer-term.

In order to better understand the physiological significance of $GABA_B$ receptors at the behavioral level, knockout mice have been generated with mutations selectively in the B1, B1a, Bib and the B2 subunits. Mice without B1 subunits displayed increased anxiety in explorative-like situations (light-dark box, staircase assays), increased panic, spontaneous seizures, hyperalgesia, hyperlocomotion, and memory impairment (Schuler et al, Neuron 2001, 31, 47-58). Mice that do not express GABAB2 subunits behave similarly to B1 subunit knockouts; these animals are overanxious, show spontaneous seizure activity, hyperalgesia, hyperlocomotion, and memory impairment (Mombereau et al, Eur. J. Pharmacol. 2004, 497, 119-120; Mombereau et al, Neuroreport 2005, 16, 307-310; Gassmann et al, J. Neurosci. 2004, 24, 6086-6097). Based on the above, the $GABA_B$ receptor system seems to play a general role in the regulation of neuronal excitability with consequences on various aspects of overt behavior.

The only approved and commercialized selective $GABA_B$ receptor ligand is the orthosteric agonist racemic baclofen. Baclofen was approved as a centrally acting muscle relaxant used to reduce spasticity associated with cerebral palsy, multiple sclerosis, and spinal cord injuries. Beside these applications, baclofen may have potential therapeutic benefits in treating conditions including asthma, pain, obesity, binge eating, drug and alcohol abuse, anxiety, posttraumatic stress disorder, cough, inflammation, gastroeasophageal reflux and urinary incontinence (eg., Breslow et al, Am. J. Psychiatry 1989, 146, 353-356; Drake et al, Ann. Pharmacother. 2003, 37, 1177-1181; Leggio et al, CNS Neurol. Disord. Drug Targets 2010, 9, 33-44). Although baclofen has beneficial potential in a number of therapeutic indications, unfortunately it also has a range of unwanted properties including poor blood-brain-barrier penetration, narrow therapeutic window, receptor desensitization, development of tolerance against the main effects, and withdrawal upon termination of use (Vacher and Bettler, Curr. Drug Targets CNS Neurol. Disord. 2003, 2, 248-259; Ross et al, Neurocrit. Care 2011, 14, 103-108; Keegan et al, Neuropharmacology 2015, 95, 492-502).

Allosteric modulation is an alternative way to selectively stimulate GPCRs without the unwanted properties of orthosteric ligands (Conn et al, Nat Rev 2009, 8, 41-54; Wang et al, J. Pharmacol. Exp. Ther. 2009, 331, 340-348). Allosteric modulators bind to the receptors at sites that are different from the binding site of the endogenous (orthosteric) ligands and are effective predominantly if an agonist is also bound to the receptor. This has consequences on the temporal and spacial pattern of efficacy which in turn affects the behavioral and adaptive responses the organism gives to allosteric stimulation. In contrast to orthosteric agonism, allosteric modulation of targets is expected to show less side effects, desensitization and development of tolerance. Indeed, it has been shown for the $GABA_B$ receptor positive allosteric modulator GS39783 in preclinical models, that this compound can have a favourable side effect profile (Cryan et al, *J. Pharmacol. Exp. Ther.* 2004, 310, 952-963), desensitization of the receptor can be prevented (Gjoni and Urwyler, *Neuropharmacology* 2008, 55:1293-1299) and tolerance may not develop upon chronic administration (Mombereau et al, *Neuropsychopharmacology* 2004, 29, 1050-1062). These results suggest that positive allosteric modulators of the $GABA_B$ receptor may be useful novel chemical entities without the unwanted properties of the orthosteric ligands such as baclofen.

A representative positive allosteric compound (2-{1-[2-(4-chlorophenyl)-5-methylpyrazolo[1,5-a]pyrimidin-7-yl]-2-piperidinyl}ethanol, CMPPE) belonging to a novel chemotype has been reported by Perdona and co-workers (Perdona et al, *Neuropharmacology* 2011, 61, 957-966). CMPPE positively modulated the $EC_{20}$ GABA-evoked in vitro [$^{35}$S]GTPγS binding signal with an $EC_{50}$ value of 2.57 µM (in our in vitro [$^{35}$S]GTPγS test system CMPPE showed an $EC_{50}$ value of611 nM). In Perdona et al., the compound showed mild efficacy in a food consumption test in rats reaching significance only at high doses (30 and 100 mg/kg). In a functional in vivo assay (potentiation of baclofen-induced muscle relaxation in mice) CMPPE showed weak activity with an $ED_{50}$ value of 53.8 mg/kg. Modest in vitro activity of CMPPE translates into weak in vivo activity. Furthermore, the compound has poor metabolic stability in liver microsomal systems ($Cl_{int}$ 0.19±0.02, 0.31±0.07, 1.18±0.4 mL/min/g liver in human, rat and mouse conventional liver microsomes, respectively). In summary, CMPPE is a singleton and represents a chemotype that needs extensive optimization before it could be utilized to treat human diseases or disorders associated with the $GABA_B$ receptor system.

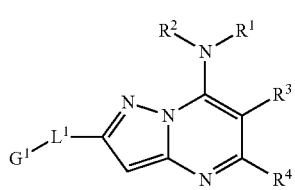

CMPPE

A recent patent application by Faghih et al. (US 2016/0304527 A1) describes pyrazolo-pyrimidines with in vitro positive allosteric activity at the $GABA_B$ receptors measured by [$^{35}$S]GTPγS binding.

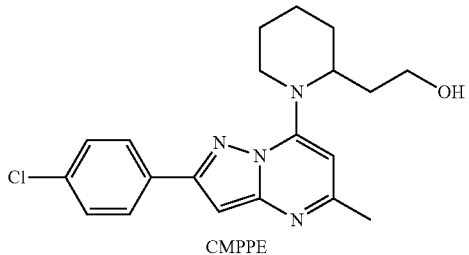 [SMILES: Cc1cc(N2CCCCC2CCO)n2nc(-c3ccc(Cl)cc3)cc2n1]

Example 1-1

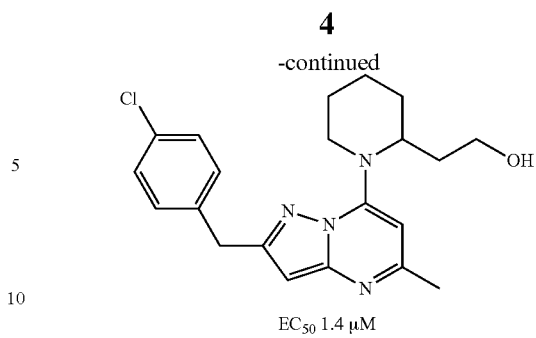

$EC_{50}$ 1.4 µM

The invention of Faghih et al. describes that the incorporation of linkers comprising three or four carbon atoms (L1) increases in vitro potency. Most of the examplified aryl-substituted compounds with linkers comprising one or two carbon atoms show only micro or submicromolar binding potency (Example 1-1). However, only the examplified compounds which contain a linker comprising three or four carbon atoms (Example 3-1; Example 5-1) reach nanomolar potency. Unexpectedly, we found in the present invention that compounds without any linker show low nano or subnanomolar potency.

Example 3-1

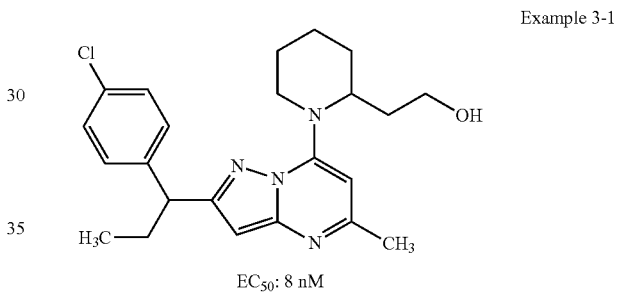

$EC_{50}$: 8 nM

Exampe 5-1

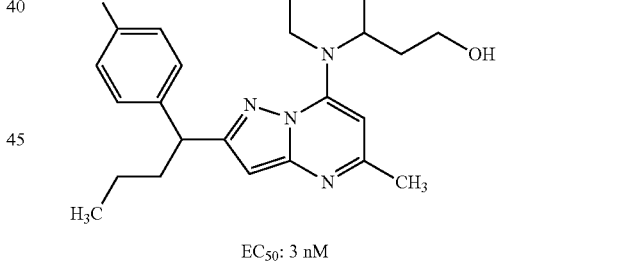

$EC_{50}$: 3 nM

Examplified compounds containing azetidine carboxylic acid (Example 8-10) or nipecotic acid amide (Example 1-19) moieties in Faghih et al. show only high micromolar potency. Unexpectedly, we found in the present invention that compounds bearing the simple nipecotic acid moiety show nano or subnanomolar potency. These compounds despite of possessing acidic nipecotic acid moiety are metabolically stable and unexpectedly penetrate into the brain (principles of brain penetration of drug molecules are summarized in: Kerns et al. Drug-like Properties: Concepts, Structure Design and Methods Chapter: Blood-Brain Barrier pages 122-136 "FIG. 10.12: Acids poorly penetrate the BBB (Blood Brain Barrier) (CNS—)").

The above described in vitro advantages are further strengthened by the unexpected finding that selected compounds of the present invention were of great behavioral benefit in the prenatal valproate disease model that recapitulates the core symptoms of autism spectrum disorder. The inventors therefore showed that this compound has therapeutic potential for the treatment of core symptoms of autism spectrum disorder in humans.

SUMMARY OF THE INVENTION

We have identified a class of pyrazolo[1,5-a]pyrimidine derivatives which have high affinity for $GABA_B$ receptors providing unique role in the treatment of psychiatric, neurodevelopmental, neurological and other central nervous system disorders as well as peripheral conditions where modulation of the $GABA_B$ receptor hastherapeutic benefit, in particular the compounds of formula (I) may be of therapeutic potential for the core symptoms of ASD. The present invention relates to compounds being $GABA_B$ receptor positive allosteric modulators and the synthesis thereof. Compounds of the present invention are useful for the treatment of the above disorders.

The present invention relates to the pyrazolo[1,5-a]pyrimidine derivatives of formula (I)

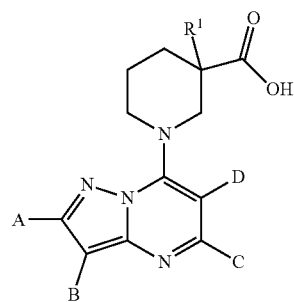

(I)

A is an optionally substituted phenyl or pyridyl group;
B is hydrogen or halogen atom, methyl, cyano group;
C is $C_{1-6}$alkyl;
D is $C_{1-6}$alkyl optionally substituted by a halogen atom or halogen atoms, $C_{3-5}$ cycloalkyl; $C_{3-5}$cycloalkylC$_{1-6}$alkyl, dialkylamino, $C_{1-6}$alkoxy, $C_{1-6}$alkoxyC$_{1-6}$alkyl, $C_{1-6}$alkylthio group, tetrahydrofuranyl, tetrahydrofuranylC$_{1-6}$alkyl, tetrahydropyranyl, tetrahydropyranylC$_{1-6}$alkyl; or C and D together form an unsubstituted or substituted by one or more $C_{1-3}$alkyl, $C_{1-3}$alkoxy, haloC$_{1-3}$alkyl, $C_{1-3}$alkylcarbonyl 3 to 7-membered saturated ring, wherein the members of the ring are selected from the group consisting of carbon, nitrogen, oxygen, and sulphur; $R^1$ is hydrogen, halogen atom or $C_{1-6}$alkyl, hydroxyl, $C_{1-6}$alkoxy, $C_{1-6}$alkoxyC$_{1-6}$alkyl, haloC$_{1-6}$alkyl, amino group; or pharmaceutically acceptable salts, biologically active metabolites, pro-drugs, racemates, enantiomers, diastereomers, solvates and hydrates thereof. The invention also relates to the pharmaceutical compositions containing the compounds of formula (I) or pharmaceutically acceptable salts, biologically active metabolites, pro-drugs, racemates, enantiomers, diastereomers, solvates and hydrates thereof as active ingredient.

Furthermore the present invention relates to the synthesis of the compounds of formula (I) and optical antipodes or racemates and/or salts thereof, the pharmaceutical compositions comprising thereof and the manufacture of medicaments containing these compounds, as well as the methods of treatment with these compounds, which means administering to a mammal to be treated—including human—suffering from disorders psychiatric, neurodevelopmental, neurological and other central nervous system disorders as well as peripheral conditions where modulation of the $GABA_B$ receptor might have therapeutic benefit, effective amount of compounds of formula (I) and optical antipodes or racemates and/or salts thereof of the present invention as such or as medicament.

DETAILED DESCRIPTION OF THE INVENTION

The present invention relates to pyrazolo[1,5-a]pyrimidine derivatives of formula (I)

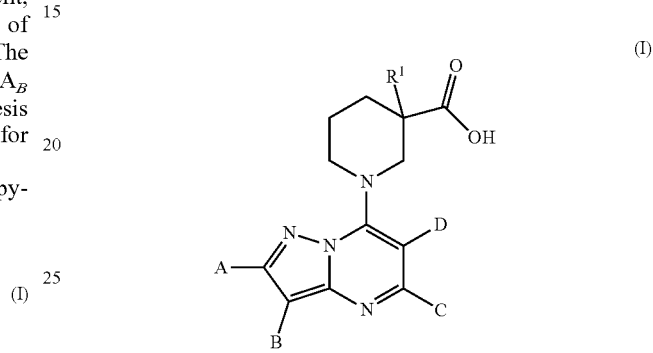

(I)

A is an optionally substituted phenyl or pyridyl group;
B is hydrogen or halogen atom, methyl, cyano group;
C is $C_{1-6}$alkyl;
D is $C_{1-6}$alkyl optionally substituted by a halogen atom or halogen atoms, $C_{3-5}$ cycloalkyl; $C_{3-5}$ cycloalkylC$_{1-6}$alkyl, dialkylamino, $C_{1-6}$alkoxy, $C_{1-6}$alkoxyC$_{1-6}$alkyl, $C_{1-6}$alkylthio group, tetrahydrofuranyl, tetrahydrofuranylC$_{1-6}$alkyl, tetrahydropyranyl, tetrahydropyranylC$_{1-6}$alkyl; or C and D together form an unsubstituted or substituted by one or more $C_{1-3}$alkyl, $C_{1-3}$alkoxy, haloC$_{1-3}$alkyl, $C_{1-3}$alkylcarbonyl 3 to 7-membered saturated ring, wherein the members of the ring are selected from the group consisting of carbon, nitrogen, oxygen, and sulphur; $R^1$ is hydrogen, halogen atom or $C_{1-6}$alkyl, hydroxyl, $C_{1-6}$alkoxy, $C_{1-6}$alkoxyC$_{1-6}$alkyl, haloC$_{1-6}$alkyl, amino group;
and optical antipodes or racemates and/or salts thereof.

When the meaning of A is an optionally substituted phenyl group the term "optionally substituted" means that it may be substituted by one, two or three substituent selected from halogen atom, $C_1$-$C_6$-alkoxy group, $C_1$-$C_6$-alkyl, —CN or —CF$_3$ group.

When the meaning of A is optionally substituted pyridyl group the term "optionally substituted" means that it may be substituted by one or two substituent selected from halogen atom, $C_1$-$C_6$-alkyl, —CN or —CF$_3$ group.

The term "halogen" or "halo" as used herein alone or as a part of another group refers to chlorine, bromine, fluorine and iodine.

The term "$C_1$-$C_6$ alkyl" as used herein refers to branched or straight chain alkyl groups comprising one to sixcarbon atoms, including methyl, ethyl, propyl, normal- and isopropyl and different butyl groups.

The term "$C_3$-$C_5$ cycloalkyl" as used herein refers to carbocyclic groups of 3 to 5 carbons, respectively; for example, cyclopropyl, cyclobutyl, and cyclopentyl.

The term "$C_1$-$C_6$ alkoxy" as used herein refers to branched or straight chain alkyl groups comprising one to six carbon atoms bonded through an oxygen atom, including but not limited to, methoxy, ethoxy, n-propoxy, i-propoxy, and t-butoxy.

The term "$C_{1-6}$alkylthio" as used herein refers to branched or straight chain alkyl groups comprising one to six carbon atoms bonded through a sulfur atom, including but not limited to, methylthio, ethylthio, n-propylthio, i-propylthio, and t-butylthio.

The term "mammal" as used herein refers to any members of the class "Mammalia" including, but not limited to human.

The term "salt" means nontoxic base addition salts of the compounds of the invention which are generally prepared by reacting the acid with a suitable organic or inorganic base.

Included within the scope of the present invention are all stereoisomers, geometric isomers and tautomeric forms of the compounds of formula (I), including compounds exhibiting more than one type of isomerism and mixtures of one or more thereof.

Conventional techniques for the preparation/isolation of individual enantiomers include chiral synthesis from the suitable optically pure precursor or resolution of the racemate (or racemate of a salt or derivative) using, for example chiral high pressure liquid chromatography (HPLC).

The term "pharmaceutically acceptable" describes an ingredient that is useful in preparing a pharmaceutical composition and is generally safe, non-toxic and neither biologically nor otherwise undesirable, and includes those acceptable for veterinary use as well as human pharmaceutical use.

The term "pharmaceutical composition" refers to a mixture of a compound of the invention with other chemical components, such as pharmaceutically acceptable excipients e.g. diluents or carriers. The pharmaceutical composition facilitates administration of the compound to the subject.

The term "excipient" defines a chemical compound that facilitates the incorporation of a compound into cells or tissues.

As used herein, the term "treatment" means using an effective therapy to reduce, alleviate or eliminate the symptoms associated with diseases and conditions mediated and modulated by the $GABA_B$ receptor positive allosteric mechanism.

As a further aspect of the present invention there is provided the synthesis of compounds of formula (I).

Compounds in accordance with the present invention were synthesized in line with the synthetic routes and schemes described below.

Accordingly, the compounds of formula (I) of the invention can be synthesized by one of the following methods:

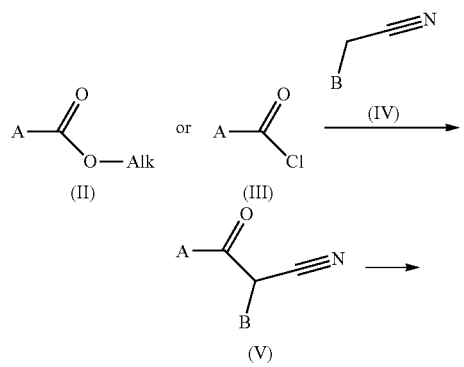

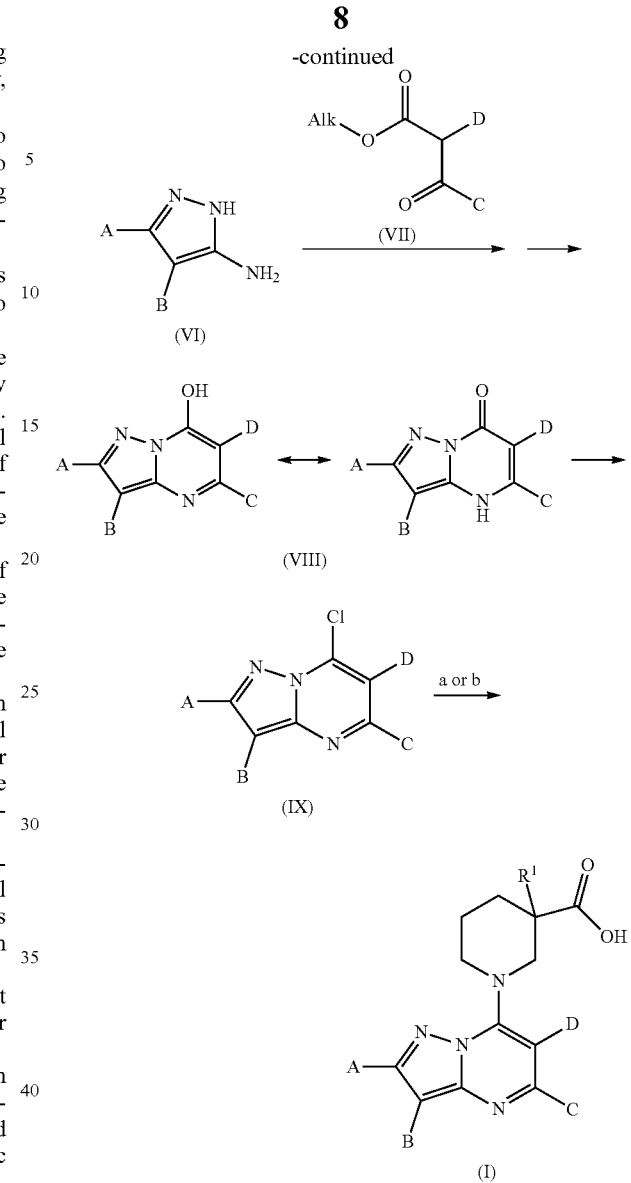

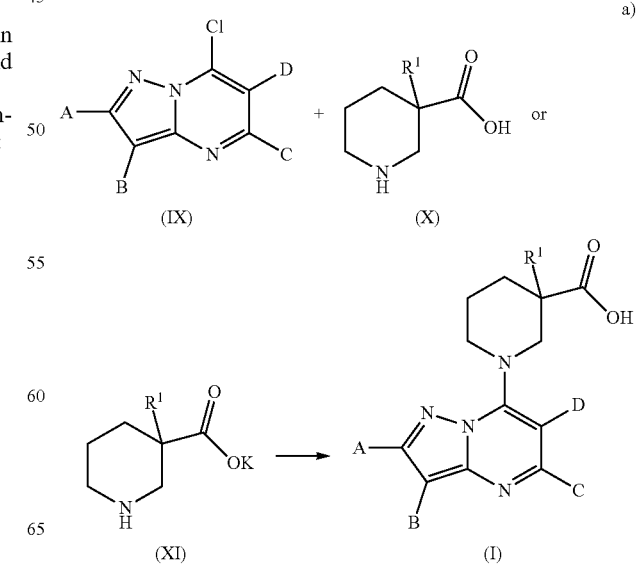

b)

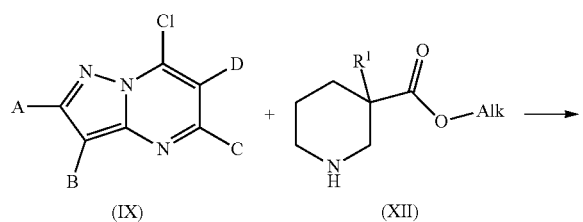

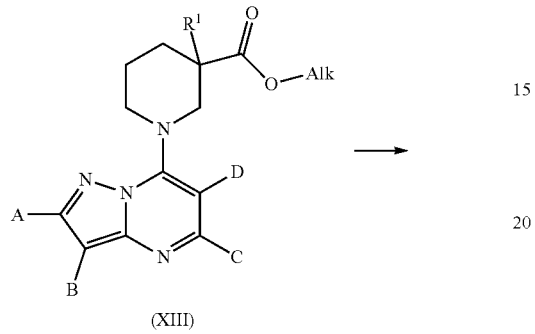

(XIII)

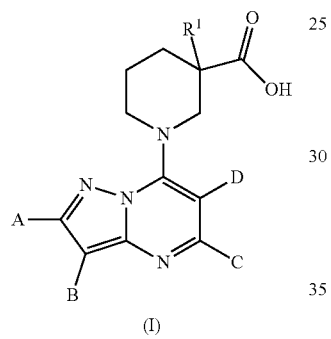

(I)

Reacting a carboxylic acid ester derivative of formula (II) or carboxylic acid chloride derivative of formula (III)

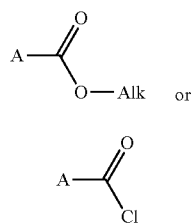

wherein the meaning of A is described above for compound of Formula (I)—with an acetonitrile derivative of formula (IV)

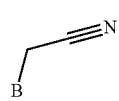

wherein the meaning of B is described above for compound of Formula (I)—then the so obtained acylacetonitrile derivative of formula (V)

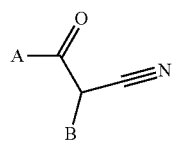

wherein the meaning of A and B is as described above for the formula (I)—is reacted with hydrazine hydrate to provide the 1H-pyrazolo-5-amine derivative of formula (VI)

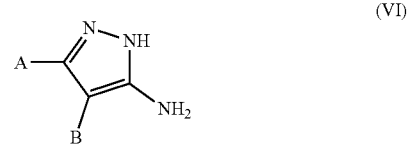

wherein the meaning of A and B is as described above for the formula (I)—is reacted with acetoacetic ester derivative of formula (VII)

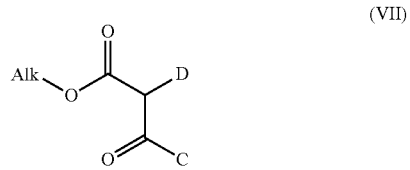

wherein the meaning of C and D is as described above for the formula (I)—then the so obtained pyrazolo[1,5-a]pyrimidine derivative of formula (VIII)

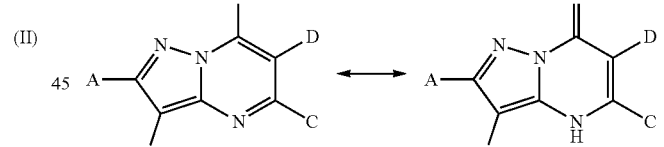

wherein the meaning of A, B, C, and D is as described above for the formula (I)—the latter is chlorinated to furnish a chloro derivative of formula (IX)

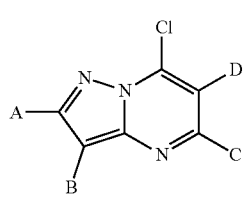

wherein the meaning of A, B, C, and D is as described above for the formula (I)—the latter is reacted with
a) a nipecotic acid derivative of formula (X) or its alkali salt of formula (XI)

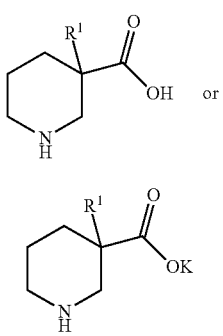

(X)

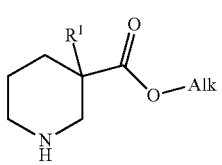

(XI)

wherein the meaning of R1 is as described above for the formula (I)—and the obtained pyrazolo[1,5-a]pyrimidine derivative of formula (I) and optical antipodes or racemates and/or salts thereof in given case can be transformed into an other compound of formula (I) and optical antipodes or racemates and/or salts thereof by introducing new substituents and/or modifying or removing the existing ones, b) or a nipecotic acid ester derivative of formula (XII)

(XII)

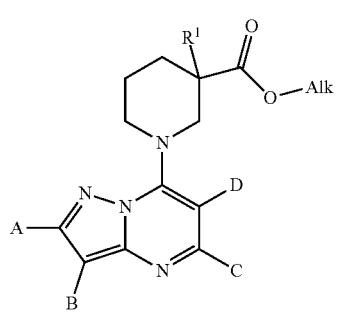

wherein the meaning of $R^1$ is as described above for the formula (I)—to provide the ester derivative of formula (XIII)

(XIII)

wherein the meaning of $R^1$, A, B, C, and D is as described above for the formula (I)—finally the latter is saponified with a strongly base or acid—and the obtained pyrazolo[1,5-a]pyrimidine derivative of formula (I) and optical antipodes or racemates and/or salts thereof optionally can be transformed into an other compound of formula (I) and optical antipodes or racemates and/or salts thereof by introducing new substituents and/or modifying or removing the existing ones.

The synthesis of acylacetonitrile derivative (V) can be carried out by different routes:

a) The reaction of a carboxylic acid ester derivative of formula (II) with an acetonitrile derivative of formula (IV) is preferably carried out in a suitable solvent, e.g. acetonitrile, preferably in the presence of a strong base e.g. sodium methylate. The reaction is preferably carried out at boiling point of the solvent. The necessary reaction time is 1-6 h. The reactions are followed by thin layer chromatography. The reaction is quenched by addition of water, acidified with hydrochloric acid (~pH 2-3). The product is isolated by filtration or extraction with a suitable organic solvent.

b) The reaction of an carboxylic acid chloride derivative of formula (III) with an acetonitrile derivative of formula (IV) is preferably carried out in a suitable solvent, e.g. tetrahydrofuran, preferably in the presence of a strong base e.g. n-butyllithium, lithium bis(trimethylsilyl)amide. The reaction carried out at a temperature in the range of $-78°$ C. to room temperature. The necessary reaction time is 1-16 h. The reactions are followed by thin layer chromatography. The reaction is quenched by addition of water and hydrochloric acid (~pH 2-3) or saturated ammonium chloride solution. The product is isolated by extraction with a proper organic solvent or by filtration, after removing the organic solvent.

The cyclocondensation reaction of the acyl nitrile derivatives of formula (V) with hydrazine hydrate to pyrazole derivatives of formula (VI) is preferably carried out in a suitable solvent, e.g. ethanol. The reaction is preferably carried out at boiling point of the solvent. The necessary reaction time is 1-6 h. The reactions are followed by thin layer chromatography. The work-up of the reaction mixture can be carried out by the following methods:

a) The reaction mixture is diluted with water and the product is isolated by filtration or extraction with a suitable organic solvent and in given case purified by crystallization or column chromatography.

b) The reaction mixture is evaporated in vacuo and the crude product is used in the next step without further purification.

The cyclocondensation reaction of the 1H-pyrazol-5-amine derivative of formula (VI) with an acetoacetic ester derivative of formula (VII) is preferably carried out in a suitable solvent, e.g. toluene, by the addition of catalytic amount of p-toluenesulfonic acid, using a Dean-Stark water separator. The reaction is preferably carried out at boiling point of the solvent. The necessary reaction time is 1-16 h. The reactions are followed by thin layer chromatography. The product is isolated by filtration.

Chlorination of the pyrazolo[1,5-a]pyrimidine derivative of formula (VIII) can be carried out in a suitable solvent, e.g. toluene using a proper chlorinating agent, e.g. phosphorus oxychloride by the addition of triethylamine or N,N-diisopropylethylamine. The reaction is preferably carried out at boiling point of the solvent. The necessary reaction time is 24-48 h. The reactions are followed by thin layer chromatography. The reaction mixture is poured into sodium hydrogen carbonate solution and crushed ice. The decomposed reaction mixture is filtered and the product is isolated from the filtrate by extraction with a suitable organic solvent and in optionally purified by crystallization or column chromatography. The column chromatography is carried out on normal phase using Kiesel gel 60 as adsorbent and different solvent systems, e.g. n-hexane/ethyl acetate, toluene/methanol, chloroform/methanol or toluene/acetone, as eluents.

N-arylation reaction of the nipecotic acid derivative of formula (X) or (XII) with the chloro derivative of formula (IX) carried out in a suitable solvent, e.g. dimethylformamide, dimethylsulfoxide, N-methyl-pyrrolidine. The reaction is preferably carried out between $80°$ C. and $140°$ C. A suitable amine of formula (X) or (XII) is added as base or as a salt formed with inorganic acid to the so obtained solution in the presence of a base, for example cesium carbonate or N,N-diisopropylethylamine, needed for the liberation of the amine or a salt of nipecotic acid derivative of formula (XI) formed with inorganic base, for example potassium salt is used in the reaction. The reactions are followed by thin layer chromatography. The necessary reaction time is 3-20 h. The work-up of the reaction mixture can be carried out by different methods.

When the N-arylated product is an acid derivative of formula (I) and the reaction mixture is a suspension, the inorganic salt is filtered off, the filtrate is diluted with water and acidified with acetic acid. The product is isolated by filtration or extraction with a proper organic solvent and in given case purified by crystallization or column chromatography. If the reaction mixture is a solution, it is diluted with water and acidified with acetic acid. The product is isolated by filtration or extraction with a proper organic solvent and in given case purified by crystallization or column chromatography.

When the N-arylated product is an ester derivative of formula (XII), the reaction mixture is evaporated in vacuo. The product is isolated by crystallization or extraction with a proper organic solvent and in given case purified by recrystallization or column chromatography.

The hydrolysis of the carboxylic acid ester derivative of formula (XIII) into the carboxylic acid derivative of formula (I) can be carried out with an appropriate strong inorganic base, e.g. lithium hydroxide, sodium hydroxide or with an appropriate strong inorganic acid, e.g. hydrochloric acid. The reaction is preferably carried out between room temperature and 100° C. The reactions are followed by thin layer chromatography. The necessary reaction time is 1-20 h. The reaction mixture is diluted with water and acidified with acetic acid. The product is isolated by filtration or extraction with a proper organic solvent and in given case purified by crystallization or column chromatography. The structures of the products are determined by NMR and mass spectrometry.

Most of the nipecotic acid derivatives of formula (X) and (XII) are either commercially available or can be synthesized by different known methods. The syntheses of some new nipecotic acid derivatives of formula (XII) are described in the Intermediate section.

The compounds of the present invention and optical antipodes or racemates and/or salts thereof can be used as such or suitably in the form of pharmaceutical compositions.

The invention also relates to the pharmaceutical compositions containing the compounds of formula (I) or pharmaceutically acceptable salts, biologically active metabolites, pro-drugs, racemates, enantiomers, diastereomers, solvates and hydrates thereof for the treatment of certain disorders associated with $GABA_B$ receptor positive allosteric modulator activity.

The present compounds may be coadministered to a subject in combination with two or more different therapeutic agents (eg. most preferably antipsychotics and psychostimulants; and preferably antidepressants, anxiolytics, antihypertensives, anticonvulsants, sedatives, and narcotics).

Suitable routes of administration may, for example, include oral, rectal, transmucosal, transdermal or intestinal administration; parenteral delivery, including intramuscular, subcutaneous, intravenous, intramedullary injections, as well as intraarticular, intrathecal, direct intraventricular, intraperitoneal, intranasal, or intraocular injections and eye drops.

Alternatively, one may administer the compound in a local rather than systemic manner, for example, via injection of the compound directly in the renal or cardiac area, often in a depot or sustained release formulation. Furthermore, one may administer the drug in a targeted drug delivery system, for example, in a liposome coated with a tissue-specific antibody. The liposomes will be targeted to and taken up selectively by the organ.

The pharmaceutical compositions can be administered through a variety of routes and dosages forms. The compound of the invention may be administered either alone or in combination with pharmaceutically acceptable carriers, in either single or multiple doses. The dosage required to exert the therapeutical effect can vary within wide limits and will be fitted to the individual requirements in each of the particular case, depending on the stage of the disease, the condition and the bodyweight of the patient to be treated, as well as the sensitivity of the patient against the active ingredient, route of administration and number of daily treatments.

In case of a simple administration it is suitable if the pharmaceutical compositions comprise dosage units containing the amount of the active ingredient to be administered once, or a few multiples or a half, third or fourth part thereof. Such dosage units are e.g. tablets, which can be powdered with grooves promoting the halving or quartering of the tablet in order to exactly administer the required amount of the active ingredient.

The pharmaceutical compositions containing the active ingredient according to the present invention usually contain 0.01 to 500 mg of active ingredient in a single dosage unit. It is, of course possible that the amount of the active ingredient in some compositions exceeds the upper or lower limits defined above.

As a further aspect of the invention there is provided the pharmaceutical manufacture of medicaments containing the compounds of formula (I) or optical antipodes or racemates and/or salts thereof.

The pharmaceutical compositions of the present invention may be formulated as different pharmaceutical dosage forms, such as but not limited to, solid oral dosage forms like tablets (e.g. buccal, sublingual, effervescents, chewable, orodispersible, freeze dried), capsules, lozenges, pastilles, pills, orodispersible films, granules, powders; liquid oral dosage forms like solutions, emulsions, suspensions, syrups, elixirs, oral drops; parenteral dosage forms like intravenous injections, intramuscular injections, subcutaneous injections; other dosage forms like eye drops, semi-solid eye preparations, transdermal dosage forms, suppositories, rectal capsules, rectal solutions, emulsions and suspensions, etc.

In one embodiment the invention relates to pharmaceutical dosage forms specifically intended for pediatric use, such as but not limited to, solutions, syrups, elixirs, suspensions, powders for reconstitution as suspension, dispersible or effervescent tablets, chewable tablets, orally disintegrating tablets, tablets or coated tablets, sprinkle oral powder or granules, capsules.

The pharmaceutical compositions of the present invention may be manufactured in a manner that is itself known, e.g., by means of conventional mixing, dissolving, emulsifying, suspending, entrapping, freeze-drying, extrusion, laminating, film-casting, granulating, grinding, encapsulating, dragee-making or tabletting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art.

Suitable excipients for the preparation of the dosage forms may be selected from the following categories, such as but not limited to, tablet and capsule fillers, tablet and capsule binders, modified-release agents, disintegrants, glidants, lubricants, sweetening agents, taste-masking agents, flavoring agents, coating agents, surfactants, antioxidants, buffering agents, complexing agents, emulsifying agents, lyophilization aids, microencapsulating agents, ointment bases, penetration enhancers, solubilizing agents, solvents, suppository bases, suspending agents.

In one embodiment the invention relates to the using of specific excipients which are able to improve the solubility, dissolution, penetration, adsorption or bioavailability of the active ingredient(s), such as but not limited to, hydrophilic polymers, hot melt extrusion excipients, surfactants, buffering agents, complexing agents, emulsifying agents, lyophilization aids, superdisintegrants, microencapsulating agents, penetration enhancers, solubilizing agents, co-solvents, suspending agents.

The above described ingredients and different routes of manufacture are merely representative. Other materials as well as processing techniques and the like well known in the art can also be used.

The compounds would be effective in the treatment of psychiatric, neurodevelopmental, neurological and other central nervous system disorders as well as peripheral conditions where stimulation of the $GABA_B$ receptor may offer therapeutic benefit.

Biological Evaluation

In Vitro [$^{35}$S]GTPγS Binding Assay in Rat Cortical Membranes

Cortices of freshly harvested rat brains were dissected on an ice-cold surface and homogenized by a glass Dounce homogeniser immediately in ice-cold buffer containing 50 mM Tris, 5 mM $MgCl_2$ and 1 mM EDTA (pH=7.6). Tissue homogenates were centrifuged at 40000 g for 15 min at 4° C. Membrane pellets were resuspended in the same buffer and membranes were incubated for 10 min at 30° C. in a shaking water bath to eliminate endogenous GABA. Homogenates were centrifuged again under the same conditions. The final pellets were resuspended in ice-cold buffer (pH=7.6) containing 50 mM Tris, 100 mM NaCl, 7 mM $MgCl_2$, 1 mM EDTA and 1 mM dithiotreithol (DTT) to yield a concentration of 20 mg tissue weight/ml and frozen at −70° C. until use. The assay was done in a buffer containing 50 mM Tris (pH=7.4), 100 mM NaCl, 7 mM $MgCl_2$, 1 mM EDTA and 1 mM DTT. Each assay tube contained 150 μL GDP (in a final concentration of 50 μM), 100 μL ligand and 125 μL of the membrane suspension (250 μg tissue/tube). The assay tubes were preincubated for 10 min at 30° C. to assure equilibrium. Nonspecific binding was determined in the presence of 10 μM GTPγS; basal binding was determined in the presence of buffer only. After addition of 50 μM [$^{35}$S]GTPγS in a volume of 25 μL to the tubes, membranes were incubated for an additional 60 min at 30° C. The assay was terminated by rapid filtration through Packard UniFilter GF/B using a Packard harvester and washed four times with 1 ml ice-cold buffer. After drying the filters at 40° C. for 1 h, 40 μL Microscint (Packard) was added to the filters and radioactivity of the filters was determined by a TopCount NXT (PerkinElmer, Waltham, Mass.; Alper and Nelson, *Eur.* *J. Pharmacol.* 1998, 343, 303-312; Rinken et al, *Biochem. Pharmacol.* 1999, 57, 155-162). Data thus gathered were used to determine PAM $EC_{50}$ values for each compound as primary in vitro activity end point.

In Table 1 compounds of this invention measured in the [$^{35}$S]GTPγS binding assay are listed.

TABLE 1

| Number of example | In vitro PAM potency |
|---|---|
| 3 | +++ |
| 5 | +++ |
| 6 | +++ |
| 7 | ++ |
| 9 | +++ |
| 10 | ++ |
| 11 | ++ |
| 12 | ++ |
| 13 | ++ |
| 14 | +++ |
| 15 | ++ |
| 16 | +++ |
| 17 | ++ |
| 20 | +++ |
| 21 | +++ |
| 22 | +++ |
| 28 | +++ |
| 45 | +++ |
| 58 | +++ |
| 84 | ++ |

+ PAM $EC_{50}$ < 1 nM
++ 1 nM ≤ PAM $EC_{50}$ < 10 nM
+++ 10 nM ≤ PAM $EC_{50}$ < 100 nM

Foot Shock-Induced Ultrasonic Vocalization (USV) in Adult Rats

Under stressful conditions, adult rats emit 22 kHz ultrasounds that can be reduced by various pharmacological treatments (De Vry et al, *Eur. J. Pharmacol.* 1993, 249, 331-339; Sanchez, *Eur. J. Pharmacol.* 2003, 463, 133-143). Previous unpublished experiments indicated that $GABA_B$ receptor ligands can also inhibit vocalizatons that are induced by electric footshocks as stressor. Therefore, a foot shock-induced vocalization paradigm in adult rats was used to assess in vivo efficacy of centrally acting $GABA_B$ receptor ligands. Behavioral measurements were carried out on male Wistar rats (200-250 g, Toxicoop, Hungary). Rats were housed in groups of four in plastic cages with a wire grid top in a temperature and light-controlled laboratory animal care unit (22±2° C., 12-h light/dark cycle, lights on at 6:00 AM) with ad libitum access to commercial pellet rat food and tap water. Investigations were approved by the Local Ethical Committee of Gedeon Richter Plc. and were carried out in strict compliance with the European Directive 2010/63/EU regarding the care and use of laboratory animals for experimental procedures and all efforts were made to minimize the number of animals as well as their suffering. In order to evoke emission of ultrasounds, animals were footshocked after a habituation period of 30 s (6 shocks, 1 s, 0.8 mA each, inter-shock interval 10 s) in a sound attenuated shocking chamber (Experimetria, 40×40×80 cm). Investigational compounds were administered at the dose of 10 mg/kg in a solid dispersion formulation or Tween80 suspension in distilled water 1 h before shocking per os. Vocalizations were measured right after the last footshock for 10 min with a Metris Sonotrack system and the total time of vocalizations was registered. Vocalization of parallel vehicle treated animals was considered as control value and inhibition percent was calculated for each compound. At approximately 75 min after treatment and behavioral measurements, blood and brain samples were harvested in order to determine exposures associated with in vivo activity.

In Table 2 compounds of this invention measured in the USV assay are listed. In Table 3 plasma and brain levels of compounds of this invention are listed.

TABLE 2

| Number of example | USV inhibition at 10 mg/kg (%) |
|---|---|
| 3 | 58 |
| 5 | 37 |
| 6 | 90 |
| 7 | 90 |
| 8 | 60 |
| 9 | 39 |
| 10 | 30 |
| 11 | 15 |
| 12 | 63 |
| 13 | 90 |
| 14 | 47 |
| 15 | 85 |
| 16 | 41 |
| 17 | 44 |
| 70 | 71 |
| 28 | 35 |
| 84 | 42 (at 3 mg/kg) |

TABLE 3

| Number of example | Plasma exposure at 1 mg/kg (ng/mL) | Brain exposure at 1 mg/kg (ng/g) | Formulation |
|---|---|---|---|
| 3 | 358 | 395 | Tween |
| 5 | 1472 | 857 | SpD1 |
| 6 | 1453 | 1326 | Tween |
| 7 | 506 | 332 | Tween |
| 8 | 298 | 1193 | Tween |
| 9 | 1807 | 1849 | SpD1 |
| 10 | 36 | 150 | Tween |
| 11 | 326 | 165 | Tween |
| 12 | 283 | 218 | Tween |
| 13 | 843 | 424 | Tween |
| 14 | 2323 | 1962 | SpD1 |
| 15 | 1317 | 1377 | SpD1 |
| 16 | 103 | 28 | Tween |
| 17 | 443 | 144 | Tween |
| 20 | 1275 | 1093 | SpD1 |
| 28 | 222 | 184 | Tween |
| 84 | 113 | 85 | Tween |

Prenatal Valproate Model of Autism Spectrum Disorder (ASD)

The prenatal valproate model has excellent construct and face validity, therefore it is a widely accepted disease model of ASD (Christensen et al, JAMA 2013, 309, 1696-1703; Roullet et al, Neurotox. Teratol. 2013, 36, 45-56). In this method, time-mated female Wistar rats (Harlan UK) were administered a single dose of valproic acid (VPA, 600 mg/kg, i.p.) on gestational day 12.5. Male offspring were housed according to standard laboratory conditions until time of testing at postnatal day 59. Animals were housed in groups of 4 in conventional cages and maintained at 22-24° C. on a standard 12 hour light/dark cycle (07.30-19.30), with food and water available ad libitum. After investigational drug treatment, offspring were examined behaviorally in the social preference assay at postnatal day 59. The social preference test is a highly accepted assay to assess autistic behavior in rodents (Nadler et al, Genes Brain Behav. 2007, 3, 303-314; Bambini-Junior et al, Brain Res. 2011, 1408, 8-16). Briefly, in this assay a test animal is allowed to investigate a conspecific separated by a dividing perforated wall or a similar area however, without a target conspecific. An autistic animal (such as a prenatally valproate-exposed rat) spends little time with social investigation during a test session.

The inventors unexpectedly found that selected compounds of the invention in the oral dose range of 0.25-2 mg/kg were of great behavioral benefit in the present preclinical disease model that recapitulates the core symptoms of ASD. The inventors therefore showed that these compounds may be of therapeutic potential for the treatment of core symptoms of ASD in humans.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather defined by the claims appended hereto.

In general, the compounds of Formula I can be prepared in accordance with the general knowledge of one skilled in the art and/or using methods set forth in the Example and/or Intermediate sections that follow. Solvents, temperatures, pressures, and other reaction conditions can readily be selected by one of ordinary skill in the art. Starting materials are commercially available and/or readily prepared by one skilled in the art.

Our patent application filed concurrently herewith titled "Process for the separation of optical isomers of racemic 3-alkylpiperidine-carboxylic acid ethyl esters" discloses the preparation of certain starting materials.

The present invention will be now illustrated by the following not limiting examples.

Intermediate 1

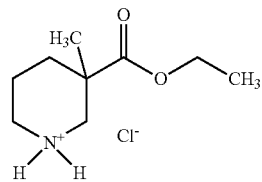

Ethyl 3-methylpiperidine-3-carboxylate a) 1-Tert-butyl 3-ethyl 3-methylpiperidine-1,3-dicarboxylate Under nitrogen to a solution of 22.96 g (89 mmol) of 1-tert-butyl 3-ethyl piperidine-1,3-dicarboxylate in 300 mL of dry tetrahydrofuran 100 mL of 1 M lithium bis(trimethylsilyl)amide in tetrahydrofuran solution (100 mmol) was added dropwise at (−78) ° C.-(−65) ° C. After addition the mixture was stirred at −78° C. for 20 min, 6.6 mL (106 mmol) of iodomethane was added dropwise. The so obtained mixture was allowed to warm to room temperature and stirred at this temperature for 18 h. The reaction was quenched by addition of 200 mL of saturated ammonium chloride solution (pH~8) and 300 mL of water. The reaction mixture was extracted with ethyl acetate, the combined organic layer was washed with water, dried over anhydrous sodium sulfate, filtered and concentrated in vacuo. The residue was chromatographed on silica gel eluting with ethylacetate and cyclohexane (1:4) to yield 24.2 g (95%) of the title compound as oil.

b) Ethyl 3-methylpiperidine-3-carboxylate

To a solution of 50 ml of 2.5 M hydrochloric acid in ethyl acetate 24.2 g (84.8 mmol) of 1-tert-butyl 3-ethyl 3-methylpiperidine-1,3-dicarboxylate was added. The reaction mixture was stirred for 3 h at 20° C., then 100 mL of diethyl ether was added. The precipitated crystals were filtered off, washed with diethyl ether to yield 16.28 g (97%) of the title compound. Mp.: 119-120° C.

Intermediate 2

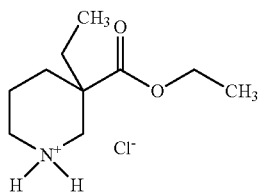

Ethyl 3-ethylpiperidine-3-carboxylate a) 1-tert-Butyl 3-ethyl 3-ethylpiperidine-1,3-dicarboxylate The title compound is prepared from 1-tert-butyl 3-ethyl piperidine-1,3-dicarboxylate and iodo ethane according to the method described in Intermediate 1a.

b) Ethyl 3-ethylpiperidine-3-carboxylate hydrochloride

The title compound is prepared from 1-tert-butyl 3-ethyl 3-ethylpiperidine-1,3-dicarboxylate according to the method described in Intermediate 1b. Mp.: 128-131° C.

Intermediate 3

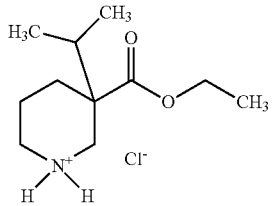

Ethyl 3-(propan-2-yl)piperidine-3-carboxylate hydrochloride a) 1-tert-Butyl 3-ethyl 3-(propan-2-yl)piperidine-1,3-dicarboxylate The title compound is prepared from 1-tert-butyl 3-ethyl piperidine-1,3-dicarboxylate and 2-iodo propane according to the method described in Intermediate 1a.

b) Ethyl 3-(propan-2-yl)piperidine-3-carboxylate

The title compound is prepared from 1-tert-butyl 3-ethyl 3-(propan-2-yl)piperidine-1,3-dicarboxylate according to the method described in Intermediate 1b. Mp.: 128-130° C.

Intermediate 4

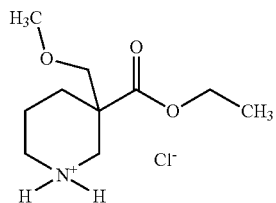

Ethyl 3-(methoxymethyl)piperidine-3-carboxylate hydrochloride a) 1-tert-Butyl 3-ethyl 3-(methoxymethyl)piperidine-1,3-dicarboxylate The title compound is prepared from 1-tert-butyl 3-ethyl piperidine-1,3-dicarboxylate and chloromethyl methyl ether according to the method described in Intermediate 1a.

b) Ethyl 3-(methoxymethyl)piperidine-3-carboxylate hydrochloride

The title compound is prepared from 1-tert-butyl 3-ethyl 3-(methoxymethyl)piperidine-1,3-dicarboxylate according to the method described in Intermediate 1b. Mp.: 98-99° C.

Intermediate 5

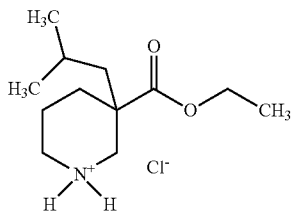

Ethyl 3-(2-methylpropyl)piperidine-3-carboxylate hydrochloride a) 1-tert-Butyl 3-ethyl 3-(2-methylpropyl)piperidine-1,3-dicarboxylate The title compound is prepared from 1-tert-butyl 3-ethyl piperidine-1,3-dicarboxylate and 1-iodo-2-methylpropane according to the method described in Intermediate 1a.

b) Ethyl 3-(2-methylpropyl)piperidine-3-carboxylate hydrochloride

The title compound is prepared from 1-tert-butyl 3-ethyl 3-(2-methylpropyl)piperidine-1,3-dicarboxylate according to the method described in Intermediate 1b. Oil.

Intermediate 6

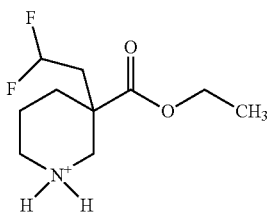

Ethyl 3-(2,2-difluoroethyl)piperidine-3-carboxylate hydrochloride a) 1-tert-Butyl 3-ethyl 3-(2,2-difluoroethyl)piperidine-1,3-dicarboxylate

The title compound is prepared from 1-tert-butyl 3-ethyl piperidine-1,3-dicarboxylate and 1-iodo-1,1-difluoroethane according to the method described in Intermediate 1a.

b) Ethyl 3-(2,2-difluoroethyl)piperidine-3-carboxylate hydrochloride

The title compound is prepared from 1-tert-butyl 3-ethyl 3-(2,2-difluoroethyl)piperidine-1,3-dicarboxylate according to the method described in Intermediate 1b. Oil.

Intermediate 7

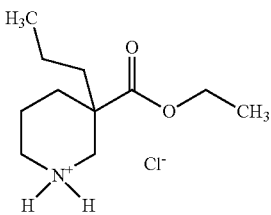

Ethyl 3-propylpiperidine-3-carboxylate hydrochloride a) 1-tert-butyl 3-ethyl 3-propylpiperidine-1,3-dicarboxylate

The title compound is prepared from 1-tert-butyl 3-ethyl piperidine-1,3-dicarboxylate and 1-iodopropane according to the method described in Intermediate 1a.

b) ethyl 3-propylpiperidine-3-carboxylate hydrochloride

The title compound is prepared from 1-tert-butyl 3-ethyl 3-propylpiperidine-1,3-dicarboxylate according to the method described in Intermediate 1b. Mp.: 98-99° C.

Intermediate 8

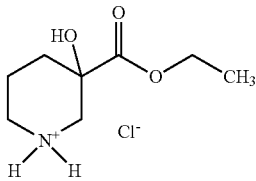

Ethyl 3-hydroxypiperidine-3-carboxylate hydrochloride a) 1-Benzyl-3-hydroxypiperidine-3-carbonitrile

To a stirred solution of 10.0 g (44 mmol) of 1-benzyl-3-piperidone hydrochloride hydrate and 3.28 g (66.9 mmol) of sodium cyanide in mixture of 28 ml of tetrahydrofurane and 56 mL of water 17.1 mL of 40% sodium hydrogen sulfite in 46 ml of water was added dropwise at 0° C. The reaction mixture was stirred at this temperature for 1.5 h. The reaction mixture was extracted with dichloromethane, the combined organic layer was washed with water, dried over anhydrous sodium sulfate, filtered and concentrated in vacuo to yield 10.35 g of the title compound as oil.

b) Ethyl 1-benzyl-3-hydroxypiperidine-3-carboxylate

The above obtained 1-benzyl-3-hydroxypiperidine-3-carbonitrile was solved in 25 ml of cc. hydrochloric acid and refluxed for 3 h. The solvent was removed in vacuo and dry toluene then ethanol was evaporated from the residue several times. The dried residue was dissolved in 100 ml of ethanol and 5 ml of cc. hydrochloric acid was added. The reaction mixture was neutralised with sodium carbonate and extracted with ethyl acetate. The combined organic layer was washed with water, dried over anhydrous sodium sulfate, filtered and concentrated in vacuo to yield 10.33 g of the title compound as oil.

c) Ethyl 3-hydroxypiperidine-3-carboxylate hydrochloride

A mixture of 3 g (11.4 mmol) of ethyl 1-benzyl-3-hydroxypiperidine-3-carboxylate, 75 ml of ethanol and 0.3 g of Pd(OH)$_2$ catalyst was hydrogenated. After completion of the reaction, the catalyst is filtered off, washed with ethanol and the filtrate was concentrated to obtain the title compound as oil.

Intermediate 9

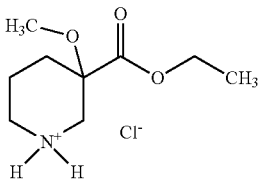

Ethyl 3-methoxypiperidine-3-carboxylate hydrochloride a) 1-tert-Butyl 3-ethyl 3-hydroxypiperidine-1,3-dicarboxylate

A mixture of 3.82 g (14.5 mmol) of ethyl 1-benzyl-3-hydroxypiperidine-3-carboxylate (Intermediate 8b), 3.17 g (14.5 mmol) of ditert-butyl-dicarbonate, 100 ml of ethanol and 0.5 g of Pd(OH)$_2$ catalyst was hydrogenated. After completion of the reaction, the catalyst is filtered off, washed with ethanol and the filtrate was concentrated. The residue was chromatographed on silica gel eluting with ethylacetate and cyclohexane (1:2) to yield 3.05 g (76%) of the title compound as oil.

b) 1-tert-Butyl 3-ethyl 3-methoxypiperidine-1,3-dicarboxylate

Under nitrogen, to a stirred solution of 3.0 g (11 mmol) of 1-tert-butyl 3-ethyl 3-hydroxypiperidine-1,3-dicarboxylate in 20 ml of dimethylformamide 0.6 g (60%, 15.6 mmol) of sodium hydride was added. The reaction mixture was stirred for 15 min at room temperature, then 1.63 ml (25.7 mmol) of iodomethane was added. The reaction mixture was stirred for 4 h at room temperature. The reaction was quenched by addition of 20 mL of saturated ammonium chloride solution and 30 mL of water. The reaction mixture was extracted with ethyl acetate, the combined organic layer was washed with water, dried over anhydrous sodium sulfate, filtered and concentrated in vacuo. The residue was chromatographed on silica gel eluting with ethylacetate and cyclohexane (1:2) to yield 2.62 g (82%) of the title compound as oil.

c) Ethyl 3-methoxypiperidine-3-carboxylate hydrochloride

To a solution of 15 ml of 2.5 M hydrochloric acid in ethyl acetate 2.62 g (9.1 mmol) of 1-tert-butyl 3-ethyl 3-methoxypiperidine-1,3-dicarboxylate was added. The reaction mixture was stirred for 3 h at 20° C., and concentrated in vacuo to obtain the title compound as oil.

Intermediate 10

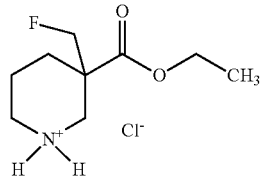

Ethyl 3-(fluoromethyl)piperidine-3-carboxylate hydrochloride a) 1-tert-butyl 3-ethyl 3-(hydroxymethyl)piperidine-1,3-dicarboxylate The title compound is prepared from 1-tert-butyl 3-ethyl piperidine-1,3-dicarboxylate and paraformaldehyde according to the method described in Intermediate 1a.

b) 1-tert-butyl 3-ethyl 3-{[(trifluoromethanesulfonyl)oxy]methyl}piperidine-1,3-dicarboxylate Under nitrogen, to a stirred solution of 0.296 g (1.03 mmol) of ethyl 3-(hydroxymethyl) piperidine-3-carboxylate and 0.120 ml (1.48 mmol) of pyridine in 5 ml of dichloromethane 0.230 ml (1.48 mmol) of trifluoromethanesulfonic anhydride was added dropwise at (−78) ° C.-(−65) ° C. After addition the mixture was stirred at −78° C. for 5 min and allowed to warm to room temperature and stirred at this temperature for 18 h. The reaction was quenched by addition of 1M hydrochloric acid solution. The reaction mixture was extracted with dichloromethane, the combined organic layer was washed with water, dried over anhydrous sodium sulfate, filtered and concentrated in vacuo to obtain the title compound as oil. The crude product is used in the next step.

c) 1-tert-Butyl 3-ethyl 3-(fluoromethyl)piperidine-1,3-dicarboxylate

The above obtained 1-tert-butyl 3-ethyl 3-{[(trifluoromethanesulfonyl)oxy]methyl}piperidine-1,3-dicarboxylate was solved in 4 ml of tetrahydrofuran and 1.25 ml (1.25 mmol) of 1M tetrabutylammonium fluoride in tetrahydrofuran was added. The reaction mixture was stirred for 1 h at room temperature, diluted with water and extracted with ethylacetate. The combined organic layer was washed with water, dried over anhydrous sodium sulfate, filtered and concentrated ii, vacuo. The residue was chromatographed on silica gel eluting with ethylacetate and cyclohexane (1:2) to yield 0.121 g (400/%) of the title compound.

d) Ethyl 3-(fluoromethyl)piperidine-3-carboxylate hydrochloride

The title compound is prepared from 1-tert-Butyl 3-ethyl 3-(fluoromethyl)piperidine-1,3-dicarboxylate according to the method described in Intermediate 1b.

Intermediate 11

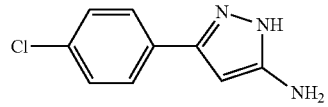

3-(4-Chlorphenyl-1H-pyrazol-5-amine a) 3-(4-Chlorophenyl)-3-oxopropanenitrile

To a solution of 59.0 g (346 mmol) of methyl 4-chlorobenzoate in 690 mL of acetonitrile 37.37 g (692 mmol) sodium methylate was added in nitrogen atmosphere and the mixture was refluxed for 6 h. The reaction mixture was cooled and poured into 500 mL of water. The pH of the mixture was adjusted to 3 by the addition of 2M hydrochloric acid. The precipitated product was filtered off and washed with water to yield 60.66 g (97.6%) of the title compound. Mp.: 130-143° C.

b) 3-(4-Chlorophenyl)-H-pyrazol-5-amine

A mixture of 60.66 g (337 mmol) of 3-(4-chlorophenyl)-3-oxopropanenitrile, 43.46 ml of hydrazine hydrate in 1660 ml of ethanol was refluxed for 3 h. The reaction mixture was cooled and diluted with water (300 mL). The ethanol was evaporated under reduced pressure. The precipitated crystals were filtered off and washed with water to yield 34.84 g (53.2%) of the title compound. Mp.: 168-173° C.

Compounds of Table 4 were prepared from the appropriate carboxylic acid ester and acetonitrile with sodium methylate according to the method described in Intermediate 11.

TABLE 4

| Intermediate | Structure |
|---|---|
| 12 | 3-[4-(trifluoromethyl)phenyl]-1H-pyrazol-5-amine |
| 13 | 3-(4-methylphenyl)-1H-pyrazol-5-amine |
| 14 | 3-(4-bromophenyl)-1H-pyrazol-5-amine |
| 15 | 3-phenyl-1H-pyrazol-5-amine |
| 16 | 3-(4-chlorophenyl)-4-methyl-1H-pyrazol-5-amine |
| 17 | 3-(pyridin-4-yl)-1H-pyrazol-5-amine |
| 18 | 3-[4-(trifluoromethoxy)phenyl]-1H-pyrazol-5-amine |
| 19 | 3-[6-(trifluoromethyl)pyridin-3-yl]-1H-pyrazol-5-amine |
| 20 | 3-(2-chlorophenyl)-1H-pyrazol-5-amine |
| 21 | 3-(2,4-dichlorophenyl)-1H-pyrazol-5-amine |
| 22 | 3-(3,4-dichlorophenyl)-1H-pyrazol-5-amine |
| 23 | 3-(3,5-dichlorophenyl)-1H-pyrazol-5-amine |
| 24 | 3-(4-ethoxyphenyl)-1H-pyrazol-5-amine |
| 25 | 4-(5-amino-1H-pyrazol-3-yl)benzonitrile |
| 26 | 3-[3-(trifluoromethyl)phenyl]-1H-pyrazol-5-amine |

Intermediate 27

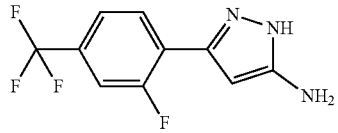 [SMILES: Nc1cc(-c2ccc(C(F)(F)F)cc2F)n[nH]1]

3-[2-Fluoro-4-(trifluoromethyl)phenyl]-1H-pyrazol-5-amine a) 3-[2-Fluoro-4-(trifluoromethyl)phenyl]-3-oxopropanenitrile Under nitrogen to a mixture of 9 mL (172 mmol) of acetonitrile in 300 mL of dry tetrahydrofuran 53 mL of 2.5 M n-butyllithium in n-hexane solution (132.5 mmol) was added dropwise at (−78) ° C.-(−65) ° C. After addition the mixture was stirred at −78° C. for 10 min, 10.3 g (45.46 mmol) of 2-fluoro-4-(trifluoromethyl)benzoyl chloride was added dropwise. The so obtained mixture was allowed to warm to room temperature and stirred at this temperature for 1 h. The reaction was quenched by addition of 150 mL of saturated ammonium chloride solution. The tetrahydrofuran was evaporated and the precipitated crystals were filtered off to yield 0.7 g (64%) of the title compound the residue is treated with water and the crystals were filtered off to obtain the title compound. The crude wet product is used in the next step.

b) 3-[2-Fluoro-4-(trifluoromethyl)phenyl]-1H-pyrazol-5-amine

The above obtained 3-[2-fluoro-4-(trifluoromethyl)phenyl]-3-oxopropanenitrile was solved in 220 ml of ethanol and 4.4 ml (90.7 mmol) of hydrazine monohydrate was added. Under inert gas atmosphere, the reaction mixture was refluxed for 16 h. The solvent was removed in vacuo and dry toluene was evaporated from the residue several times to yield 10.33 g of the title compound as red oil.

Compounds of Table 5 were prepared from the appropriate carboxylic acid chloride and acetonitrile with n-buthyl-lithium according to the method described in Intermediate 27.

TABLE 5

| Intermediate | Structure |
|---|---|
| 28 | ![structure] |
| 29 | ![structure] |
| 30 | ![structure] |
| 31 | ![structure] |
| 32 | ![structure] |
| 33 | ![structure] |
| 34 | ![structure] |
| 35 | ![structure] |

Intermediate 36

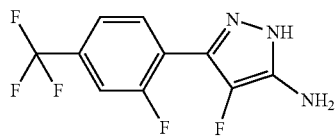 [SMILES: Nc1[nH]nc(-c2ccc(C(F)(F)F)cc2F)c1F]

4-Fluoro-3-[2-fluoro-4-(trifluoromethyl)phenyl]-1H-pyrazol-5-amine a) 2-Fluoro-3-[2-fluoro-4-(trifluoromethyl)phenyl]-3-oxopropanenitrile Under inert gas atmosphere, to a solution of 5.43 g (23.97 mmol) of 2-fluoro-4-(trifluoromethyl)benzoyl chloride and 1.5 ml (26.96 mmol) of fluoroacetonitrile in 80 mL of abs. tetrahydrofuran 50 mL (50 mmol) of 1M lithium bis(trimethylsilyl)amide was added dropwise at −78° C. The mixture was allowed to warm to room temperature and poured into 200 mL of water. The pH of the mixture was adjusted to 2 by the addition of 1M hydrochloric acid. The mixture was extracted with ethyl acetate, the combined organic layer was washed with water, dried over anhydrous sodium sulfate, filtered and concentrated in vacuo. The crude product is used in the next step.

b) 4-Fluoro-3-[2-fluoro-4-(trifluoromethyl)phenyl]-H-pyrazol-5-amine

The above obtained 2-fluoro-3-[2-fluoro-4-(trifluoromethyl)phenyl]-3-oxopropanenitrile was solved in 80 ml of ethanol and 2.76 ml (56.9 mmol) of hydrazine monohydrate was added. Under inert gas atmosphere, the reaction mixture was refluxed for 2 h, then concentrated in vacuo. The residue was partitioned between ethyl acetate and water. The combined organic layer was washed with water, dried over anhydrous sodium sulfate, filtered and concentrated in vacuo. The crude product is used in the next step.

Compounds of Table 6 were prepared from the appropriate carboxylic acid chloride and fluoroacetonitrile with lithium bis(trimethylsilyl)amide according to the method described in Intermediate 36.

TABLE 6

| Intermediate | Structure |
|---|---|
| 37 | ![structure] |
| 38 | ![structure] |

TABLE 6-continued

| Intermediate | Structure |
|---|---|
| 39 | 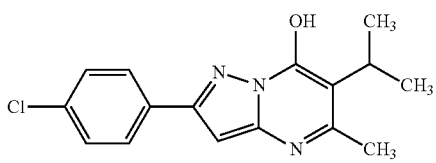 |

Intermediate 40

2-(4-Chlorophenyl)-5-methyl-6-(propan-2-yl)pyrazolo[1,5-a]pyrimidin-7-ol a) 2-(4-Chlorophenyl)-5-methyl-6-(methylsulfanyl)pyrazolo[1,5-a]pyrimidin-7-ol A mixture of 17.42 g (90 mmol) of 3-(4-chlorophenyl)-1H-pyrazol-5-amine (Intermediate 11), 15.83 g (91.9 mmol) of ethyl 2-acetyl-3-methylbutanoate and 0.52 g (2.7 mmol) of p-toluenesulfonic acid monohydrate in 343 mL of toluene was refluxed for 20 h, then cooled to room temperature. The precipitated crystals were filtered off, washed with toluene to yield 24.88 g (89.9%) of the title compound. Mp.: 315-323° C.

Compounds of Table 7 were prepared from the appropriate acetoacetic ester and 1H-pyrazol-5-amine according to the method described in Intermediate 40.

TABLE 7

| Intermediate | Structure | Intermediate (starting material) |
|---|---|---|
| 41 | 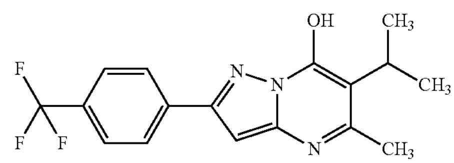 [SMILES: Cc1nc2cc(-c3ccc(C(F)(F)F)cc3)nn2c(O)c1C(C)C] | 12 |
| 42 | 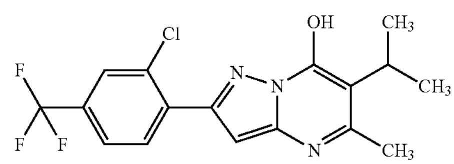 [SMILES: Cc1nc2cc(-c3ccc(C(F)(F)F)cc3Cl)nn2c(O)c1C(C)C] | 28 |
| 43 | 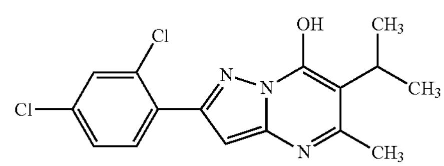 [SMILES: Cc1nc2cc(-c3ccc(Cl)cc3Cl)nn2c(O)c1C(C)C] | 21 |
| 44 | 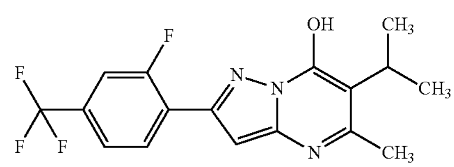 [SMILES: Cc1nc2cc(-c3ccc(C(F)(F)F)cc3F)nn2c(O)c1C(C)C] | 27 |
| 45 | 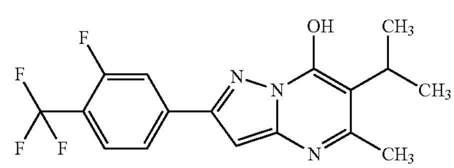 | 35 |
| 46 | 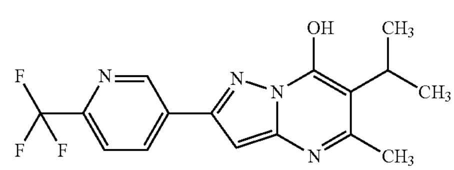 [SMILES: Cc1nc2cc(-c3ccc(C(F)(F)F)nc3)nn2c(O)c1C(C)C] | 19 |

TABLE 7-continued

| Intermediate | Structure | Intermediate (starting material) |
|---|---|---|
| 47 | 2-(4-(trifluoromethyl)phenyl)-3-fluoro-6-isopropyl-5-methyl-pyrazolo[1,5-a]pyrimidin-7-ol | 39 |
| 48 | 2-(4-chlorophenyl)-3-fluoro-6-isopropyl-5-methyl-pyrazolo[1,5-a]pyrimidin-7-ol | 38 |
| 49 | 2-(4-methylphenyl)-3-fluoro-6-isopropyl-5-methyl-pyrazolo[1,5-a]pyrimidin-7-ol | 37 |
| 50 | 2-(4-chlorophenyl)-3-fluoro-6-ethyl-5-methyl-pyrazolo[1,5-a]pyrimidin-7-ol | 38 |
| 51 | 2-(4-chlorophenyl)-3-methyl-5-(trifluoromethyl)-pyrazolo[1,5-a]pyrimidin-7-ol | 16 |
| 52 | 2-(4-chlorophenyl)-3-fluoro-6-(methylthio)-5-methyl-pyrazolo[1,5-a]pyrimidin-7-ol | 38 |
| 53 | 2-(4-chlorophenyl)-3-fluoro-6-methoxy-5-methyl-pyrazolo[1,5-a]pyrimidin-7-ol | 38 |
| 54 | 2-(4-chlorophenyl)-3-fluoro-6-isopropoxy-5-methyl-pyrazolo[1,5-a]pyrimidin-7-ol | 38 |

TABLE 7-continued

| Intermediate | Structure | Intermediate (starting material) |
|---|---|---|
| 55 | 2-(4-chloro-2-fluorophenyl)-7-hydroxy-6-isopropyl-5-methylpyrazolo[1,5-a]pyrimidine | 34 |
| 56 | 2-(4-chloro-2,6-difluorophenyl)-7-hydroxy-6-isopropyl-5-methylpyrazolo[1,5-a]pyrimidine | 32 |
| 57 | 7-hydroxy-6-isopropyl-5-methyl-2-(p-tolyl)pyrazolo[1,5-a]pyrimidine | 13 |
| 58 | 2-(4-ethylphenyl)-7-hydroxy-6-isopropyl-5-methylpyrazolo[1,5-a]pyrimidine | 33 |
| 59 | 7-hydroxy-6-isopropyl-5-methyl-2-phenylpyrazolo[1,5-a]pyrimidine | 15 |
| 60 | 2-(4-bromophenyl)-7-hydroxy-6-isopropyl-5-methylpyrazolo[1,5-a]pyrimidine | 14 |
| 61 | 7-hydroxy-6-isopropyl-5-methyl-2-(pyridin-4-yl)pyrazolo[1,5-a]pyrimidine | 17 |
| 62 | 7-hydroxy-5-methyl-6-(methylthio)-2-(3-(trifluoromethyl)phenyl)pyrazolo[1,5-a]pyrimidine | 26 |
| 63 | 2-(2,4-difluorophenyl)-7-hydroxy-5-methyl-6-(methylthio)pyrazolo[1,5-a]pyrimidine | 31 |

TABLE 7-continued

| Intermediate | Structure | Intermediate (starting material) |
|---|---|---|
| 64 | 2-(2-chlorophenyl)-7-hydroxy-6-(methylthio)-5-methylpyrazolo[1,5-a]pyrimidine | 20 |
| 65 | 2-(3,5-dichlorophenyl)-7-hydroxy-6-(methylthio)-5-methylpyrazolo[1,5-a]pyrimidine | 23 |
| 66 | 2-(2-chloro-4-(trifluoromethyl)phenyl)-7-hydroxy-6-(methylthio)-5-methylpyrazolo[1,5-a]pyrimidine | 28 |
| 67 | 2-(4-(trifluoromethyl)phenyl)-7-hydroxy-6-(methylthio)-5-methylpyrazolo[1,5-a]pyrimidine | 12 |
| 68 | 2-(2-fluoro-4-(trifluoromethyl)phenyl)-7-hydroxy-6-(methylthio)-5-methylpyrazolo[1,5-a]pyrimidine | 27 |
| 69 | 2-(2,4-dichlorophenyl)-7-hydroxy-6-(methylthio)-5-methylpyrazolo[1,5-a]pyrimidine | 21 |
| 70 | 2-(3-fluoro-4-(trifluoromethyl)phenyl)-7-hydroxy-6-(methylthio)-5-methylpyrazolo[1,5-a]pyrimidine | 35 |
| 71 | 2-(4-chloro-2-fluorophenyl)-7-hydroxy-6-(methylthio)-5-methylpyrazolo[1,5-a]pyrimidine | 34 |

TABLE 7-continued

| Intermediate | Structure | Intermediate (starting material) |
|---|---|---|
| 72 | (4-trifluoromethoxyphenyl)-pyrazolo[1,5-a]pyrimidine with 7-OH, 6-SCH₃, 5-CH₃ | 18 |
| 73 | (4-chlorophenyl)-pyrazolo[1,5-a]pyrimidine with 7-OH, 6-SCH₃, 5-CH₃ | 11 |
| 74 | (3,4-dichlorophenyl)-pyrazolo[1,5-a]pyrimidine with 7-OH, 6-SCH₃, 5-CH₃ | 22 |
| 75 | (4-chlorophenyl)-pyrazolo[1,5-a]pyrimidine with 7-OH, 6-SCH₃, 5-CH₃, 3-CH₃ | 16 |
| 76 | (3,4-difluorophenyl)-pyrazolo[1,5-a]pyrimidine with 7-OH, 6-SCH₃, 5-CH₃ | 29 |
| 77 | (2-fluorophenyl)-pyrazolo[1,5-a]pyrimidine with 7-OH, 6-SCH₃, 5-CH₃ | 30 |
| 78 | (4-ethoxyphenyl)-pyrazolo[1,5-a]pyrimidine with 7-OH, 6-SCH₃, 5-CH₃ | 24 |
| 79 | (4-cyanophenyl)-pyrazolo[1,5-a]pyrimidine with 7-OH, 6-SCH₃, 5-CH₃ | 25 |

TABLE 7-continued

| Intermediate | Structure | Intermediate (starting material) |
|---|---|---|
| 80 | 2-(4-chlorophenyl)-6-methoxy-5-methylpyrazolo[1,5-a]pyrimidin-7-ol | 11 |
| 81 | 2-(4-chlorophenyl)-5-methyl-6-(methylsulfinyl)pyrazolo[1,5-a]pyrimidin-7-ol | 11 |
| 82 | 2-(4-chlorophenyl)-5-methylpyrazolo[1,5-a]pyrimidin-7-ol | 11 |
| 83 | 2-(4-chlorophenyl)-6-ethoxy-5-methylpyrazolo[1,5-a]pyrimidin-7-ol | 11 |
| 84 | 2-(4-chlorophenyl)-5-methyl-6-(methylsulfonyl)pyrazolo[1,5-a]pyrimidin-7-ol | 11 |
| 85 | 6-ethyl-5-methyl-2-phenylpyrazolo[1,5-a]pyrimidin-7-ol | 15 |
| 86 | 2-(4-chlorophenyl)-6-(2-methoxyethyl)-5-methylpyrazolo[1,5-a]pyrimidin-7-ol | 11 |
| 87 | 2-(4-chlorophenyl)-6-isopropoxy-5-methylpyrazolo[1,5-a]pyrimidin-7-ol | 11 |
| 88 | 6-chloro-2-(4-chlorophenyl)-5-methylpyrazolo[1,5-a]pyrimidin-7-ol | 11 |

TABLE 7-continued

| Intermediate | Structure | Intermediate (starting material) |
|---|---|---|
| 89 | 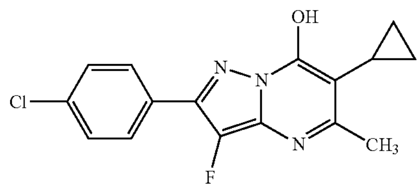 [SMILES: Cc1nc2c(F)c(-c3ccc(Cl)cc3)nn2c(O)c1C1CC1] | 38 |
| 90 | 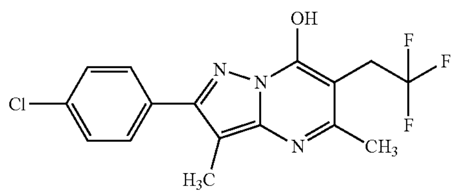 [SMILES: Cc1nc2c(C)c(-c3ccc(Cl)cc3)nn2c(O)c1CC(F)(F)F] | 16 |
| 91 | 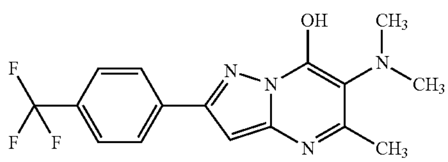 | 12 |
| 92 | 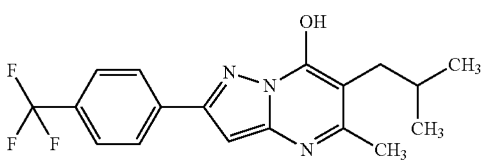 [SMILES: Cc1nc2cc(-c3ccc(C(F)(F)F)cc3)nn2c(O)c1CC(C)C] | 12 |
| 93 | 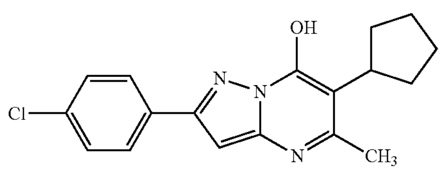 [SMILES: Cc1nc2cc(-c3ccc(Cl)cc3)nn2c(O)c1C1CCCC1] | 11 |
| 94 | 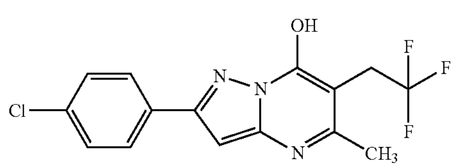 [SMILES: Cc1nc2cc(-c3ccc(Cl)cc3)nn2c(O)c1CC(F)(F)F] | 11 |
| 95 | 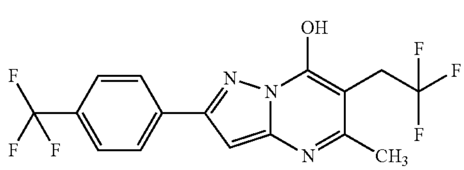 [SMILES: Cc1nc2cc(-c3ccc(C(F)(F)F)cc3)nn2c(O)c1CC(F)(F)F] | 12 |
| 96 | 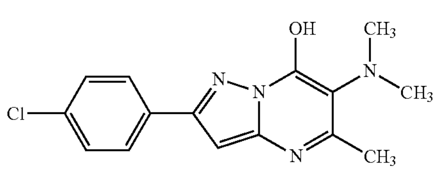 | 11 |

TABLE 7-continued

| Intermediate | Structure | Intermediate (starting material) |
|---|---|---|
| 97 | 2-(4-chlorophenyl)-6-(cyclopropylmethyl)-5-methylpyrazolo[1,5-a]pyrimidin-7-ol | 11 |
| 98 | 2-(4-chlorophenyl)-6-isobutyl-5-methylpyrazolo[1,5-a]pyrimidin-7-ol | 11 |
| 99 | 2-(4-chlorophenyl)-5-methyl-6-propylpyrazolo[1,5-a]pyrimidin-7-ol | 11 |
| 100 | 6-methoxy-5-methyl-2-(4-(trifluoromethyl)phenyl)pyrazolo[1,5-a]pyrimidin-7-ol | 12 |
| 101 | 2-(4-chlorophenyl)-6-ethyl-5-methylpyrazolo[1,5-a]pyrimidin-7-ol | 11 |
| 102 | 2-(4-chlorophenyl)-6-(isopropylthio)-5-methylpyrazolo[1,5-a]pyrimidin-7-ol | 11 |
| 103 | 2-(4-chlorophenyl)-3-methyl-5-methyl-6-(2,2,2-trifluoroethyl)pyrazolo[1,5-a]pyrimidin-7-ol | 16 |
| 104 | 2-(4-chlorophenyl)-6-cyclopropyl-5-methylpyrazolo[1,5-a]pyrimidin-7-ol | 11 |
| 105 | 3-fluoro-6-isopropyl-5-methyl-2-(2-fluoro-4-(trifluoromethyl)phenyl)pyrazolo[1,5-a]pyrimidin-7-ol | 36 |

TABLE 7-continued

| Intermediate | Structure | Intermediate (starting material) |
|---|---|---|
| 106 | 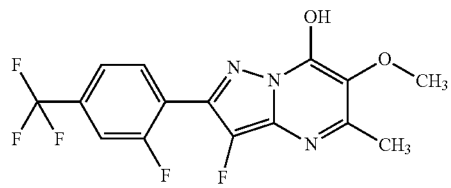 [SMILES: COc1c(C)nc2c(F)c(-c3ccc(C(F)(F)F)cc3F)nn2c1O] | 39 |
| 107 | 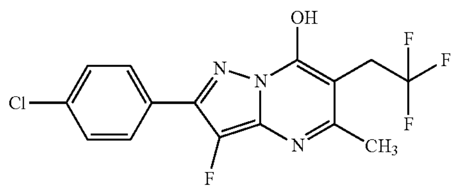 [SMILES: Cc1nc2c(F)c(-c3ccc(Cl)cc3)nn2c(O)c1CC(F)(F)F] | 38 |

(Structures for intermediates 106 and 107 shown in table.)

Example 1

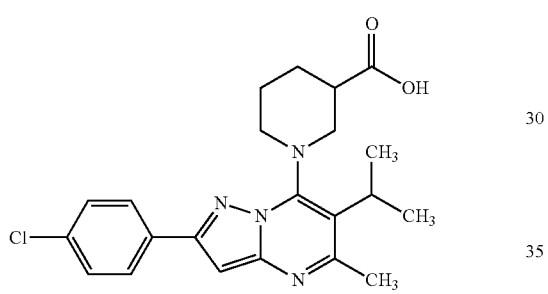

1-[2-(4-Chlorophenyl)-5-methyl-6-(propan-2-yl)pyrazolo[1,5-a]pyrimidin-7-yl]piperidine-3-carboxylic acid a) 7-Chloro-2-(4-chlorophenyl)-5-methyl-6-(propan-2-yl)pyrazolo[1,5-a]pyrimidine A mixture of 10.7 g (35.54 mmol) of 2-(4-chlorophenyl)-5-methyl-6-(propan-2-yl)pyrazolo[1,5-a]pyrimidin-7-ol (Intermediate 40), 16.22 mL (177 mmol) of phosphorus oxychloride, 9.87 mL (70.8 mmol) of triethylamine and 800 mL of toluene was refluxed for 20 h. The reaction mixture was cooled to 20° C., poured into a mixture of sodium hydrogen carbonate solution and ice, then stirred for 2 h. The reaction mixture was filtered, the filtrate was extracted with ethyl acetate, the combined organic layer was washed with water, dried over anhydrous sodium sulfate, filtered and concentrated in vacuo. The residue was chromatographed on silica gel eluting with ethylacetate and cyclohexane (2:1) to yield 7.75 g (68%) of the title compound. LC-MS (ESI) m/z 320.0 [MH$^+$]

b) 1-[2-(4-Chlorophenyl)-5-methyl-6-(propan-2-yl)pyrazolo[1,5-a]pyrimidin-7-yl]piperidine-3-carboxylic acid A mixture of 2.66 g (8.3 mmol) of 7-chloro-2-(4-chlorophenyl)-5-methyl-6-(propan-2-yl)pyrazolo[1,5-a]pyrimidine, 1.33 g (10.29 mmol) of nipecotic acid and 8.0 g (24.55 mmol) of cesium carbonate in 80 mL of N,N-dimethylformamide was heated at 110° C. for 5 h. The reaction mixture was cooled to 20° C., filtered. The filtrate was diluted with water, acidified with acetic acid and extracted with dichloromethane, the combined organic layer was washed with water, dried over anhydrous sodium sulfate, filtered and concentrated in vacuo. The residue was chromatographed on silica gel eluting with ethylacetate and cyclohexane (2:1) to yield 2.13 g (68%) of the title compound. LC-MS (ESI) m/z 413.1 [MH$^+$]

Example 2

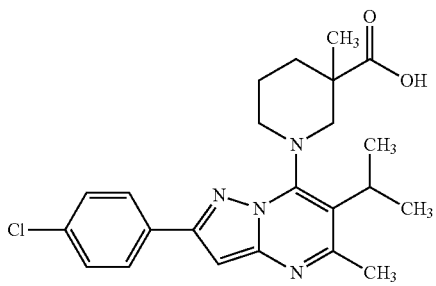

1-[2-(4-Chlorophenyl)-5-methyl-6-(propan-2-yl)pyrazolo[1,5-a]pyrimidin-7-yl]-3-methylpiperidine-3-carboxylic acid a) Ethyl 1-[2-(4-chlorophenyl)-5-methyl-6-(propan-2-yl)pyrazolo[1,5-a]pyrimidin-7-yl]-3-methylpiperidine-3-carboxylate A mixture of 2.0 g (6.23 mmol) of 7-chloro-2-(4-chlorophenyl)-5-methyl-6-(propan-2-yl)pyrazolo[1,5-a]pyrimidine (Example 1a), 1.5 g (8.34 mmol) of ethyl 3-methylpiperidine-3-carboxylate hydrochloride (Intermediate 1) and 3.5 mL (20.09 mmol) of N,N-diisopropylethylamine in 30 mL of N,N-dimethylformamide was heated at 120° C. for 20 h and concentrated in vacuo. The residue was triturated in isopropanol, the solid was filtered off, washed with isopropanol and dried to yield 2.5 g (88%) of the title compound. LC-MS (ESI) m/z 455.2 [MH$^+$]

b) 1-[2-(4-Chlorophenyl)-5-methyl-6-(propan-2-yl)pyrazolo[1,5-a]pyrimidin-7-yl]-3-methylpiperidine-3-carboxylic acid A mixture of 2.5 g (5.5 mmol) of ethyl 1-[2-(4-chlorophenyl)-5-methyl-6-(propan-2-yl) pyrazolo[1,5-a]pyrimidin-7-yl]-3-methylpiperidine-3-carboxylate and 10 mL of 20% sodium hydroxide solution in 50 mL of ethanol was refluxed for 24 h, then cooled and acidified with acetic acid. The precipitated crystals were filtered off, washed with water, dissolved in the mixture of dichloromethane-etanol. Activated carbon was added to the solution. The mixture was stirred. After filtration the dichloromethane was evaporated under reduced pressure. The precipitated crystals were filtered off and washed with etanol to yield 1.62 g (69.2%) of the title compound. LC-MS (ESI) m/z 427.2 [MH$^+$]

Example 3

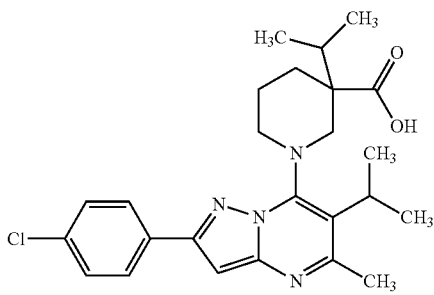 [SMILES: Cc1nc2cc(-c3ccc(Cl)cc3)nn2c(N2CCCC(C(=O)O)(C(C)C)C2)c1C(C)C]

1-[2-(4-Chlorophenyl)-5-methyl-6-(propan-2-yl)pyrazolo[1,5-a]pyrimidin-7-yl]-3-(propan-2-yl)piperidine-3-carboxylic acid A mixture of 0.95 g (4 mmol) of ethyl 3-(propan-2-yl)piperidine-3-carboxylate hydrochloride (Intermediate 3), 1.9 g (17 mmol) of potassium tert-butoxide in 19 mL of dimethyl sulfoxide was heated at 110° C. for 16 h. Then 1.29 g (4 mmol) of 7-chloro-2-(4-chlorophenyl)-5-methyl-6-(propan-2-yl)pyrazolo[1,5-a]pyrimidine (Example 1a), was added to the mixture and heated at 120° C. for 16 h. The reaction mixture was cooled and acidified with acetic acid. The precipitated crystals were filtered off, washed with water. The crude product was chromatographed on silica gel eluting with ethylacetate and cyclohexane (2:1), crystallized from isopropanol to yield 0.699 g (38%) of the title compound. LC-MS (ESI) m/z 455.2 [MH$^+$]

Example 4

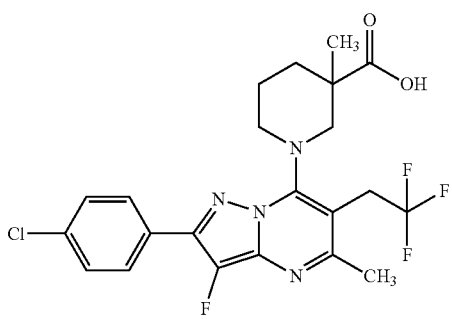 [SMILES: Cc1nc2c(F)c(-c3ccc(Cl)cc3)nn2c(N2CCCC(C)(C(=O)O)C2)c1CC(F)(F)F]

1-[2-(4-Chlorophenyl)-3-fluoro-5-methyl-6-(2,2,2-trifluoroethyl)pyrazolo[1,5-a]pyrimidin-7-yl]-3-methylpiperidine-3-carboxylic acid The title compound was prepared from 2-(4-chlorophenyl)-3-fluoro-5-methyl-6-(2,2,2-trifluoroethyl)pyrazolo[1,5-a]pyrimidin-7-ol (Intermediate 107), and ethyl 3-methylpiperidine-3-carboxylate hydrochloride (Intermediate 1) according to the method described in Example 2. LC-MS (ESI) m/z 485.2 [MH$^+$]

Example 5

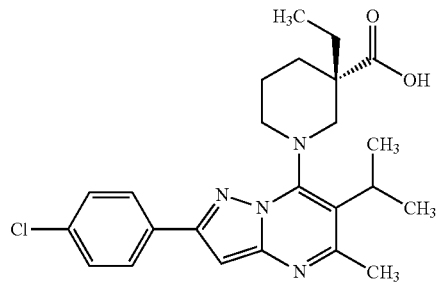 [SMILES: CC[C@]1(C(=O)O)CCCN(c2c(C(C)C)c(C)nc3cc(-c4ccc(Cl)cc4)nn23)C1]

(3S)-1-[2-(4-Chlorophenyl)-5-methyl-6-(propan-2-yl)pyrazolo[1,5-a]pyrimidin-7-yl]-3-ethylpiperidine-3-carboxylic acid a) Ethyl (3S)-1-[2-(4-chlorophenyl)-5-methyl-6-(propan-2-yl)pyrazolo[1,5-a]pyrimidin-7-yl]-3-ethylpiperidine-3-carboxylate A mixture of 1.2 g (3.74 mmol) of 7-chloro-2-(4-chlorophenyl)-5-methyl-6-(propan-2-yl)pyrazolo[1,5-a]pyrimidine (Example 1a), 1.5 g (8.34 mmol) of ethyl (3S)-3-ethylpiperidine-3-carboxylate hydrochloride and 3.5 mL (11.48 mmol) of N,N-diisopropylethylamine in 20 mL of N,N-dimethylformamide was heated at 120° C. for 20 h and concentrated in vacuo. The residue was chromatographed on silica gel eluting with ethylacetate and cyclohexane (2:1) to yield 1.5 g (87.7%) of the title compound. LC-MS (ESI) m/z 469.2 [MH$^+$]

b) (3S)-1-[2-(4-Chlorophenyl)-5-methyl-6-(propan-2-yl)pyrazolo[1,5-a]pyrimidin-7-yl]-3-ethylpiperidine-3-carboxylic acid A mixture of 1.5 g (3.2 mmol) of ethyl (3S)-1-[2-(4-chlorophenyl)-5-methyl-6-(propan-2-yl)pyrazolo[1,5-a]pyrimidin-7-yl]-3-ethylpiperidine-3-carboxylate and 10 mL of 20% sodium hydroxide solution in 50 mL of ethanol was refluxed for 24 h, then cooled and acidified with acetic acid. The precipitated crystals were filtered off and chromatographed on silica gel eluting with ethylacetate and cyclohexane (1:2) to yield 0.502 g (35.65%) of the title compound. LC-MS (ESI) m/z 441.2 [MH⁺]

Example 6

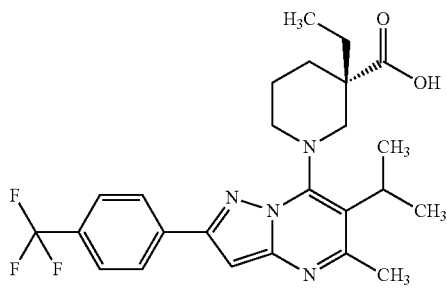 [SMILES: CC[C@]1(C(=O)O)CCCN(c2c(C(C)C)c(C)nc3cc(-c4ccc(C(F)(F)F)cc4)nn23)C1]

(3S)-3-Ethyl-1-[5-methyl-6-(propan-2-yl)-2-[4-(trifluoromethyl)phenyl]pyrazolo[1,5-a]pyrimidin-7-yl]piperidine-3-carboxylic acid a) 7-Chloro-5-methyl-6-(propan-2-yl)-2-[4-(trifluoromethyl)phenyl]pyrazolo[1,5-a]pyrimidine A mixture of 1 g (2.98 mmol) of 5-methyl-6-(propan-2-yl)-2-[4-(trifluoromethyl)phenyl]pyrazolo[1,5-a]pyrimidin-7-ol (Intermediate 41), 1.36 mL (14.8 mmol) of phosphorus oxychloride, 1.05 mL (6.02 mmol) of N,N-diisopropylethylamine and 35 mL of toluene was refluxed for 20 h. The reaction mixture was cooled to 20° C., poured into a mixture of sodium hydrogen carbonate solution and ice, then stirred for 2 h. The reaction mixture was filtered, the filtrate was extracted with ethyl acetate, the combined organic layer was washed with water, dried over anhydrous sodium sulfate, filtered and concentrated in vacuo to yield 0.94 g (89%) of the title compound. LC-MS (ESI) m/z 353.1 [MH⁺]

b) Ethyl (3S)-3-ethyl-1-[5-methyl-6-(propan-2-yl)-2-[4-(trifluoromethyl)phenyl]pyrazolo[1,5-a]pyrimidin-7-yl]piperidine-3-carboxylate A mixture of 1.4 g (3.96 mmol) of 7-chloro-5-methyl-6-(propan-2-yl)-2-[4-(trifluoromethyl)phenyl]pyrazolo[1,5-a]pyrimidine, 0.7 g (3.61 mmol) of ethyl (3S)-3-ethylpiperidine-3-carboxylate hydrochloride and 2 mL (11.4 mmol) of N,N-diisopropylethylamine in 25 mL of N,N-dimethylformamide was heated at 120° C. for 20 h and concentrated in vacuo. The residue was chromatographed on silica gel eluting with ethylacetate and cyclohexane (1:1) to yield 1.7 g (99%) of the title compound.

c) (3S)-3-Ethyl-1-[5-methyl-6-(propan-2-yl)-2-[4-(trifluoromethyl)phenyl]pyrazolo[1,5-a]pyrimidin-7-yl]piperidine-3-carboxylic acid A mixture of 1.7 g (3.38 mmol) of ethyl (3S)-3-ethyl-1-[5-methyl-6-(propan-2-yl)-2-[4-(trifluoromethyl)phenyl]pyrazolo[1,5-a]pyrimidin-7-yl]piperidine-3-carboxylate and 10 mL of 20% sodium hydroxide solution in 50 mL of ethanol was refluxed for 24 h, then cooled and acidified with acetic acid. The reaction mixture was extracted with dichloromethane, the combined organic layer was washed with water, dried over anhydrous sodium sulfate, filtered and concentrated in vacuo. The residue was chromatographed on silica gel eluting with ethylacetate and cyclohexane (1:2) to yield 0.666 g (41.4%) of the title compound. LC-MS (ESI) m/z 475.2 [MH⁺]

Example 7

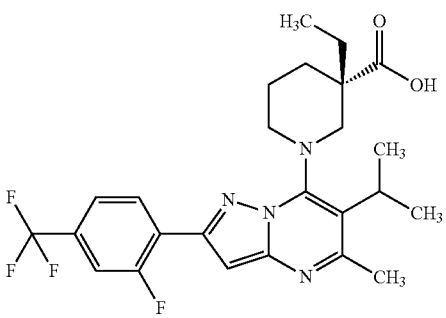 [SMILES: CC[C@]1(C(=O)O)CCCN(c2c(C(C)C)c(C)nc3cc(-c4ccc(C(F)(F)F)cc4F)nn23)C1]

(3S)-3-Ethyl-1-{2-[2-fluoro-4-(trifluoromethyl)phenyl]-5-methyl-6-(propan-2-yl)pyrazolo[1,5-a]pyrimidin-7-yl}piperidine-3-carboxylic acid a) 7-Chloro-2-[2-fluoro-4-(trifluoromethyl)phenyl]-5-methyl-6-(propan-2-yl)pyrazolo[1,5-a]pyrimidine A mixture of 3.667 g (10.38 mmol) of 2-[2-fluoro-4-(trifluoromethyl)phenyl]-5-methyl-6-(propan-2-yl)pyrazolo[1,5-a]pyrimidin-7-ol (Intermediate 44), 4.48 mL (52.67 mmol) of phosphorus oxychloride, 3.74 mL (21.44 mmol) of N,N-diisopropylethylamine and 280 mL of toluene was refluxed for 20 h. The reaction mixture was cooled to 20° C., poured into a mixture of sodium hydrogen carbonate solution and ice, then stirred for 2 h. The reaction mixture was filtered, the filtrate was extracted with ethyl acetate, the combined organic layer was washed with water, dried over anhydrous sodium sulfate, filtered and concentrated in vacuo. The residue was chromatographed on silica gel eluting with ethylacetate and cyclohexane (1:4) to to yield 2.41 g (62%) of the title compound. LC-MS (ESI) m/z 372.1 [MH+]

b) Ethyl (3S)-3-ethyl-1-{2-[2-fluoro-4-(trifluoromethyl)phenyl]-5-methyl-6-(propan-2-yl)pyrazolo[1,5-a]pyrimidin-7-yl}piperidine-3-carboxylate A mixture of 0.93 g (2.55 mmol) of 7-chloro-2-[2-fluoro-4-(trifluoromethyl)phenyl]-5-methyl-6-(propan-2-yl)pyrazolo[1,5-a]pyrimidine, 0.484 g (2.55 mmol) of ethyl (3S)-3-ethylpiperidine-3-carboxylate hydrochloride and 1.6 mL (9.18 mmol) of N,N-diisopropylethylamine in 20 mL of N,N-dimethylformamide was heated at 120° C. for 20 h, then cooled and acidified with 2M hydrochloric acid. The reaction mixture was extracted with ethylacetate, the combined organic layer was washed with water, dried over anhydrous sodium sulfate, filtered and concentrated in vacuo. The residue was chromatographed on silica gel eluting with ethylacetate and cyclohexane (1:1) to yield 0.753 g (58%) of the title compound.

c) (3S)-3-Ethyl-1-{2-[2-fluoro-4-(trifluoromethyl)phenyl]-5-methyl-6-(propan-2-yl)pyrazolo[1,5-a]pyrimidin-7-yl}piperidine-3-carboxylic acid A mixture of 0.753 g (1.44 mmol) of ethyl (3S)-3-ethyl-1-(2-[2-fluoro-4-(trifluoromethyl)phenyl]-5-methyl-6-(propan-2-yl)pyrazolo[1,5-a]pyrimidin-7-yl) piperidine-3-carboxylate and 10 mL of 4 M sodium hydroxide solution in 50 mL of ethanol was refluxed for 24 h, then cooled and acidified with acetic acid. The reaction mixture was extracted with ethylacetate, the combined organic layer was washed with water, dried over anhydrous sodium sulfate, filtered and concentrated in vacuo. The residue was chromatographed on silica gel eluting with ethylacetate and cyclohexane (1:1) to yield 0.277 g (39%) of the title compound.

LC-MS (ESI) m/z 493.3 [MH+]

Example 8

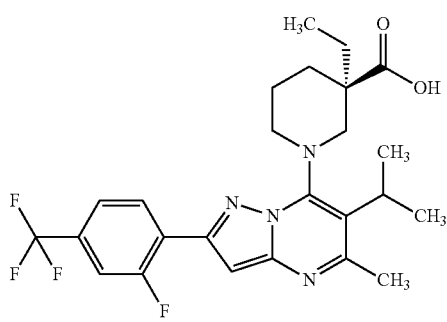 [SMILES: CC[C@@]1(C(=O)O)CCCN(c2c(C(C)C)c(C)nc3cc(-c4ccc(C(F)(F)F)cc4F)nn23)C1]

(3R)-3-Ethyl-1-{2-[2-fluoro-4-(trifluoromethyl)phenyl]-5-methyl-6-(propan-2-yl)pyrazolo[1,5-a]pyrimidin-7-yl}piperidine-3-carboxylic acid a) Ethyl (3R)-3-ethyl-1-{2-[2-fluoro-4-(trifluoromethyl)phenyl]-5-methyl-6-(propan-2-yl)pyrazolo[1,5-a]pyrimidin-7-yl}piperidine-3-carboxylate A mixture of 0.93 g (2.5 mmol) of 7-chloro-2-[2-fluoro-4-(trifluoromethyl)phenyl]-5-methyl-6-(propan-2-yl)pyrazolo[1,5-a]pyrimidine (Example 7a), 0.375 g (2.02 mmol) of ethyl (3R)-3-ethylpiperidine-3-carboxylate and 1.6 mL (9.18 mmol) of N,N-diisopropylethylamine in 20 mL of N,N-dimethylformamide was heated at 120° C. for 20 h, then cooled and acidified with 2M hydrochloric acid. The reaction mixture was extracted with ethylacetate, the combined organic layer was washed with water, dried over anhydrous sodium sulfate, filtered and concentrated in vacuo. The residue was chromatographed on silica gel eluting with ethylacetate and cyclohexane (1:1) to yield 0.618 g (58%) of the title compound.

b) 3R)-3-Ethyl-1-{2-[2-fluoro-4-(trifluoromethyl)phenyl]-5-methyl-6-(propan-2-yl)pyrazolo[1,5-a]pyrimidin-7-yl}piperidine-3-carboxylic acid A mixture of 0.618 g (1.19 mol) of ethyl (3R)-3-ethyl-1-{2-[2-fluoro-4-(trifluoromethyl)phenyl]-5-methyl-6-(propan-2-yl)pyrazolo[1,5-a]pyrimidin-7-yl}piperidine-3-carboxylate and 10 mL of 4 M sodium hydroxide solution in 50 mL of ethanol was refluxed for 24 h, then cooled and acidified with acetic acid. The reaction mixture was extracted with ethylacetate, the combined organic layer was washed with water, dried over anhydrous sodium sulfate, filtered and concentrated in vacuo. The residue was chromatographed on silica gel eluting with ethylacetate and cyclohexane (1:1) to yield 0.173 g (29%) of the title compound. LC-MS (ESI) m/z 493.3 [MH+]

Example 9

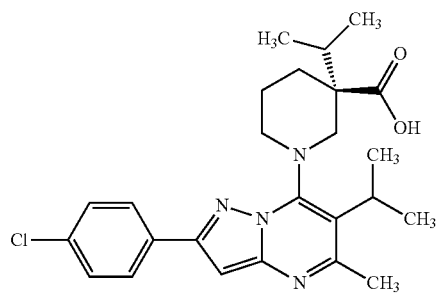

(3S)-1-[2-(4-Chlorophenyl)-5-methyl-6-(propan-2-yl)pyrazolo[1,5-a]pyrimidin-7-yl]-3-(propan-2-yl)piperidine-3-carboxylic acid A mixture of 0.3 g (1.26 mmol) of ethyl (3S)-3-(propan-2-yl)piperidine-3-carboxylate hydrochloride, 0.3 g (2.67 mmol) of potassium tert-butoxide in 10 mL of dimethyl sulfoxide was heated at 100° C. for 16 h. Then 0.41 g (1.28 mmol) 7-chloro-2-(4-chlorophenyl)-5-methyl-6-(propan-2-yl)pyrazolo[1,5-a]pyrimidine (Example 1a), was added to the mixture and heated at 120° C. for 16 h. The reaction mixture was cooled and acidified with acetic acid. The precipitated crystals were filtered off, washed with water. The crude product was chromatographed on silica gel eluting with ethylacetate and cyclohexane (1:2) to yield 0.33 g (57%/o) of the title compound. LC-MS (ESI) m/z 455.2 [MH+]

Example 10

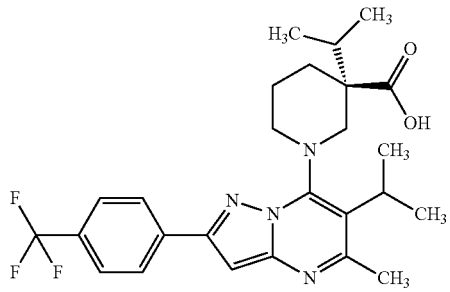 [SMILES: Cc1nc2cc(-c3ccc(C(F)(F)F)cc3)nn2c(N2CCC[C@](C(=O)O)(C(C)C)C2)c1C(C)C]

(3S)-1-[5-Methyl-6-(propan-2-yl)-2-[4-(trifluoromethyl)phenyl]pyrazolo[1,5-a]pyrimidin-7-yl]-3-(propan-2-yl)piperidine-3-carboxylic acid A mixture of 0.3 g (1.26 mmol) of ethyl (3S)-3-(propan-2-yl)piperidine-3-carboxylate hydrochloride, 0.3 g (2.67 mmol) of potassium tert-butoxide in 10 mL of dimethyl sulfoxide was heated at 100° C. for 16 h. Then 0.45 g (1.27 mmol) 7-chloro-5-methyl-6-(propan-2-yl)-2-[4-(trifluoromethyl)phenyl]pyrazolo[1,5-a]pyrimidine (Example 6a), was added to the mixture and heated at 120° C. for 16 h. The reaction mixture was cooled and acidified with acetic acid.

The precipitated crystals were filtered off, washed with water. The crude product was chromatographed on silica gel eluting with ethylacetate and cyclohexane (1:2) to yield 0.31 g (51%) of the title compound. LC-MS (ESI) m/z 489.2 [MH+]

Example 11

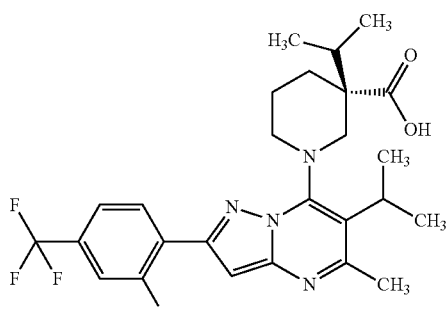

(3R)-1-{2-[2-Fluoro-4-(trifluoromethyl)phenyl]-5-methyl-6-(propan-2-yl)pyrazolo[1,5-a]pyrimidin-7-yl}-3-(propan-2-yl)piperidine-3-carboxylic acid A mixture of 0.236 g of ethyl (3R)-3-(propan-2-yl)piperidine-3-carboxylate hydrochloride (1 mmol), 0.236 g (2.1 mmol) of potassium tert-butoxide in 8 mL of dimethyl sulfoxide was heated at 100° C. for 16 h. Then 0.40 g (1.08 mmol) 7-chloro-5-methyl-6-(propan-2-yl)-2-[4-(trifluoromethyl)phenyl]pyrazolo[1,5-a]pyrimidine (Example 7a) was added to the mixture and heated at 120° C. for 16 h. The reaction mixture was cooled and acidified with acetic acid. The precipitated crystals were filtered off, washed with water. The crude product was chromatographed on silica gel eluting with ethylacetate and cyclohexane (1:2) to yield 0.237 g (46%) of the title compound. LC-MS (ESI) m/z 507.3 [MH+]

Example 12

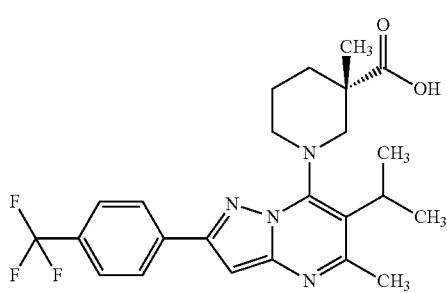

(3S)-3-Methyl-1-[5-methyl-6-(propan-2-yl)-2-[4-(trifluoromethyl)phenyl]pyrazolo[1,5-a]pyrimidin-7-yl]piperidine-3-carboxylic acid a) Ethyl (3S)-3-methyl-1-[5-methyl-6-(propan-2-yl)-2-[4-(trifluoromethyl)phenyl]pyrazolo[1,5-a]pyrimidin-7-yl]piperidine-3-carboxylate A mixture of 0.354 g (1 mmol) of 7-chloro-5-methyl-6-(propan-2-yl)-2-[4-(trifluoromethyl)phenyl]pyrazolo[1,5-a]pyrimidine (Example 6a), 0.249 g (1.2 mmol) of ethyl (3S)-3-methylpiperidine-3-carboxylate hydrochloride and 0.52 mL (3 mmol) of N,N-diisopropylethylamine in 5 mL of N,N-dimethylformamide was heated at 120° C. for 20 h and concentrated in vacuo. The residue was chromatographed on silica gel eluting with dichloromethane to yield 0.30 g (61%/o) of the title compound.

b) (3S)-3-Methyl-1-[5-methyl-6-(propan-2-yl)-2-[4-(trifluoromethyl)phenyl]pyrazolo[1,5-a]pyrimidin-7-yl]piperidine-3-carboxylic acid A mixture of 0.3 g (0.61 mmol) of ethyl (3S)-3-methyl-1-[5-methyl-6-(propan-2-yl)-2-[4-(trifluoromethyl)phenyl]pyrazolo[1,5-a]pyrimidin-7-yl]piperidine-3-carboxylate and 2 mL of 20% sodium hydroxide solution in 10 mL of ethanol was refluxed for 24 h, then cooled and acidified with acetic acid. The reaction mixture was extracted with ethylacetate, the combined organic layer was washed with water, dried over anhydrous magnesium sulfate, filtered and concentrated in vacuo. The residue was chromatographed on silica gel eluting with dichloromethane-methanol-ammonia (10:1: 0.1) to yield 0.127 g (44.9%) of the title compound. LC-MS (ESI) m/z 461.3 [MH+]

Example 13

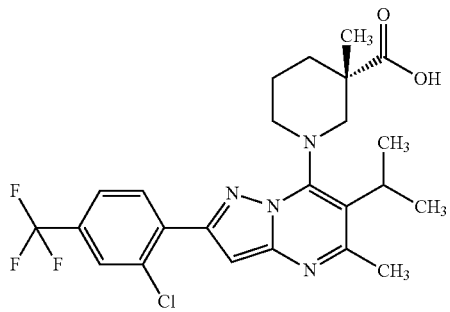 [SMILES: Cc1nc2cc(-c3ccc(C(F)(F)F)cc3Cl)nn2c(N2CCC[C@](C)(C(=O)O)C2)c1C(C)C]

(3S)-1-{2-[2-Chloro-4-(trifluoromethyl)phenyl]-5-methyl-6-(propan-2-yl)pyrazolo[1,5-a]pyrimidin-7-yl}-3-methylpiperidine-3-carboxylic acid a) 7-Chloro-2-[2-chloro-4-(trifluoromethyl)phenyl]-5-methyl-6-(propan-2-yl)pyrazolo[1,5-a]pyrimidine A mixture of 8.99 g (24.3 mmol) of 2-[2-chloro-4-(trifluoromethyl)phenyl]-5-methyl-6-(propan-2-yl)pyrazolo[1,5-a]pyrimidin-7-ol (Intermediate 42), 11 mL (118 mmol) of phosphorus oxychloride, 8.5 mL (48.7 mmol) of N,N-diisopropylethylamine and 250 mL of toluene was refluxed for 48 h. The reaction mixture was cooled to 20° C., poured into a mixture of sodium hydrogen carbonate solution and ice, then stirred for 2 h. The reaction mixture was filtered, the filtrate was extracted with ethyl acetate, the combined organic layer was washed with water, dried over anhydrous sodium sulfate, filtered and concentrated in vacuo to yield 6.78 g (71%) of the title compound.

b) Ethyl (3S)-1-{2-[2-chloro-4-(trifluoromethyl)phenyl]-5-methyl-6-(propan-2-yl)pyrazolo[1,5-a]pyrimidin-7-yl}-3-methylpiperidine-3-carboxylate A mixture of 2.586 g (6.66 mmol) of 7-chloro-2-[2-chloro-4-(trifluoromethyl)phenyl]-5-methyl-6-(propan-2- yl)pyrazolo[1,5-a]pyrimidine, 1.36 g (6.54 mmol) of ethyl (3S)-3-methylpiperidine-3-carboxylate hydrochloride and 3.6 mL (20.66 mmol) of N,N-diisopropylethylamine in 35 mL of N,N-dimethylformamide was heated at 120° C. for 20 h and concentrated in vacuo. The residue was chromatographed on silica gel eluting with ethylacetate and cyclohexane (1:4) to give the title compound.

c) (3S)-1-{2-[2-Chloro-4-(trifluoromethyl)phenyl]-5-methyl-6-(propan-2-yl)pyrazolo[1,5-a]pyrimidin-7-yl}-3-methylpiperidine-3-carboxylic acid The above obtained ethyl (3S)-1-{2-[2-chloro-4-(trifluoromethyl)phenyl]-5-methyl-6-(propan-2-yl)pyrazolo[1,5-a]pyrimidin-7-yl}-3-methylpiperidine-3-carboxylate was solved in 60 ml of ethanol and 12 ml (48 mmol) of 4M sodium hydroxide solution was added. The reaction mixture was refluxed for 24 h, then cooled and acidified with acetic acid. The precipitated crystals were filtered off, washed with water. The crude product was chromatographed on silica gel eluting with ethylacetate and cyclohexane (2:1) to yield 2.011 g (61%) of the title compound. LC-MS (ESI) m/z 495.3 [MH+]

Example 14

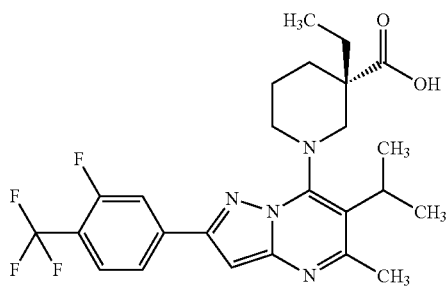 [SMILES: CC[C@]1(C(=O)O)CCCN(c2c(C(C)C)c(C)nc3cc(-c4ccc(C(F)(F)F)c(F)c4)nn23)C1]

(3S)-3-Ethyl-1-{2-[3-fluoro-4-(trifluoromethyl)phenyl]-5-methyl-6-(propan-2-yl)pyrazolo[1,5-al a]pyrimidin-7-yl}piperidine-3-carboxylic acid a) 7-Chloro-2-[3-fluoro-4-(trifluoromethyl)phenyl]-5-methyl-6-(propan-2-yl)pyrazolo[1,5-a]pyrimidine A mixture of 21.19 g (60 mmol) of 2-[3-fluoro-4-(trifluoromethyl)phenyl]-5-methyl-6-(propan-2-yl)pyrazolo[1,5-a]pyrimidin-7-ol (Intermediate 45), 27.5 mL (300 mmol) of phosphorus oxychloride, 20.9 mL (120 mmol) of N,N-diisopropylethylamine and 730 mL of toluene was refluxed for 24 h. The reaction mixture was cooled to 20° C., poured into a mixture of sodium hydrogen carbonate solution and ice, then stirred for 2 h. The reaction mixture was extracted with ethyl acetate, the combined organic layer was washed with water, dried over anhydrous sodium sulfate, filtered and concentrated in vacuo. The residue was treated with isopropanol. The precipitated product was filtered off to yield 19.2 g (86%) of the title compound.

b) (3S)-3-Ethyl-1-{2-[3-fluoro-4-(trifluoromethyl)phenyl]-5-methyl-6-(propan-2-yl)pyrazolo[1,5-a]pyrimidin-7-yl}piperidine-3-carboxylic acid A mixture of 0.22 g (1 mmol) of ethyl (3S)-3-methylpiperidine-3-carboxylate hydrochloride, 0.23 g (2.1 mmol) of potassium tert-butoxide in 5 mL of dimethyl sulfoxide was heated at 100° C. for 16 h. Then 0.37 g (1 mmol) 7-chloro-2-[3-fluoro-4-(trifluoromethyl)phenyl]-5-methyl-6-(propan-2-yl)pyrazolo[1,5-a]pyrimidine was added to the mixture and heated at 100° C. for 7 h. The reaction mixture was cooled and acidified with acetic acid. The precipitated crystals were filtered off, washed with water. The crude product was chromatographed on silica gel eluting with ethylacetate and cyclohexane (1:2) to yield 0.19 g (40%) of the title compound. LC-MS (ESI) m/z 493.3 [MH+]

Example 15

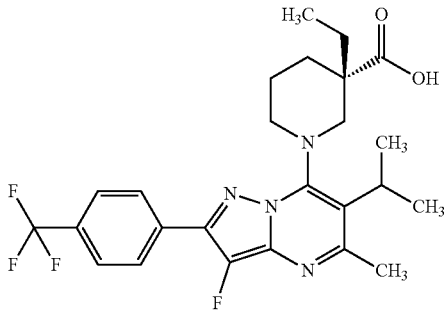 [SMILES: CC[C@]1(C(=O)O)CCCN(c2c(C(C)C)c(C)nc3c(F)c(-c4ccc(C(F)(F)F)cc4)nn23)C1]

(3S)-3-Ethyl-1-[3-fluoro-5-methyl-6-(propan-2-yl)-2-[4-(trifluoromethyl)phenyl]pyrazolo[1,5-a]pyrimidin-7-yl]piperidine-3-carboxylic acid a) 7-Chloro-3-fluoro-5-methyl-6-(propan-2-yl)-2-[4-(trifluoromethyl)phenyl]pyrazolo[1,5-a]pyrimidine A mixture of 2.97 g (8.4 mmol) of 3-fluoro-5-methyl-6-(propan-2-yl)-2-[4-(trifluoromethyl)phenyl]pyrazolo[1,5-a]pyrimidin-7-ol (Intermediate 47), 3.9 mL (42.6 mmol) of phosphorus oxychloride, 3 mL (17.2 mmol) of N,N-diisopropylethylamine and 150 mL of toluene was refluxed for 24 h. The reaction mixture was cooled to 20° C., poured into a mixture of sodium hydrogen carbonate solution and ice, then stirred for 2 h. The reaction mixture was extracted with ethyl acetate, the combined organic layer was washed with water, dried over anhydrous sodium sulfate, filtered and concentrated in vacuo to yield 2.9 g (93%0) of the title compound. LC-MS (ESI) m/z 372.0 [MH+]

b) Ethyl (3S)-3-ethyl-1-[3-fluoro-5-methyl-6-(propan-2-yl)-2-[4-(trifluoromethyl)phenyl]pyrazolo[1,5-a]pyrimidin-7-yl]piperidine-3-carboxylate A mixture of 0.53 g (1.4 mmol) of 7-chloro-3-fluoro-5-methyl-6-(propan-2-yl)-2-[4-(trifluoromethyl)phenyl]pyrazolo[1,5-a]pyrimidine, 0.35 g (1.58 mmol) of ethyl (3S)-3-ethylpiperidine-3-carboxylate hydrochloride and 0.7 mL (4 mmol) of N,N-diisopropylethylamine in 10 mL of N,N-dimethylformamide was heated at 120° C. for 20 h and concentrated in vacuo. The residue was chromatographed on silica gel eluting with dichloromethane to give the title compound.

c) (3S)-3-Ethyl-1-[3-fluoro-5-methyl-6-(propan-2-yl)-2-[4-(trifluoromethyl)phenyl]pyrazolo[1,5-a]pyrimidin-7-yl]piperidine-3-carboxylic acid The above obtained ethyl (3S)-3-ethyl-1-[3-fluoro-5-methyl-6-(propan-2-yl)-2-[4-(trifluoromethyl)phenyl]pyrazolo[1,5-a]pyrimidin-7-yl]piperidine-3-carboxylate was solved in 15 ml of ethanol and 4 ml (24 mmol) of 20% sodium hydroxide solution was added. The reaction mixture was refluxed for 24 h, then cooled and acidified with acetic acid. The reaction mixture was extracted with ethylacetate, the combined organic layer was washed with water, dried over anhydrous sodium sulfate, filtered and concentrated in vacuo. The residue was chromatographed on silica gel eluting with ethylacetate and cyclohexane (1:2) to yield 0.26 g (37%) of the title compound. LC-MS (ESI) m/z 493.2 [MH$^+$]

Example 16

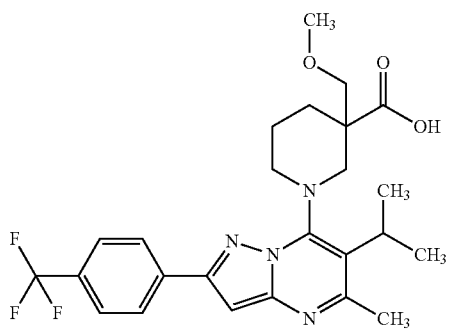

3-(Methoxymethyl)-1-[5-methyl-6-(propan-2-yl)-2-[4-(trifluoromethyl)phenyl]pyrazolo[1,5-a]pyrimidin-7-yl]piperidine-3-carboxylic acid A mixture of 0.8 g (3.36 mmol) of ethyl 3-(methoxymethyl)piperidine-3-carboxylate hydrochloride, 0.78 g (6.96 mmol) of potassium tert-butoxide in 10 mL of dimethyl sulfoxide was heated at 100° C. for 6 h. Then 0.8 g (2.26 mmol) 7-chloro-5-methyl-6-(propan-2-yl)-2-[4-(trifluoromethyl)phenyl]pyrazolo[1,5-a]pyrimidine (Example 6a), was added to the mixture and heated at 120° C. for 16 h. The reaction mixture was cooled, acidified with acetic acid and diluted with water. The precipitated crystals were filtered off, washed with water. The crude product was chromatographed on silica gel eluting with ethylacetate and cyclohexane (2:1) to yield 0.355 g (21%) of the title compound. LC-MS (ESI) m/z 491.1 [MH$^+$]

Example 17

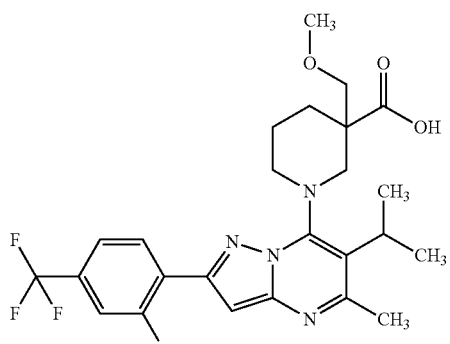

1-{2-[2-Fluoro-4-(trifluoromethyl)phenyl]-5-methyl-6-(propan-2-yl)pyrazolo[1,5-a]pyrimidin-7-yl}-3-(methoxymethyl)piperidine-3-carboxylic acid a) Ethyl 1-{2-[2-fluoro-4-(trifluoromethyl)phenyl]-5-methyl-6-(propan-2-yl)pyrazolo[1,5-a]pyrimidin-7-yl}-3-(methoxymethyl)piperidine-3-carboxylate A mixture of 1.00 g (2.69 mmol) of 7-chloro-2-[2-fluoro-4-(trifluoromethyl)phenyl]-5-methyl-6-(propan-2-yl)pyrazolo[1,5-a]pyrimidine (Example 7a), 0.70 g (2.94 mmol) of ethyl 3-(methoxymethyl)piperidine-3-carboxylate hydrochloride (Intermediate 4) and 1.2 mL (6.89 mmol) of N,N-diisopropylethylamine in 20 mL of N,N-dimethylformamide was heated at 120° C. for 20 h, and concentrated in vacuo. The residue was chromatographed on silica gel eluting with dichloromethane to yield 0.954 g (66%) of the title compound.
LC-MS (ESI) m/z 537.1 [MH$^+$]

b) 1-{2-[2-Fluoro-4-(trifluoromethyl)phenyl]-5-methyl-6-(propan-2-yl)pyrazolo[1,5-a]pyrimidin-7-yl}-3-(methoxymethyl)piperidine-3-carboxylic acid A mixture of 0.904 g (1.68 mmol) of ethyl 1-{2-[2-fluoro-4-(trifluoromethyl)phenyl]-5-methyl-6-(propan-2-yl)pyrazolo[1,5-a]pyrimidin-7-yl}-3-(methoxymethyl)piperidine-3-carboxylate and 0.723 g (17.23 mmol) of lithium hydroxide monohydrate in a mixture of 7 mL of tetrahydrofuran and 7 mL of water was refluxed for 72 h. The reaction mixture was cooled, acidified with acetic acid, diluted with water and extracted with ethylacetate. The combined organic layer was washed with water, dried over anhydrous sodium sulfate, filtered and concentrated in vacuo to yield 0.471 g (52%) of the title compound. LC-MS (ESI) m/z 509.1 [MH$^+$]

Examples 18-170 were prepared using analogues methods to those Examples described above and are exemplified below in Table 8.

TABLE 8

| Example | Structure | LC-MS (ESI) m/z [MH+] | Intermediate |
|---|---|---|---|
| 18 | 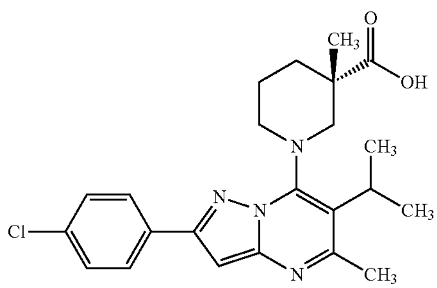 [SMILES: Cc1nc2cc(-c3ccc(Cl)cc3)nn2c(N2CCC[C@](C)(C(=O)O)C2)c1C(C)C] | 427.2 | 40 |
| 19 | 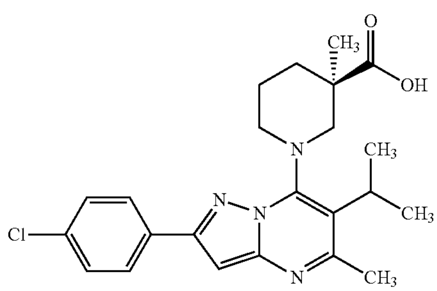 [SMILES: Cc1nc2cc(-c3ccc(Cl)cc3)nn2c(N2CCC[C@@](C)(C(=O)O)C2)c1C(C)C] | 427.2 | 40 |
| 20 | 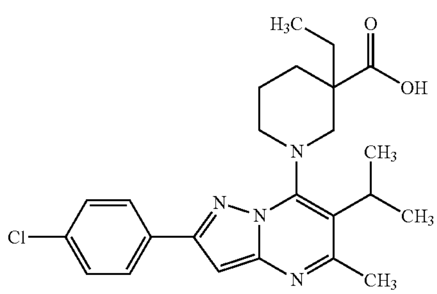 [SMILES: CCC1(C(=O)O)CCCN(c2c(C(C)C)c(C)nc3cc(-c4ccc(Cl)cc4)nn23)C1] | 441.2 | 40 |
| 21 | 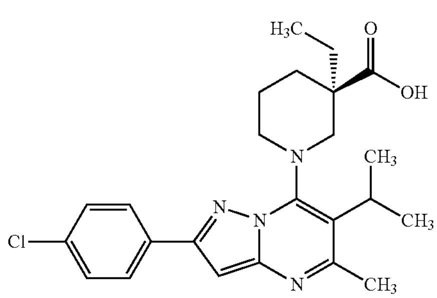 [SMILES: CC[C@@]1(C(=O)O)CCCN(c2c(C(C)C)c(C)nc3cc(-c4ccc(Cl)cc4)nn23)C1] | 441.2 | 40 |
| 22 | 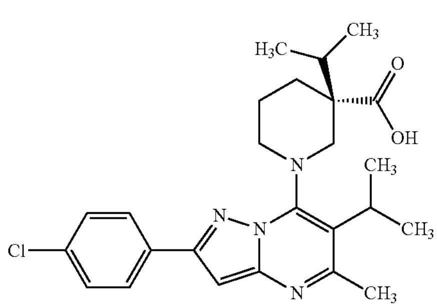 [SMILES: Cc1nc2cc(-c3ccc(Cl)cc3)nn2c(N2CCC[C@@](C(=O)O)(C(C)C)C2)c1C(C)C] | 455.2 | 40 |

TABLE 8-continued

| Example | Structure | LC-MS (ESI) m/z [MH+] | Intermediate |
|---|---|---|---|
| 23 | 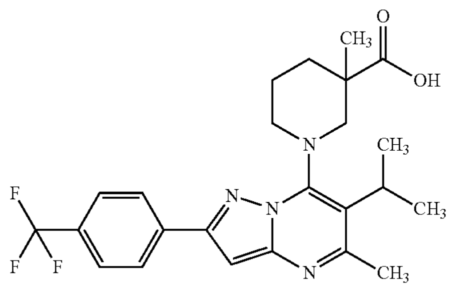 [SMILES: Cc1nc2cc(-c3ccc(C(F)(F)F)cc3)nn2c(N2CCCC(C)(C(=O)O)C2)c1C(C)C] | 461.3 | 41 |
| 24 | 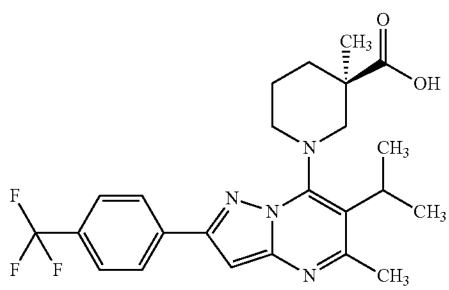 [SMILES: Cc1nc2cc(-c3ccc(C(F)(F)F)cc3)nn2c(N2CCC[C@@](C)(C(=O)O)C2)c1C(C)C] | 461.3 | 41 |
| 25 | 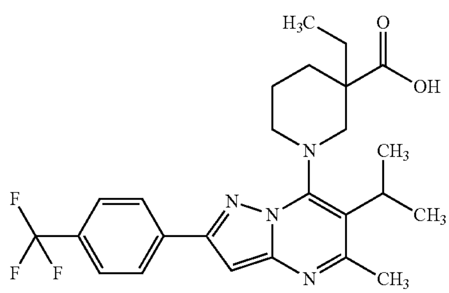 [SMILES: CCC1(C(=O)O)CCCN(c2c(C(C)C)c(C)nc3cc(-c4ccc(C(F)(F)F)cc4)nn23)C1] | 475.3 | 41 |
| 26 | 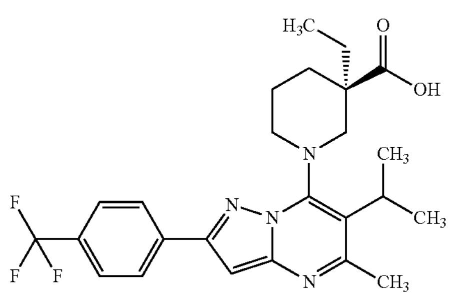 [SMILES: CC[C@@]1(C(=O)O)CCCN(c2c(C(C)C)c(C)nc3cc(-c4ccc(C(F)(F)F)cc4)nn23)C1] | 475.3 | 41 |
| 27 | 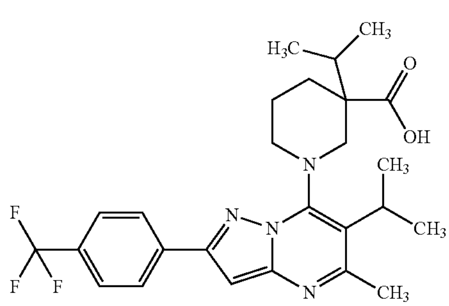 [SMILES: Cc1nc2cc(-c3ccc(C(F)(F)F)cc3)nn2c(N2CCCC(C(=O)O)(C(C)C)C2)c1C(C)C] | 489.2 | 41 |

TABLE 8-continued

| Example | Structure | LC-MS (ESI) m/z [MH+] | Intermediate |
|---|---|---|---|
| 28 | 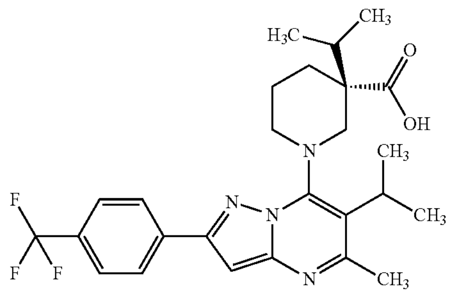 [SMILES: Cc1nc2cc(-c3ccc(C(F)(F)F)cc3)nn2c(N2CCC[C@@](C(=O)O)(C(C)C)C2)c1C(C)C] | 489.2 | 41 |
| 29 | 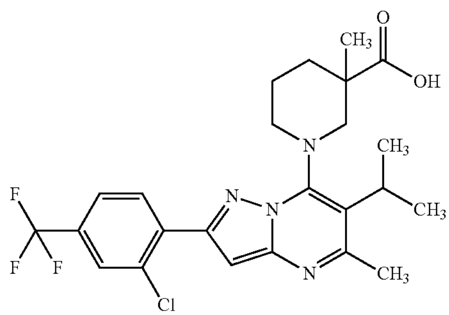 [SMILES: Cc1nc2cc(-c3ccc(C(F)(F)F)cc3Cl)nn2c(N2CCCC(C)(C(=O)O)C2)c1C(C)C] | 495.2 | 42 |
| 30 | 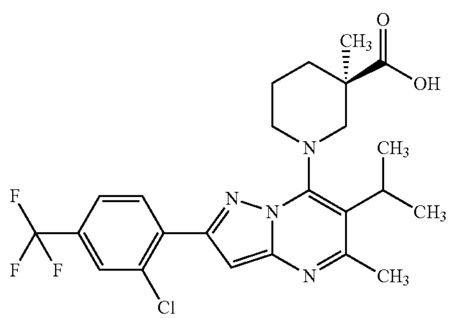 | 495.1 | 42 |
| 31 | 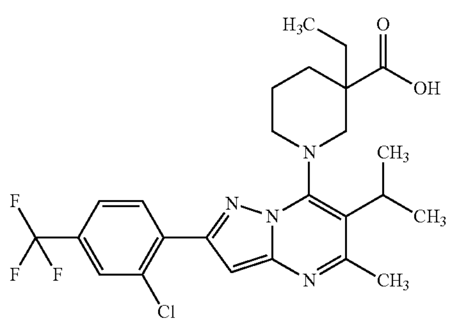 [SMILES: CCC1(C(=O)O)CCCN(c2c(C(C)C)c(C)nc3cc(-c4ccc(C(F)(F)F)cc4Cl)nn23)C1] | 509.2 | 42 |
| 32 | 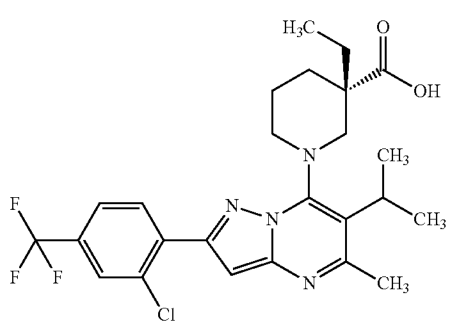 | 509.2 | 42 |

TABLE 8-continued

| Example | Structure | LC-MS (ESI) m/z [MH+] | Intermediate |
|---|---|---|---|
| 33 | 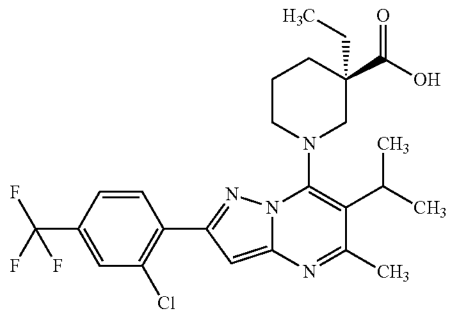 | 509.2 | 42 |
| 34 | 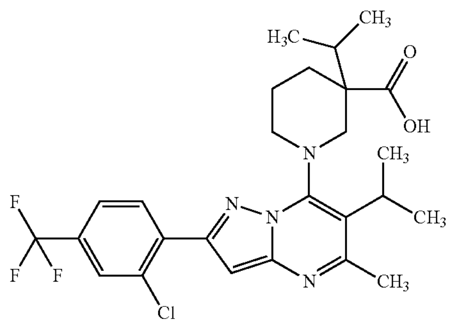 | 523.2 | 42 |
| 35 | 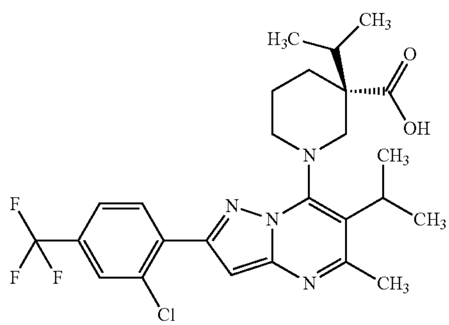 [SMILES: Cc1nc2cc(-c3ccc(C(F)(F)F)cc3Cl)nn2c(N2CCC[C@@](C(=O)O)(C(C)C)C2)c1C(C)C] | 523.2 | 42 |
| 36 | 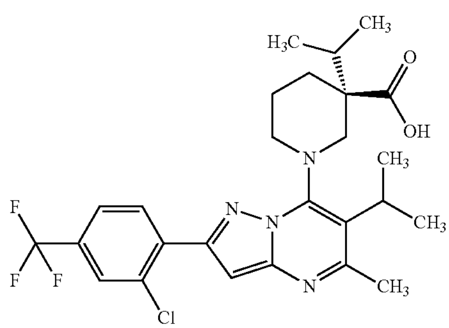 | 523.2 | 42 |
| 37 | 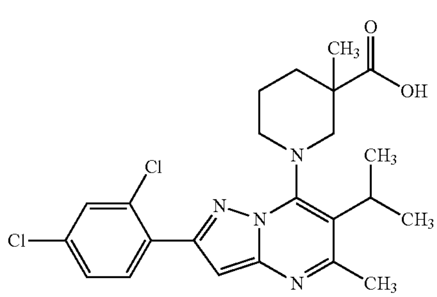 [SMILES: Cc1nc2cc(-c3ccc(Cl)cc3Cl)nn2c(N2CCCC(C)(C(=O)O)C2)c1C(C)C] | 461.1 | 43 |

TABLE 8-continued

| Example | Structure | LC-MS (ESI) m/z [MH+] | Intermediate |
|---|---|---|---|
| 38 | 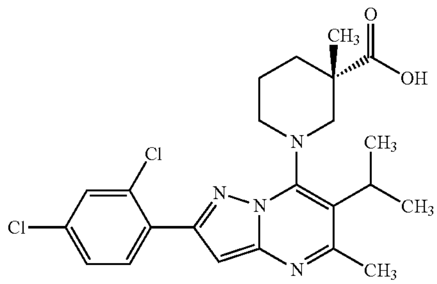 [SMILES: Cc1nc2cc(-c3ccc(Cl)cc3Cl)nn2c(N2CCC[C@](C)(C(=O)O)C2)c1C(C)C] | 461.2 | 43 |
| 39 | 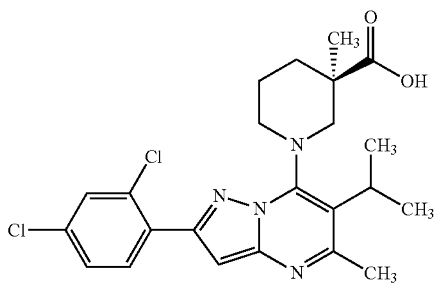 [SMILES: Cc1nc2cc(-c3ccc(Cl)cc3Cl)nn2c(N2CCC[C@@](C)(C(=O)O)C2)c1C(C)C] | 461.2 | 43 |
| 40 | 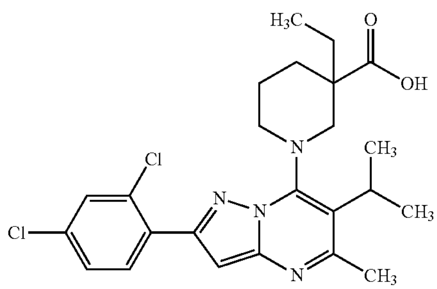 [SMILES: CCC1(C(=O)O)CCCN(c2c(C(C)C)c(C)nc3cc(-c4ccc(Cl)cc4Cl)nn23)C1] | 475.1 | 43 |
| 41 | 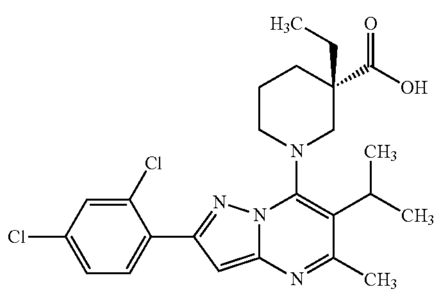 [SMILES: CC[C@]1(C(=O)O)CCCN(c2c(C(C)C)c(C)nc3cc(-c4ccc(Cl)cc4Cl)nn23)C1] | 475.1 | 43 |
| 42 | 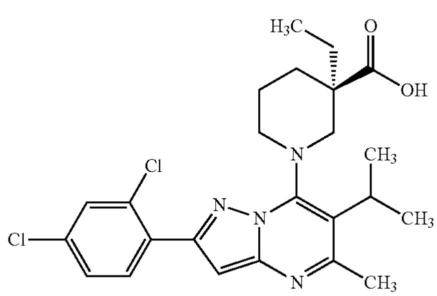 [SMILES: CC[C@@]1(C(=O)O)CCCN(c2c(C(C)C)c(C)nc3cc(-c4ccc(Cl)cc4Cl)nn23)C1] | 475.2 | 43 |

TABLE 8-continued

| Example | Structure | LC-MS (ESI) m/z [MH+] | Intermediate |
|---------|-----------|------------------------|--------------|
| 43 | 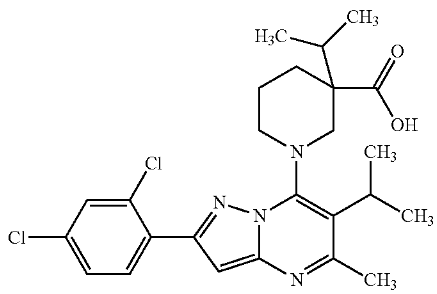 [SMILES: Cc1nc2cc(-c3ccc(Cl)cc3Cl)nn2c(N2CCCC(C(=O)O)(C(C)C)C2)c1C(C)C] | 489.2 | 43 |
| 44 | 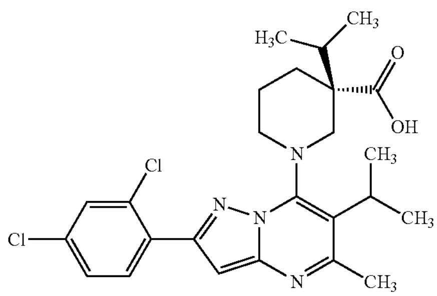 [SMILES: Cc1nc2cc(-c3ccc(Cl)cc3Cl)nn2c(N2CCC[C@@](C(=O)O)(C(C)C)C2)c1C(C)C] | 489.2 | 43 |
| 45 | 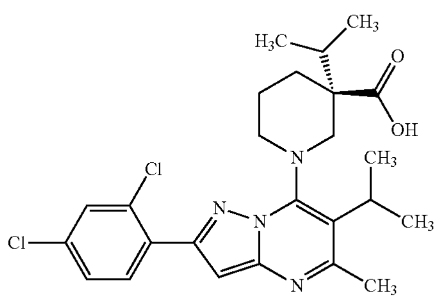 | 489.1 | 43 |
| 46 | 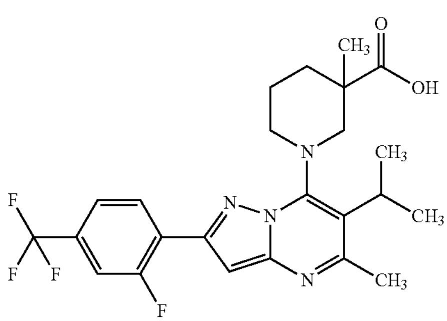 [SMILES: Cc1nc2cc(-c3ccc(C(F)(F)F)cc3F)nn2c(N2CCCC(C)(C(=O)O)C2)c1C(C)C] | 479.2 | 44 |
| 47 | 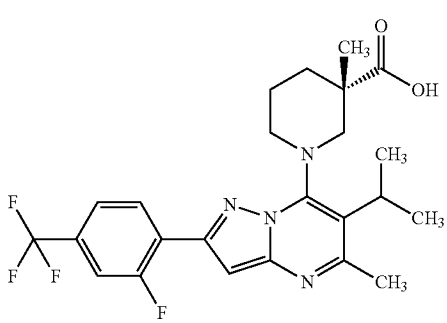 [SMILES: Cc1nc2cc(-c3ccc(C(F)(F)F)cc3F)nn2c(N2CCC[C@](C)(C(=O)O)C2)c1C(C)C] | 479.2 | 44 |

TABLE 8-continued

| Example | Structure | LC-MS (ESI) m/z [MH+] | Intermediate |
|---|---|---|---|
| 48 | 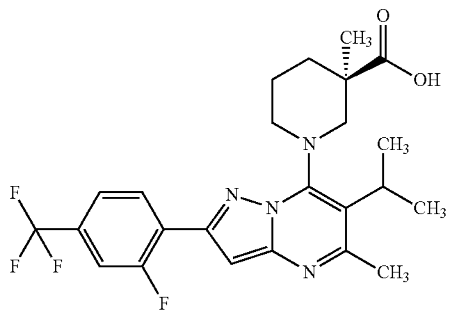 [SMILES: Cc1nc2cc(-c3ccc(C(F)(F)F)cc3F)nn2c(N2CCC[C@@](C)(C(=O)O)C2)c1C(C)C] | 479.2 | 44 |
| 49 | 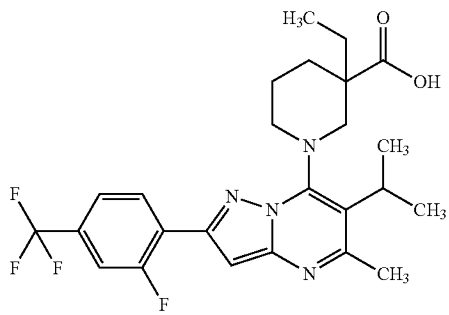 [SMILES: CCC1(C(=O)O)CCCN(c2c(C(C)C)c(C)nc3cc(-c4ccc(C(F)(F)F)cc4F)nn23)C1] | 493.2 | 44 |
| 50 | 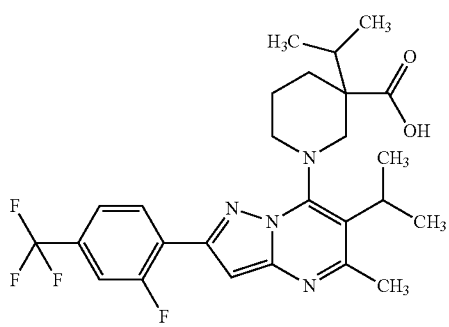 [SMILES: Cc1nc2cc(-c3ccc(C(F)(F)F)cc3F)nn2c(N2CCCC(C(=O)O)(C(C)C)C2)c1C(C)C] | 507.3 | 44 |
| 51 | 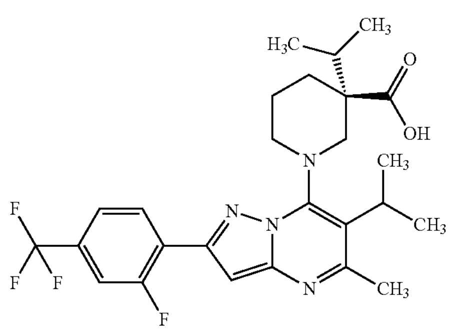 [SMILES: Cc1nc2cc(-c3ccc(C(F)(F)F)cc3F)nn2c(N2CCC[C@](C(=O)O)(C(C)C)C2)c1C(C)C] | 507.2 | 44 |
| 52 | 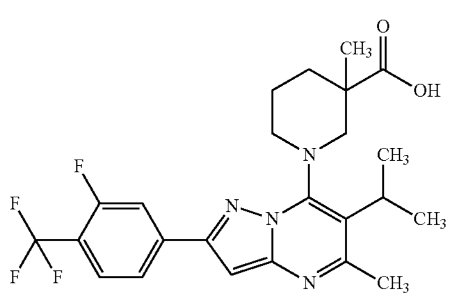 [SMILES: Cc1nc2cc(-c3ccc(C(F)(F)F)c(F)c3)nn2c(N2CCCC(C)(C(=O)O)C2)c1C(C)C] | 479.2 | 45 |

TABLE 8-continued

| Example | Structure | LC-MS (ESI) m/z [MH+] | Intermediate |
|---|---|---|---|
| 53 | 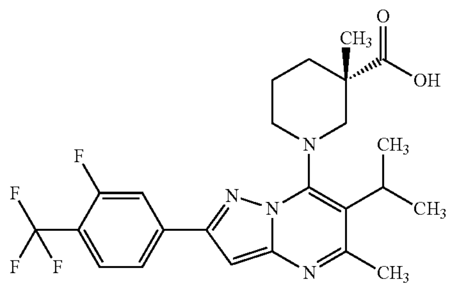 [SMILES: Cc1nc2cc(-c3ccc(C(F)(F)F)c(F)c3)nn2c(N2CCC[C@](C)(C(=O)O)C2)c1C(C)C] | 479.2 | 45 |
| 54 | 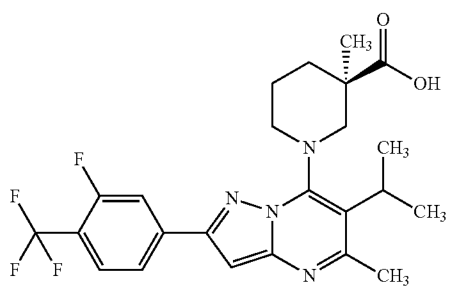 [SMILES: Cc1nc2cc(-c3ccc(C(F)(F)F)c(F)c3)nn2c(N2CCC[C@@](C)(C(=O)O)C2)c1C(C)C] | 479.2 | 45 |
| 55 | 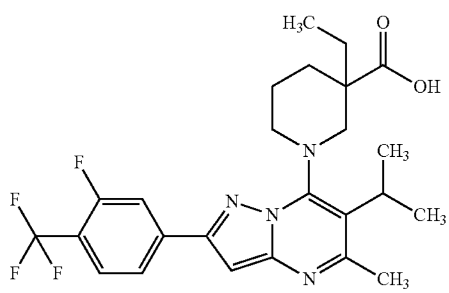 [SMILES: CCC1(C(=O)O)CCCN(c2c(C(C)C)c(C)nc3cc(-c4ccc(C(F)(F)F)c(F)c4)nn23)C1] | 493.2 | 45 |
| 56 | 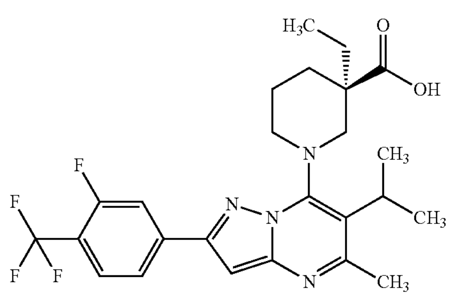 [SMILES: CC[C@@]1(C(=O)O)CCCN(c2c(C(C)C)c(C)nc3cc(-c4ccc(C(F)(F)F)c(F)c4)nn23)C1] | 493.2 | 45 |
| 57 | 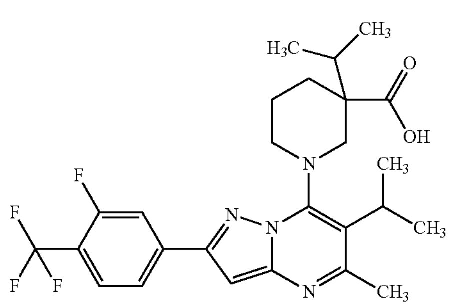 [SMILES: Cc1nc2cc(-c3ccc(C(F)(F)F)c(F)c3)nn2c(N2CCCC(C(=O)O)(C(C)C)C2)c1C(C)C] | 507.3 | 45 |

TABLE 8-continued

| Example | Structure | LC-MS (ESI) m/z [MH+] | Intermediate |
|---|---|---|---|
| 58 | 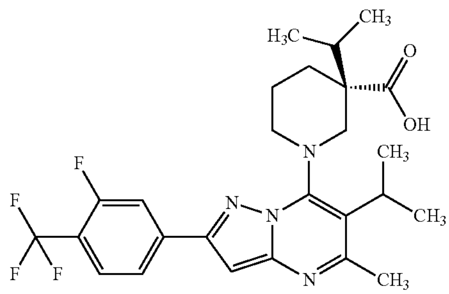 [SMILES: Cc1nc2cc(-c3ccc(C(F)(F)F)c(F)c3)nn2c(N2CCC[C@@](C(=O)O)(C(C)C)C2)c1C(C)C] | 507.2 | 45 |
| 59 | 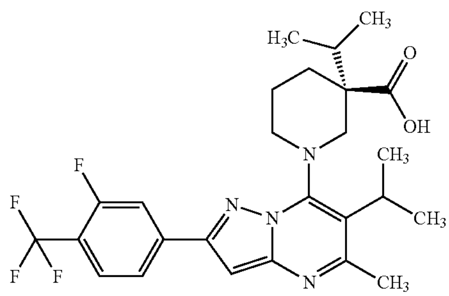 [SMILES: Cc1nc2cc(-c3ccc(C(F)(F)F)c(F)c3)nn2c(N2CCC[C@](C(=O)O)(C(C)C)C2)c1C(C)C] | 507.3 | 45 |
| 60 | 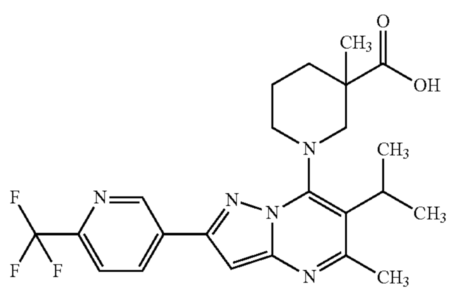 [SMILES: Cc1nc2cc(-c3ccc(C(F)(F)F)nc3)nn2c(N2CCCC(C)(C(=O)O)C2)c1C(C)C] | 462.3 | 46 |
| 61 | 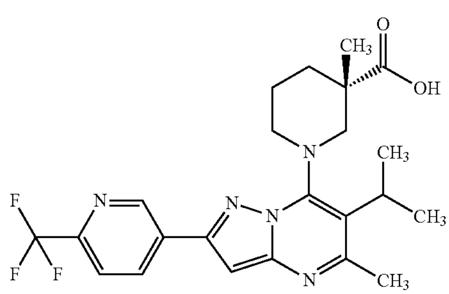 | 462.3 | 46 |
| 62 | 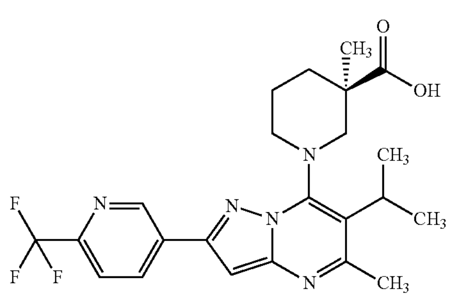 [SMILES: Cc1nc2cc(-c3ccc(C(F)(F)F)nc3)nn2c(N2CCC[C@@](C)(C(=O)O)C2)c1C(C)C] | 462.3 | 46 |

TABLE 8-continued

| Example | Structure | LC-MS (ESI) m/z [MH+] | Intermediate |
|---|---|---|---|
| 63 | 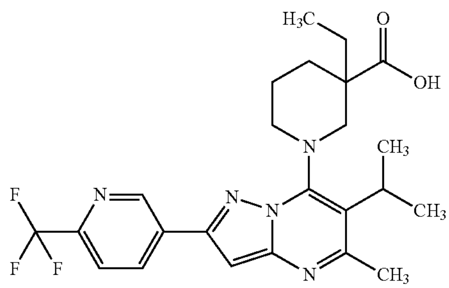 [SMILES: CCC1(C(=O)O)CCCN(c2c(C(C)C)c(C)nc3cc(-c4ccc(C(F)(F)F)nc4)nn23)C1] | 476.2 | 46 |
| 64 | 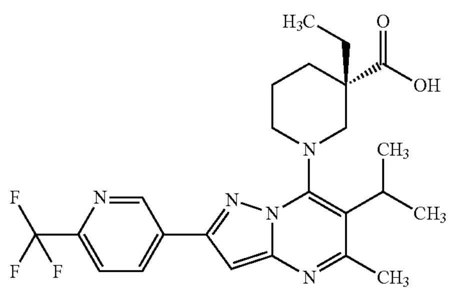 | 476.3 | 46 |
| 65 | 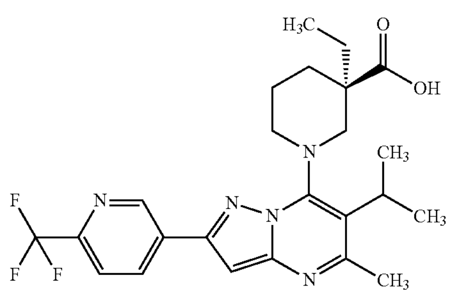 | 476.2 | 46 |
| 66 | 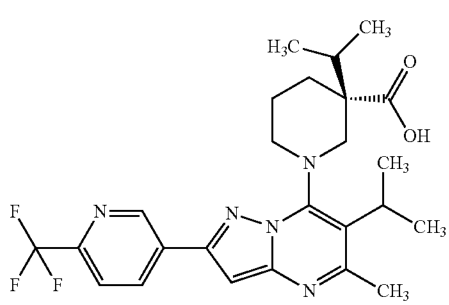 [SMILES: Cc1nc2cc(-c3ccc(C(F)(F)F)nc3)nn2c(N2CCC[C@@](C(=O)O)(C(C)C)C2)c1C(C)C] | 490.3 | 46 |
| 67 | 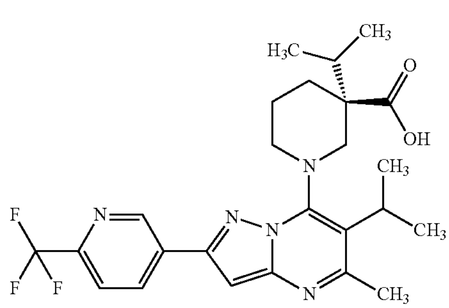 | 490.2 | 46 |

TABLE 8-continued

| Example | Structure | LC-MS (ESI) m/z [MH+] | Intermediate |
|---|---|---|---|
| 68 | 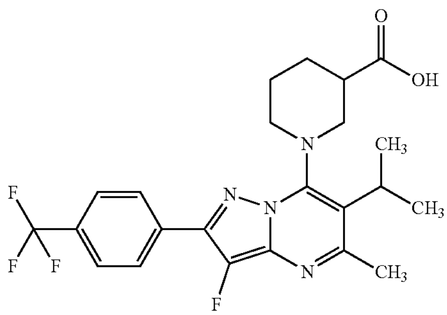 [SMILES: Cc1nc2c(F)c(-c3ccc(C(F)(F)F)cc3)nn2c(N2CCCC(C(=O)O)C2)c1C(C)C] | 465.1 | 47 |
| 69 | 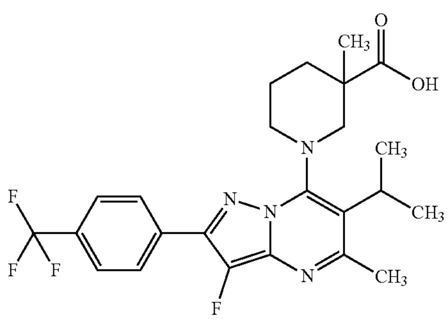 [SMILES: Cc1nc2c(F)c(-c3ccc(C(F)(F)F)cc3)nn2c(N2CCCC(C)(C(=O)O)C2)c1C(C)C] | 479.2 | 47 |
| 70 | 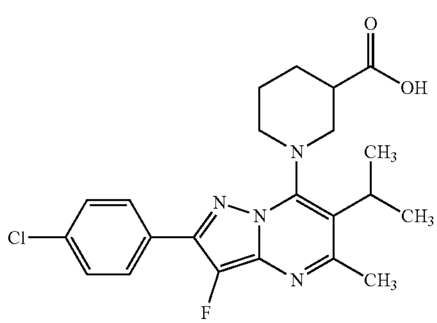 [SMILES: Cc1nc2c(F)c(-c3ccc(Cl)cc3)nn2c(N2CCCC(C(=O)O)C2)c1C(C)C] | 431.1 | 48 |
| 71 | 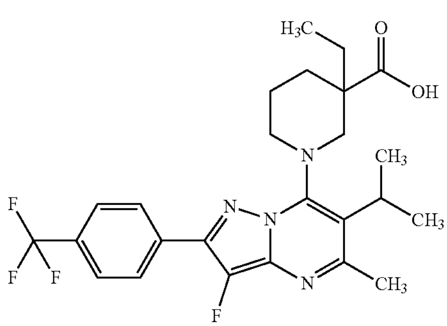 [SMILES: CCC1(C(=O)O)CCCN(c2c(C(C)C)c(C)nc3c(F)c(-c4ccc(C(F)(F)F)cc4)nn23)C1] | 493.2 | 47 |

TABLE 8-continued

| Example | Structure | LC-MS (ESI) m/z [MH+] | Intermediate |
|---|---|---|---|
| 72 | 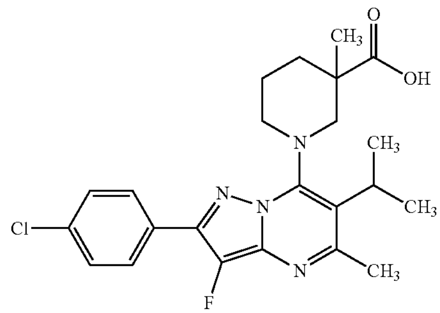 [SMILES: Cc1nc2c(F)c(-c3ccc(Cl)cc3)nn2c(N2CCCC(C)(C(=O)O)C2)c1C(C)C] | 445.1 | 48 |
| 73 | 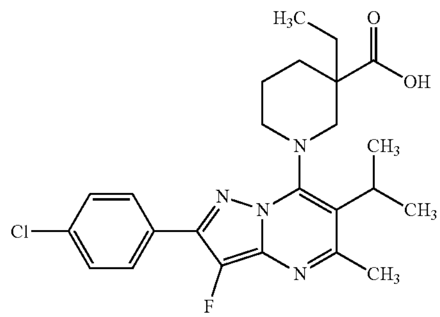 [SMILES: CCC1(C(=O)O)CCCN(c2c(C(C)C)c(C)nc3c(F)c(-c4ccc(Cl)cc4)nn23)C1] | 459.2 | 48 |
| 74 | 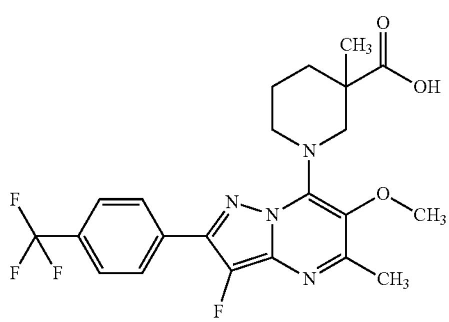 [SMILES: COc1c(C)nc2c(F)c(-c3ccc(C(F)(F)F)cc3)nn2c1N1CCCC(C)(C(=O)O)C1] | 467.2 | 106 |
| 75 | 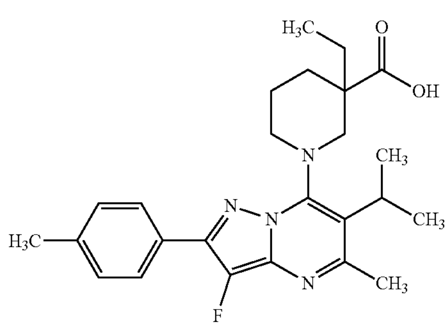 [SMILES: CCC1(C(=O)O)CCCN(c2c(C(C)C)c(C)nc3c(F)c(-c4ccc(C)cc4)nn23)C1] | 439.2 | 49 |

TABLE 8-continued
| Example | Structure | LC-MS (ESI) m/z [MH+] | Intermediate |
|---|---|---|---|
| 76 | 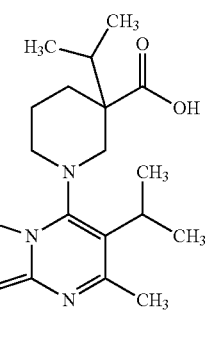 | 507.3 | 47 |
| 77 | 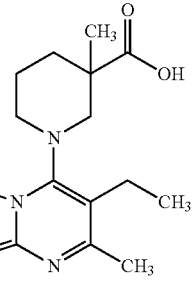 | 431.2 | 50 |
| 78 | 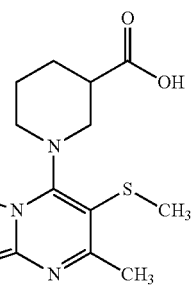 | 435.1 | 52 |
| 79 | 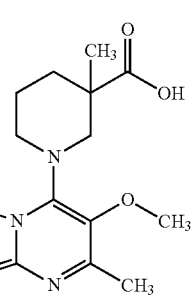 | 433.1 | 53 |

TABLE 8-continued

| Example | Structure | LC-MS (ESI) m/z [MH+] | Intermediate |
|---|---|---|---|
| 80 | 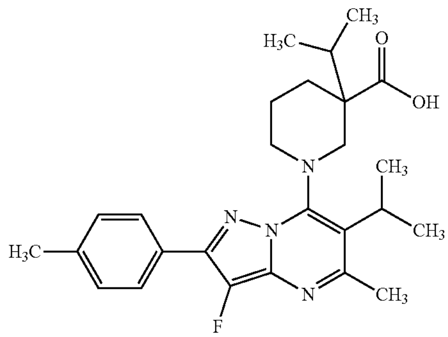 [SMILES: Cc1ccc(-c2nn3c(N4CCCC(C(=O)O)(C(C)C)C4)c(C(C)C)c(C)nc3c2F)cc1] | 453.3 | 49 |
| 81 | 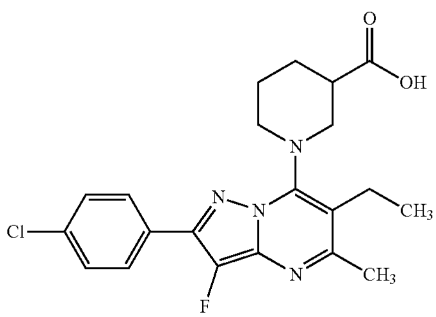 [SMILES: CCc1c(C)nc2c(F)c(-c3ccc(Cl)cc3)nn2c1N1CCCC(C(=O)O)C1] | 417.2 | 50 |
| 82 | 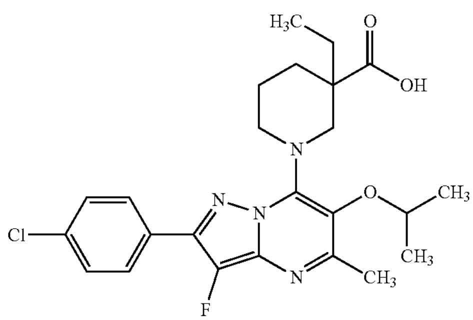 [SMILES: CCC1(C(=O)O)CCCN(c2c(OC(C)C)c(C)nc3c(F)c(-c4ccc(Cl)cc4)nn23)C1] | 475.1 | 54 |
| 83 | 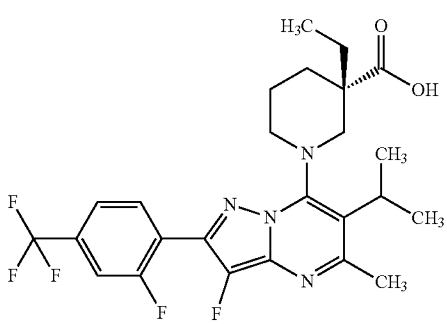 [SMILES: CC[C@]1(C(=O)O)CCCN(c2c(C(C)C)c(C)nc3c(F)c(-c4ccc(C(F)(F)F)cc4F)nn23)C1] | 511.3 | 105 |

TABLE 8-continued

| Example | Structure | LC-MS (ESI) m/z [MH+] | Intermediate |
|---|---|---|---|
| 84 | 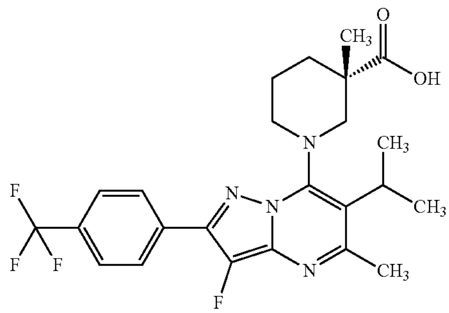 [SMILES: Cc1nc2c(F)c(-c3ccc(C(F)(F)F)cc3)nn2c(N2CCC[C@](C)(C(=O)O)C2)c1C(C)C] | 479.2 | 47 |
| 85 | 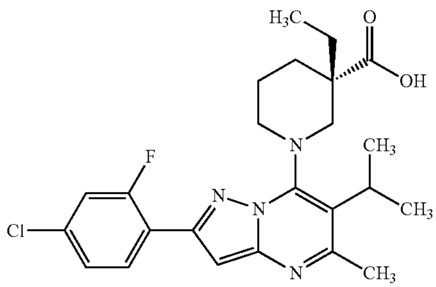 [SMILES: CC[C@]1(C(=O)O)CCCN(c2c(C(C)C)c(C)nc3cc(-c4ccc(Cl)cc4F)nn23)C1] | 459.3 | 55 |
| 86 | 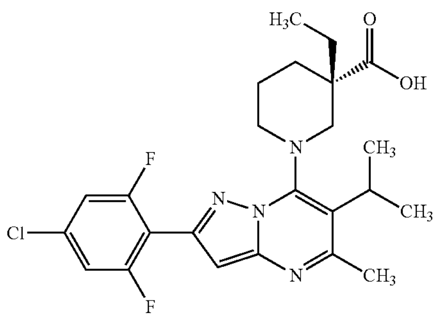 [SMILES: CC[C@]1(C(=O)O)CCCN(c2c(C(C)C)c(C)nc3cc(-c4c(F)cc(Cl)cc4F)nn23)C1] | 477.3 | 56 |
| 87 | 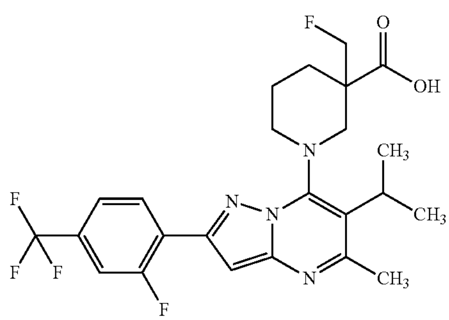 [SMILES: Cc1nc2cc(-c3ccc(C(F)(F)F)cc3F)nn2c(N2CCCC(CF)(C(=O)O)C2)c1C(C)C] | 497.3 | 44 |
| 88 | 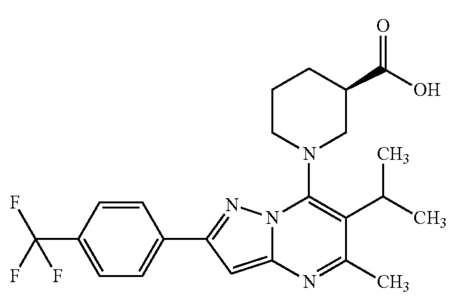 [SMILES: Cc1nc2cc(-c3ccc(C(F)(F)F)cc3)nn2c(N2CCC[C@@H](C(=O)O)C2)c1C(C)C] | 447.3 | 41 |

TABLE 8-continued

| Example | Structure | LC-MS (ESI) m/z [MH+] | Intermediate |
|---|---|---|---|
| 89 | 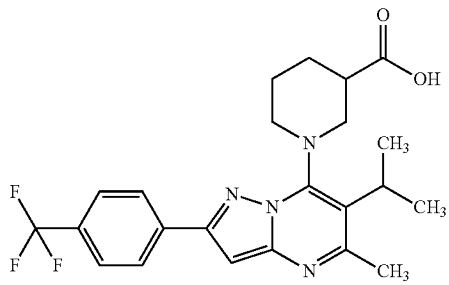 [SMILES: Cc1nc2cc(-c3ccc(C(F)(F)F)cc3)nn2c(N2CCCC(C(=O)O)C2)c1C(C)C] | 447.3 | 41 |
| 90 | 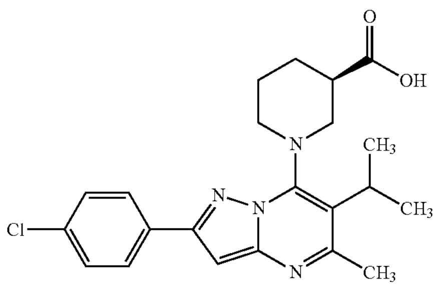 [SMILES: Cc1nc2cc(-c3ccc(Cl)cc3)nn2c(N2CCC[C@@H](C(=O)O)C2)c1C(C)C] | 413.1 | 40 |
| 91 | 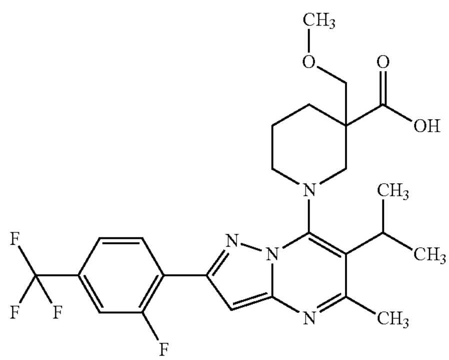 [SMILES: COCC1(C(=O)O)CCCN(c2c(C(C)C)c(C)nc3cc(-c4ccc(C(F)(F)F)cc4F)nn23)C1] | 509.1 | 44 |
| 92 | 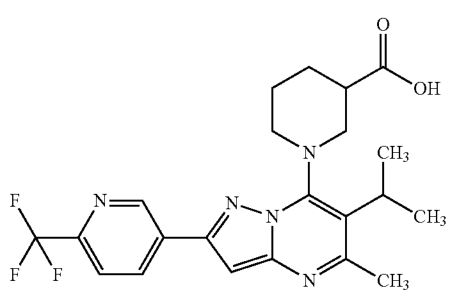 [SMILES: Cc1nc2cc(-c3ccc(C(F)(F)F)nc3)nn2c(N2CCCC(C(=O)O)C2)c1C(C)C] | 448.2 | 46 |
| 93 | 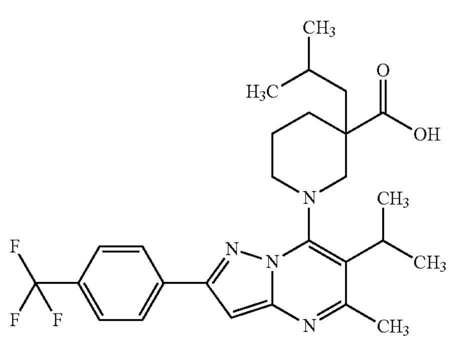 [SMILES: Cc1nc2cc(-c3ccc(C(F)(F)F)cc3)nn2c(N2CCCC(CC(C)C)(C(=O)O)C2)c1C(C)C] | 503.3 | 41 |

TABLE 8-continued

| Example | Structure | LC-MS (ESI) m/z [MH+] | Intermediate |
|---|---|---|---|
| 94 | 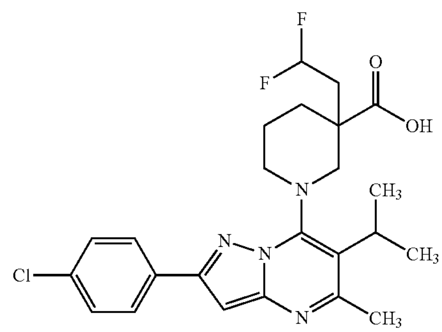 [SMILES: Cc1nc2cc(-c3ccc(Cl)cc3)nn2c(N2CCCC(CC(F)F)(C(=O)O)C2)c1C(C)C] | 477.2 | 40 |
| 95 | 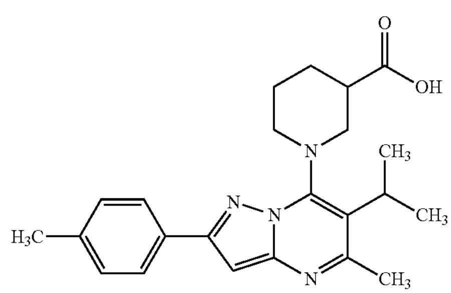 [SMILES: Cc1ccc(-c2cc3nc(C)c(C(C)C)c(N4CCCC(C(=O)O)C4)n3n2)cc1] | 393.3 | 57 |
| 96 | 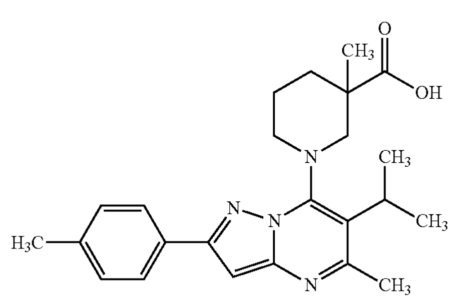 [SMILES: Cc1ccc(-c2cc3nc(C)c(C(C)C)c(N4CCCC(C)(C(=O)O)C4)n3n2)cc1] | 407.2 | 57 |
| 97 | 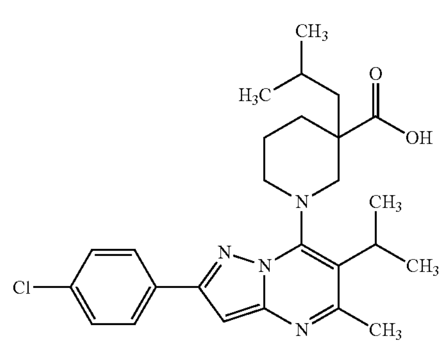 [SMILES: Cc1nc2cc(-c3ccc(Cl)cc3)nn2c(N2CCCC(CC(C)C)(C(=O)O)C2)c1C(C)C] | 469.3 | 40 |

TABLE 8-continued

| Example | Structure | LC-MS (ESI) m/z [MH+] | Intermediate |
|---------|-----------|------------------------|--------------|
| 98 | 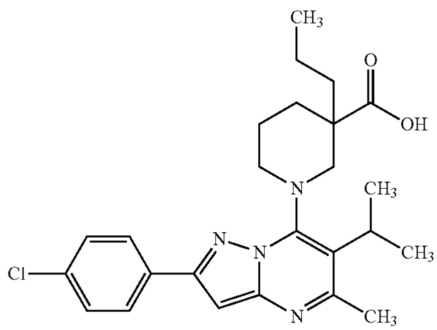 [SMILES: CCCC1(C(=O)O)CCCN(c2c(C(C)C)c(C)nc3cc(-c4ccc(Cl)cc4)nn23)C1] | 455.2 | 40 |
| 99 | 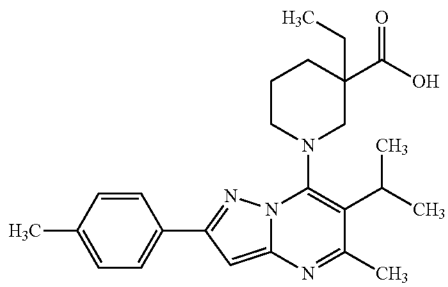 [SMILES: CCC1(C(=O)O)CCCN(c2c(C(C)C)c(C)nc3cc(-c4ccc(C)cc4)nn23)C1] | 421.2 | 57 |
| 100 | 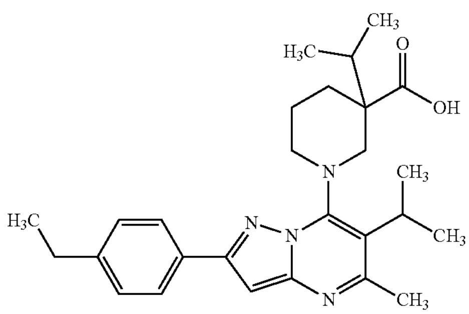 [SMILES: CCc1ccc(-c2cc3nc(C)c(C(C)C)c(N4CCCC(C(=O)O)(C(C)C)C4)n3n2)cc1] | 449.3 | 58 |
| 101 | 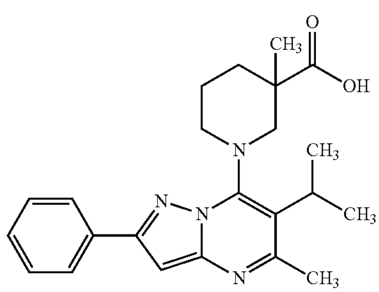 [SMILES: Cc1nc2cc(-c3ccccc3)nn2c(N2CCCC(C)(C(=O)O)C2)c1C(C)C] | 393.2 | 59 |
| 102 | 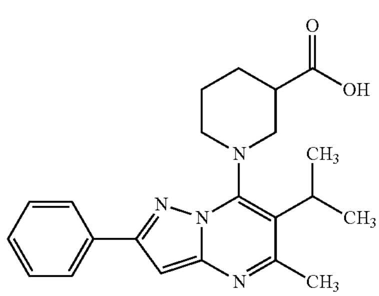 [SMILES: Cc1nc2cc(-c3ccccc3)nn2c(N2CCCC(C(=O)O)C2)c1C(C)C] | 379.2 | 59 |

TABLE 8-continued

| Example | Structure | LC-MS (ESI) m/z [MH+] | Intermediate |
|---|---|---|---|
| 103 | 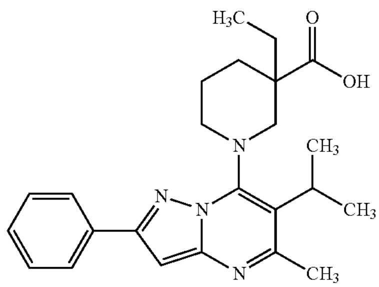 [SMILES: CCC1(C(=O)O)CCCN(c2c(C(C)C)c(C)nc3cc(-c4ccccc4)nn23)C1] | 407.3 | 59 |
| 104 | 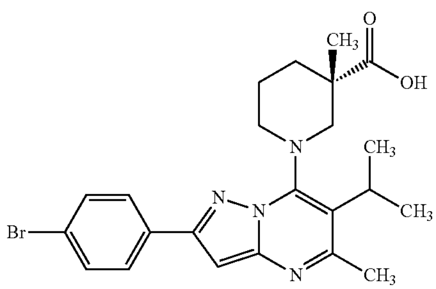 | 473.1 | 60 |
| 105 | 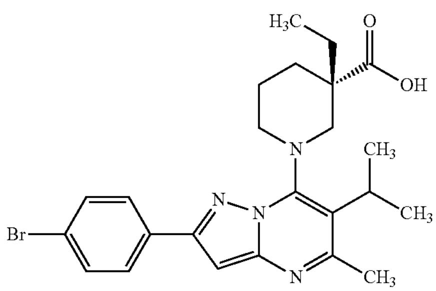 | 485.2 | 60 |
| 106 | 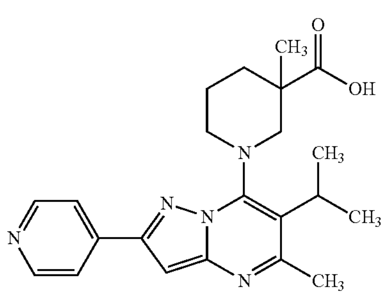 [SMILES: Cc1nc2cc(-c3ccncc3)nn2c(N2CCCC(C)(C(=O)O)C2)c1C(C)C] | 394.2 | 61 |
| 107 | 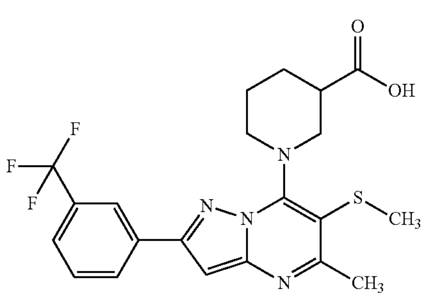 [SMILES: CSc1c(C)nc2cc(-c3cccc(C(F)(F)F)c3)nn2c1N1CCCC(C(=O)O)C1] | 451.2 | 62 |

TABLE 8-continued

| Example | Structure | LC-MS (ESI) m/z [MH⁺] | Intermediate |
|---|---|---|---|
| 108 | 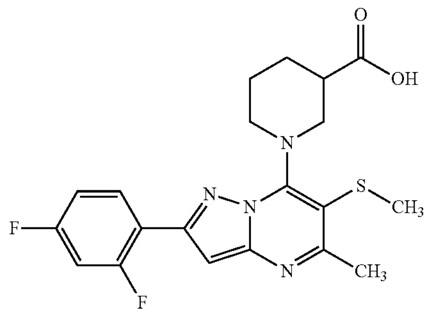 [SMILES: CSc1c(C)nc2cc(-c3ccc(F)cc3F)nn2c1N1CCCC(C(=O)O)C1] | 419.2 | 63 |
| 109 | 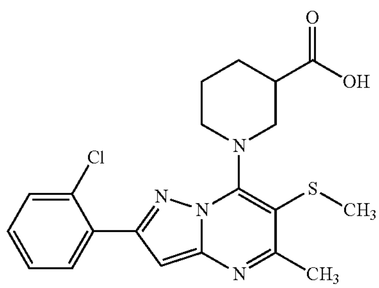 [SMILES: CSc1c(C)nc2cc(-c3ccccc3Cl)nn2c1N1CCCC(C(=O)O)C1] | 417.1 | 64 |
| 110 | 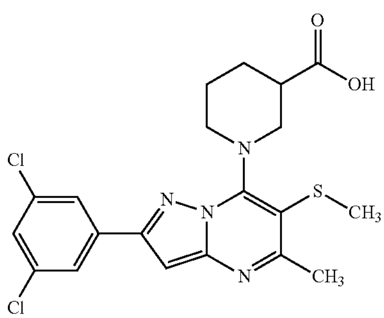 [SMILES: CSc1c(C)nc2cc(-c3cc(Cl)cc(Cl)c3)nn2c1N1CCCC(C(=O)O)C1] | 451.2 | 65 |
| 111 | 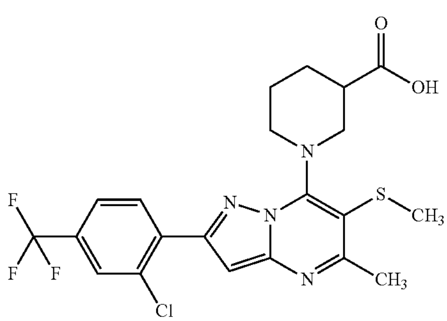 [SMILES: CSc1c(C)nc2cc(-c3ccc(C(F)(F)F)cc3Cl)nn2c1N1CCCC(C(=O)O)C1] | 485.1 | 66 |
| 112 | 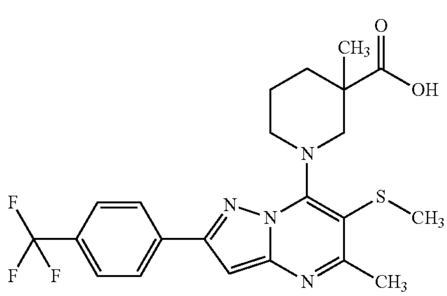 | 465.2 | 67 |

TABLE 8-continued

| Example | Structure | LC-MS (ESI) m/z [MH+] | Intermediate |
|---|---|---|---|
| 113 | 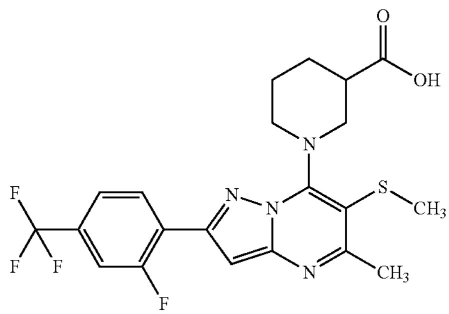 | 469.1 | 68 |
| 114 | 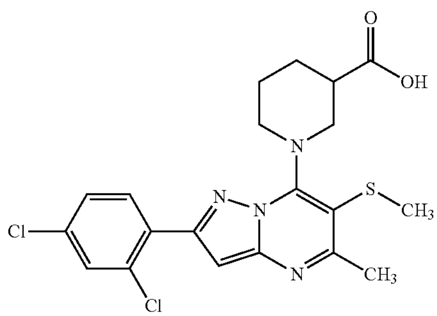 [SMILES: CSc1c(C)nc2cc(-c3ccc(Cl)cc3Cl)nn2c1N1CCCC(C(=O)O)C1] | 451.2 | 69 |
| 115 | 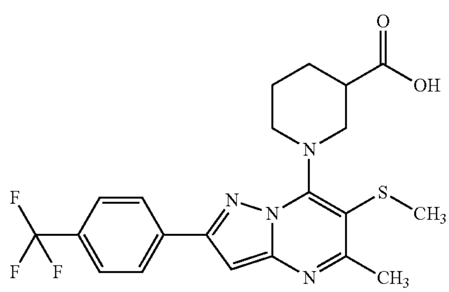 [SMILES: CSc1c(C)nc2cc(-c3ccc(C(F)(F)F)cc3)nn2c1N1CCCC(C(=O)O)C1] | 451.2 | 67 |
| 116 | 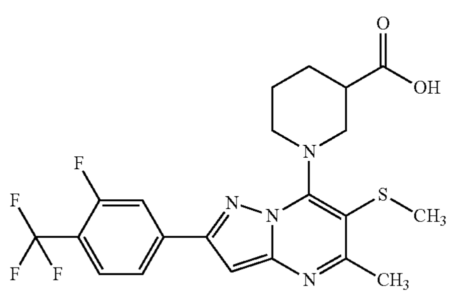 [SMILES: CSc1c(C)nc2cc(-c3ccc(C(F)(F)F)c(F)c3)nn2c1N1CCCC(C(=O)O)C1] | 469.1 | 70 |
| 117 | 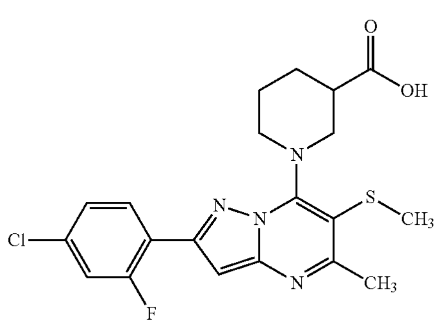 [SMILES: CSc1c(C)nc2cc(-c3ccc(Cl)cc3F)nn2c1N1CCCC(C(=O)O)C1] | 435.1 | 71 |

TABLE 8-continued

| Example | Structure | LC-MS (ESI) m/z [MH+] | Intermediate |
|---|---|---|---|
| 118 | 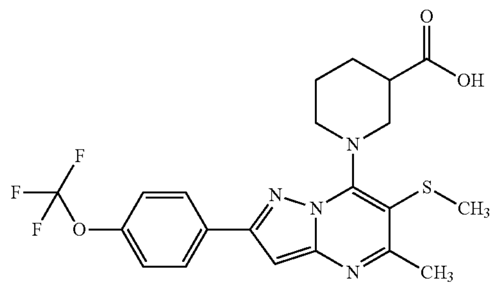 [SMILES: CSc1c(C)nc2cc(-c3ccc(OC(F)(F)F)cc3)nn2c1N1CCCC(C(=O)O)C1] | 467.2 | 72 |
| 119 | 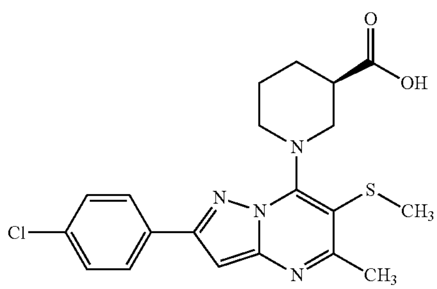 [SMILES: CSc1c(C)nc2cc(-c3ccc(Cl)cc3)nn2c1N1CCC[C@@H](C(=O)O)C1] | 417.1 | 73 |
| 120 | 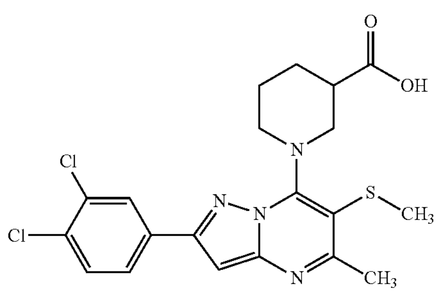 | 451.2 | 74 |
| 121 | 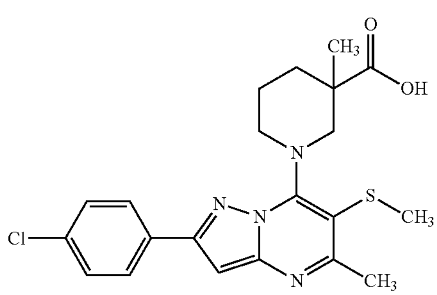 | 431.1 | 73 |
| 122 | 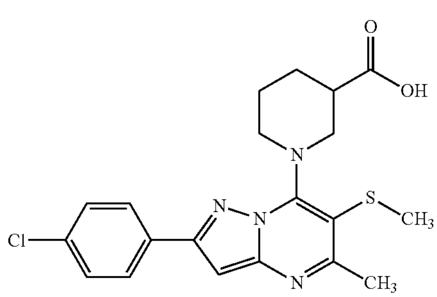 | 417.1 | 73 |

TABLE 8-continued

| Example | Structure | LC-MS (ESI) m/z [MH+] | Intermediate |
|---|---|---|---|
| 123 | 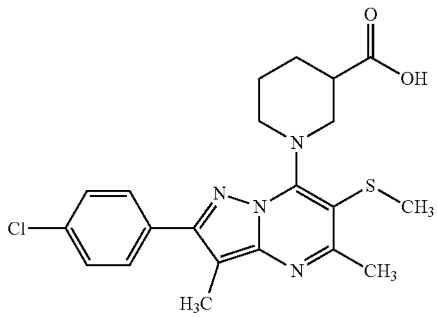 [SMILES: CSc1c(C)nc2c(C)c(-c3ccc(Cl)cc3)nn2c1N1CCCC(C(=O)O)C1] | 431.2 | 75 |
| 124 | 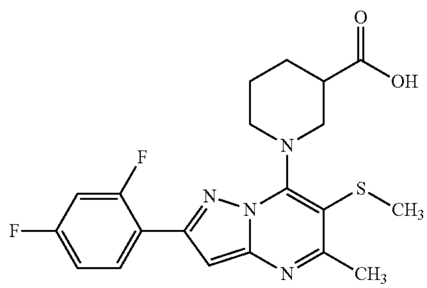 [SMILES: CSc1c(C)nc2cc(-c3ccc(F)cc3F)nn2c1N1CCCC(C(=O)O)C1] | 419.2 | 63 |
| 125 | 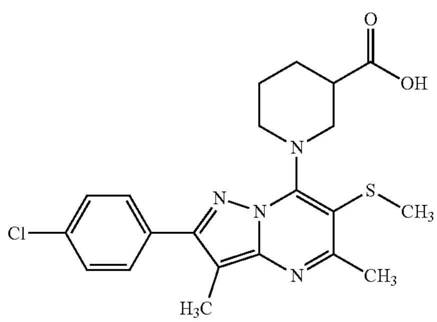 [SMILES: CSc1c(C)nc2c(C)c(-c3ccc(Cl)cc3)nn2c1N1CCCC(C(=O)O)C1] | 431.2 | 75 |
| 126 | 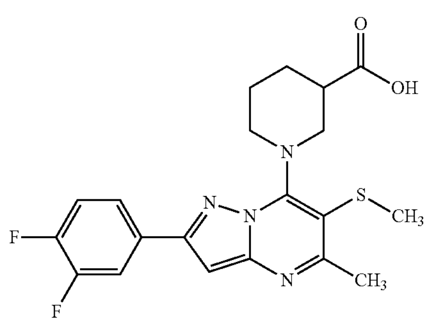 [SMILES: CSc1c(C)nc2cc(-c3ccc(F)c(F)c3)nn2c1N1CCCC(C(=O)O)C1] | 419.2 | 76 |
| 127 | 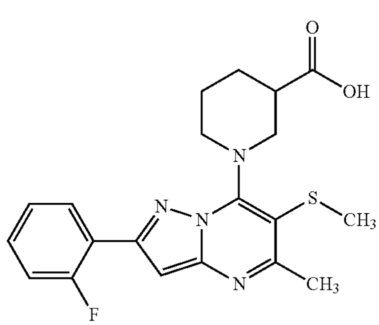 [SMILES: CSc1c(C)nc2cc(-c3ccccc3F)nn2c1N1CCCC(C(=O)O)C1] | 401.2 | 77 |

TABLE 8-continued

| Example | Structure | LC-MS (ESI) m/z [MH+] | Intermediate |
|---------|-----------|------------------------|--------------|
| 128 | 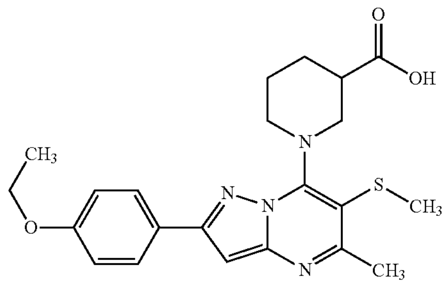 [SMILES: CCOc1ccc(-c2cc3nc(C)c(SC)c(N4CCCC(C(=O)O)C4)n3n2)cc1] | 427.3 | 78 |
| 129 | 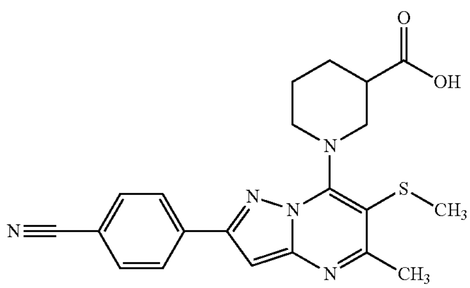 [SMILES: CSc1c(C)nc2cc(-c3ccc(C#N)cc3)nn2c1N1CCCC(C(=O)O)C1] | 408.2 | 79 |
| 130 | 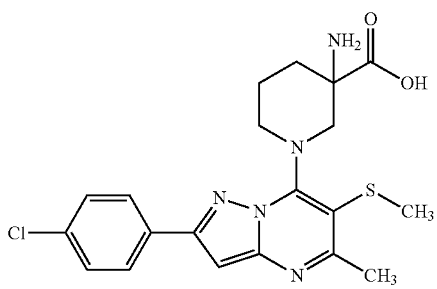 | 432.1 | 73 |
| 131 | 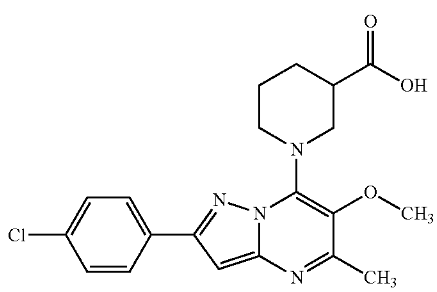 [SMILES: COc1c(C)nc2cc(-c3ccc(Cl)cc3)nn2c1N1CCCC(C(=O)O)C1] | 401.1 | 80 |
| 132 | 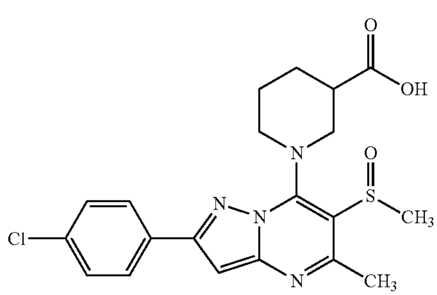 [SMILES: Cc1nc2cc(-c3ccc(Cl)cc3)nn2c(N2CCCC(C(=O)O)C2)c1S(C)=O] | 433.1 | 81 |

TABLE 8-continued

| Example | Structure | LC-MS (ESI) m/z [MH+] | Intermediate |
|---|---|---|---|
| 133 | 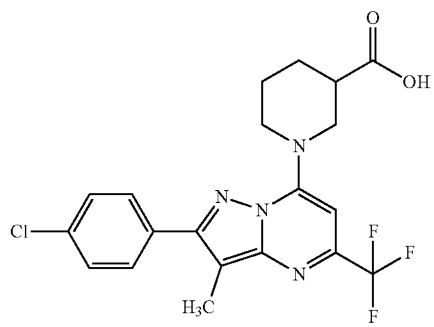 [SMILES: Cc1c(-c2ccc(Cl)cc2)nn2c(N3CCCC(C(=O)O)C3)cc(C(F)(F)F)nc12] | 439.2 | 51 |
| 134 | 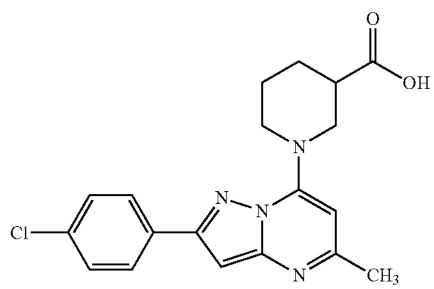 [SMILES: Cc1cc(N2CCCC(C(=O)O)C2)n2nc(-c3ccc(Cl)cc3)cc2n1] | 371.1 | 82 |
| 135 | 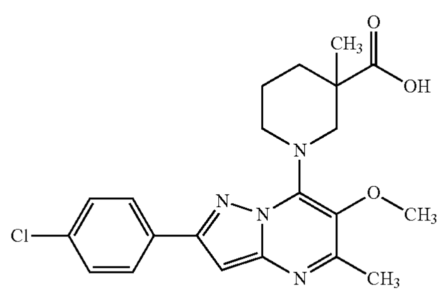 [SMILES: COc1c(C)nc2cc(-c3ccc(Cl)cc3)nn2c1N1CCCC(C)(C(=O)O)C1] | 416.2 | 80 |
| 136 | 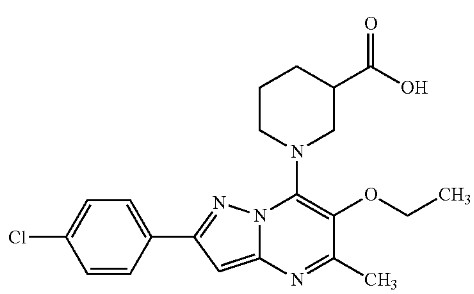 [SMILES: CCOc1c(C)nc2cc(-c3ccc(Cl)cc3)nn2c1N1CCCC(C(=O)O)C1] | 418.2 | 83 |
| 137 | 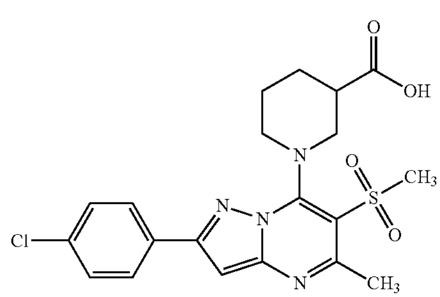 [SMILES: Cc1nc2cc(-c3ccc(Cl)cc3)nn2c(N2CCCC(C(=O)O)C2)c1S(C)(=O)=O] | 449.1 | 84 |

TABLE 8-continued
| Example | Structure | LC-MS (ESI) m/z [MH+] | Intermediate |
|---|---|---|---|
| 138 | 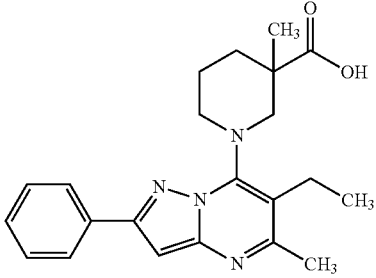 [SMILES: CCc1c(C)nc2cc(-c3ccccc3)nn2c1N1CCCC(C)(C(=O)O)C1] | 379.2 | 85 |
| 139 | 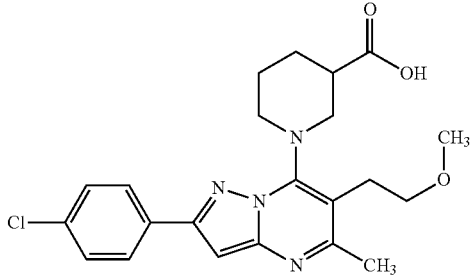 [SMILES: COCCc1c(C)nc2cc(-c3ccc(Cl)cc3)nn2c1N1CCCC(C(=O)O)C1] | 429.2 | 86 |
| 140 | 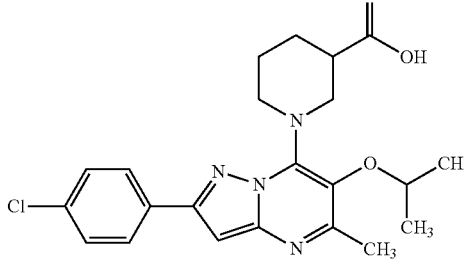 | 429.1 | 87 |
| 141 | 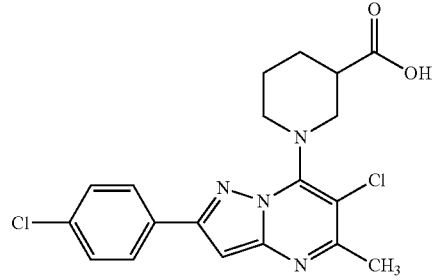 [SMILES: Cc1nc2cc(-c3ccc(Cl)cc3)nn2c(N2CCCC(C(=O)O)C2)c1Cl] | 405.1 | 88 |
| 142 | 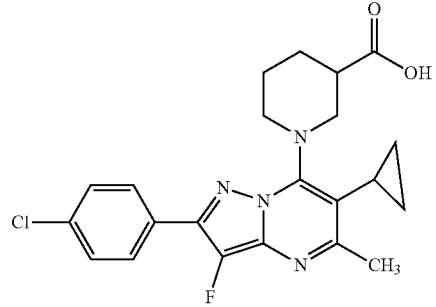 [SMILES: Cc1nc2c(F)c(-c3ccc(Cl)cc3)nn2c(N2CCCC(C(=O)O)C2)c1C1CC1] | 429.2 | 89 |

TABLE 8-continued

| Example | Structure | LC-MS (ESI) m/z [MH+] | Intermediate |
|---|---|---|---|
| 143 | 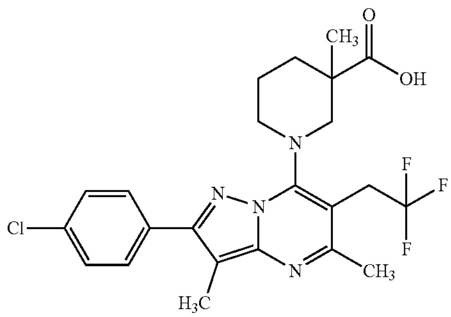 [SMILES: Cc1nc2c(C)c(-c3ccc(Cl)cc3)nn2c(N2CCCC(C)(C(=O)O)C2)c1CC(F)(F)F] | 481.2 | 90 |
| 144 | 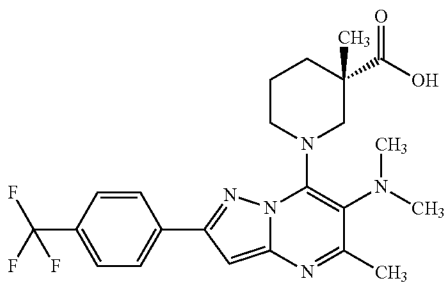 [SMILES: Cc1nc2cc(-c3ccc(C(F)(F)F)cc3)nn2c(N2CCC[C@](C)(C(=O)O)C2)c1N(C)C] | 462.2 | 91 |
| 145 | 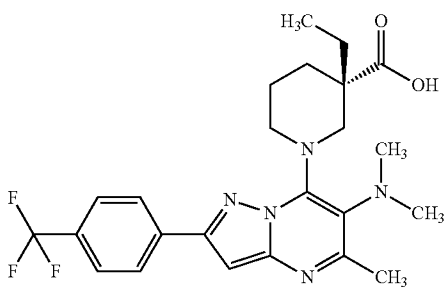 | 476.2 | 91 |
| 146 | 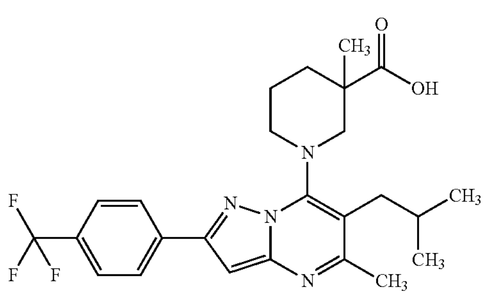 [SMILES: Cc1nc2cc(-c3ccc(C(F)(F)F)cc3)nn2c(N2CCCC(C)(C(=O)O)C2)c1CC(C)C] | 475.2 | 92 |
| 147 | 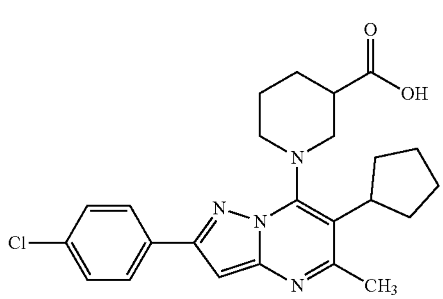 [SMILES: Cc1nc2cc(-c3ccc(Cl)cc3)nn2c(N2CCCC(C(=O)O)C2)c1C1CCCC1] | 439.2 | 93 |

TABLE 8-continued

| Example | Structure | LC-MS (ESI) m/z [MH+] | Intermediate |
|---|---|---|---|
| 148 | 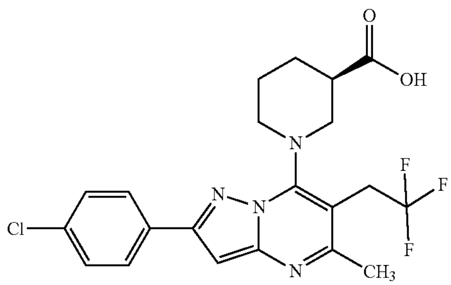 [SMILES: Cc1nc2cc(-c3ccc(Cl)cc3)nn2c(N2CCC[C@@H](C(=O)O)C2)c1CC(F)(F)F] | 453.1 | 94 |
| 149 | 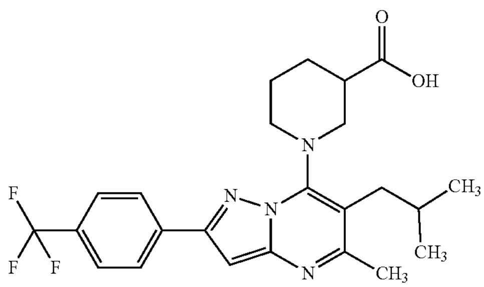 [SMILES: Cc1nc2cc(-c3ccc(C(F)(F)F)cc3)nn2c(N2CCCC(C(=O)O)C2)c1CC(C)C] | 461.2 | 92 |
| 150 | 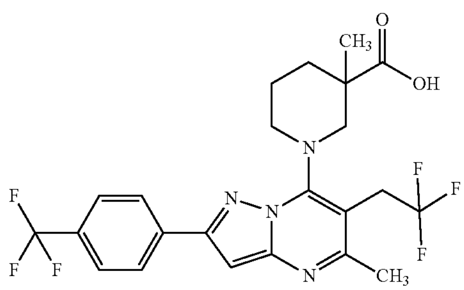 [SMILES: Cc1nc2cc(-c3ccc(C(F)(F)F)cc3)nn2c(N2CCCC(C)(C(=O)O)C2)c1CC(F)(F)F] | 501.2 | 95 |
| 151 | 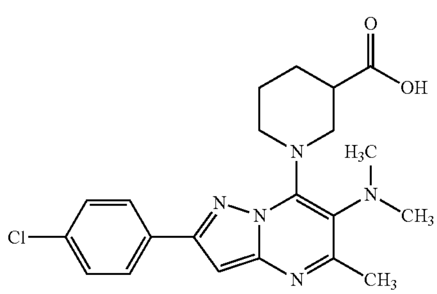 | 414.1 | 96 |
| 152 | 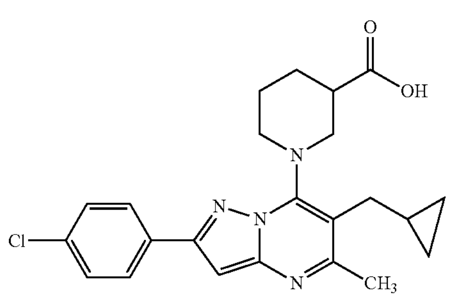 [SMILES: Cc1nc2cc(-c3ccc(Cl)cc3)nn2c(N2CCCC(C(=O)O)C2)c1CC1CC1] | 425.2 | 97 |

TABLE 8-continued
| Example | Structure | LC-MS (ESI) m/z [MH+] | Intermediate |
|---|---|---|---|
| 153 | 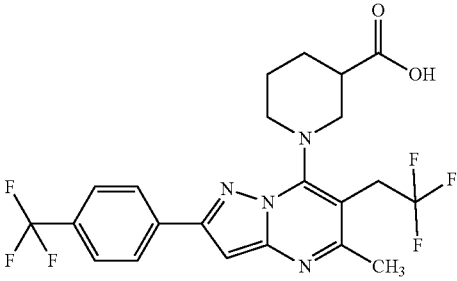 [SMILES: Cc1nc2cc(-c3ccc(C(F)(F)F)cc3)nn2c(N2CCCC(C(=O)O)C2)c1CC(F)(F)F] | 487.1 | 95 |
| 154 | 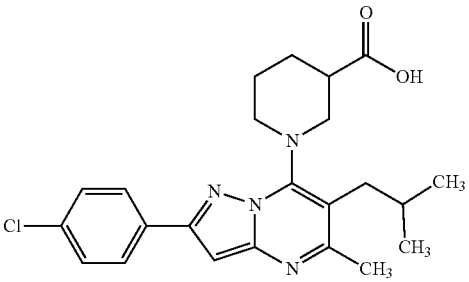 [SMILES: Cc1nc2cc(-c3ccc(Cl)cc3)nn2c(N2CCCC(C(=O)O)C2)c1CC(C)C] | 427.2 | 98 |
| 155 | 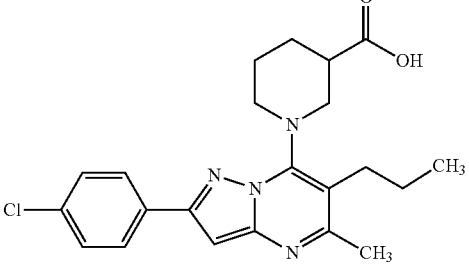 | 413.2 | 99 |
| 156 | 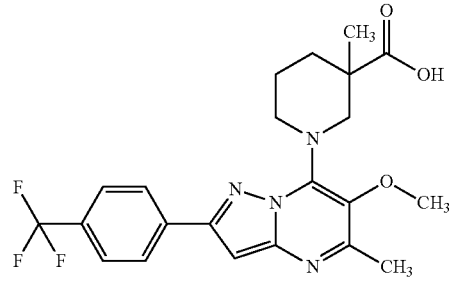 [SMILES: COc1c(C)nc2cc(-c3ccc(C(F)(F)F)cc3)nn2c1N1CCCC(C)(C(=O)O)C1] | 449.2 | 100 |
| 157 | 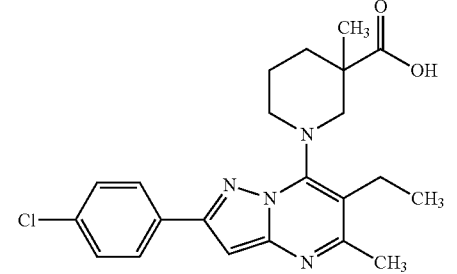 [SMILES: CCc1c(C)nc2cc(-c3ccc(Cl)cc3)nn2c1N1CCCC(C)(C(=O)O)C1] | 413.1 | 101 |

TABLE 8-continued

| Example | Structure | LC-MS (ESI) m/z [MH+] | Intermediate |
|---|---|---|---|
| 158 | 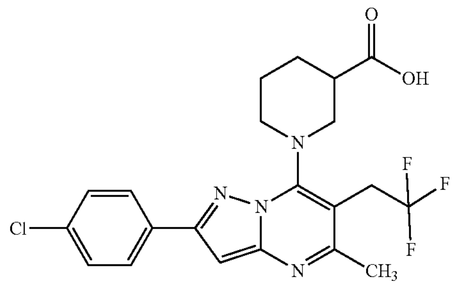 [SMILES: Cc1nc2cc(-c3ccc(Cl)cc3)nn2c(N2CCCC(C(=O)O)C2)c1CC(F)(F)F] | 453.1 | 94 |
| 159 | 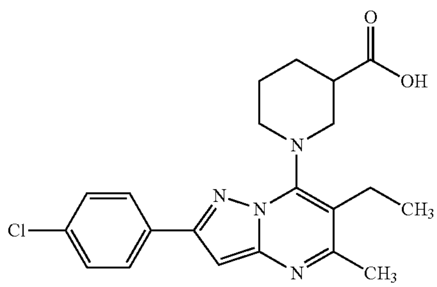 [SMILES: CCc1c(C)nc2cc(-c3ccc(Cl)cc3)nn2c1N1CCCC(C(=O)O)C1] | 399.2 | 101 |
| 160 | 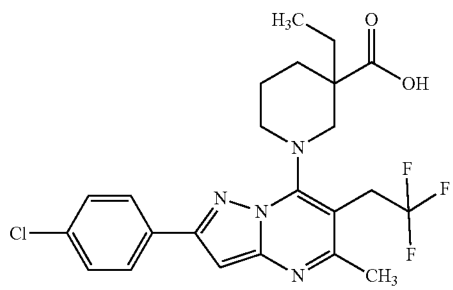 [SMILES: CCC1(C(=O)O)CCCN(c2c(CC(F)(F)F)c(C)nc3cc(-c4ccc(Cl)cc4)nn23)C1] | 481.1 | 94 |
| 161 | 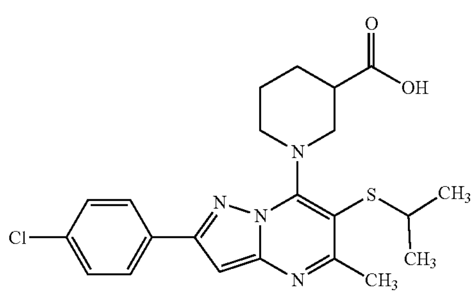 | 445.1 | 102 |
| 162 | 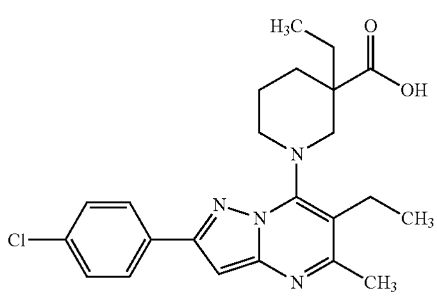 [SMILES: CCc1c(C)nc2cc(-c3ccc(Cl)cc3)nn2c1N1CCCC(CC)(C(=O)O)C1] | 427.2 | 101 |

TABLE 8-continued

| Example | Structure | LC-MS (ESI) m/z [MH+] | Intermediate |
|---|---|---|---|
| 163 | 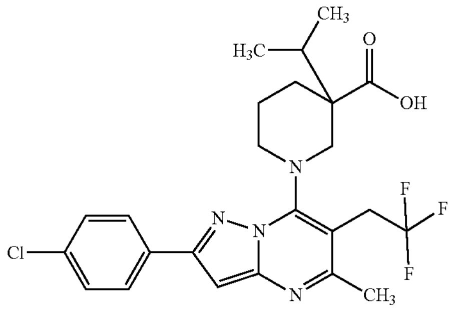 [SMILES: Cc1nc2cc(-c3ccc(Cl)cc3)nn2c(N2CCCC(C(=O)O)(C(C)C)C2)c1CC(F)(F)F] | 495.1 | 94 |
| 164 | 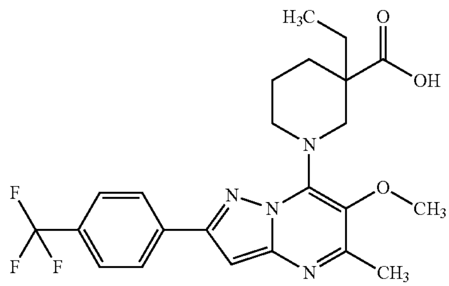 [SMILES: CCC1(C(=O)O)CCCN(c2c(OC)c(C)nc3cc(-c4ccc(C(F)(F)F)cc4)nn23)C1] | 463.1 | 100 |
| 165 | 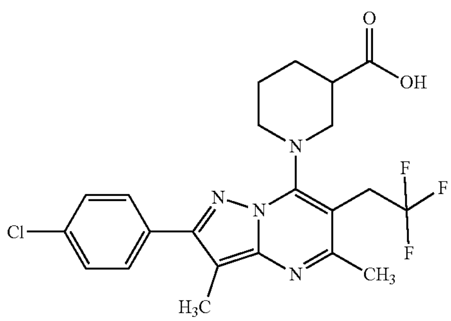 [SMILES: Cc1nc2c(C)c(-c3ccc(Cl)cc3)nn2c(N2CCCC(C(=O)O)C2)c1CC(F)(F)F] | 467.1 | 103 |
| 166 | 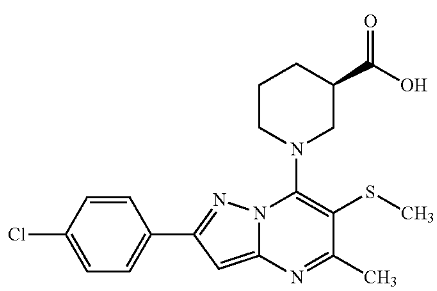 [SMILES: CSc1c(C)nc2cc(-c3ccc(Cl)cc3)nn2c1N1CCC[C@@H](C(=O)O)C1] | 417.1 | 73 |
| 167 | 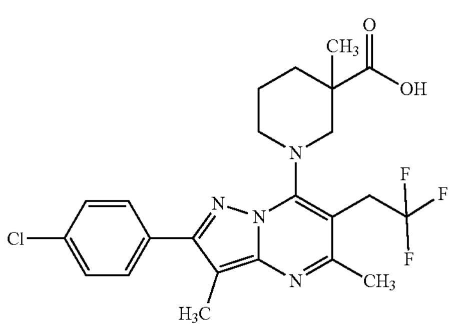 [SMILES: Cc1nc2c(C)c(-c3ccc(Cl)cc3)nn2c(N2CCCC(C)(C(=O)O)C2)c1CC(F)(F)F] | 481.2 | 103 |

TABLE 8-continued

| Example | Structure | LC-MS (ESI) m/z [MH+] | Intermediate |
|---|---|---|---|
| 168 | 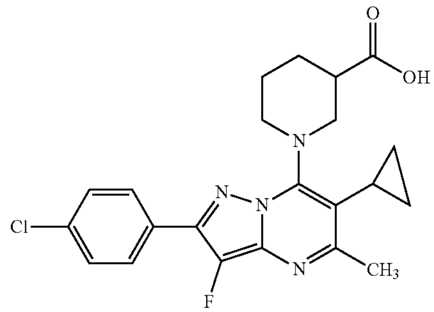 [SMILES: Cc1nc2c(F)c(-c3ccc(Cl)cc3)nn2c(N2CCCC(C(=O)O)C2)c1C1CC1] | 429.2 | 89 |
| 169 | 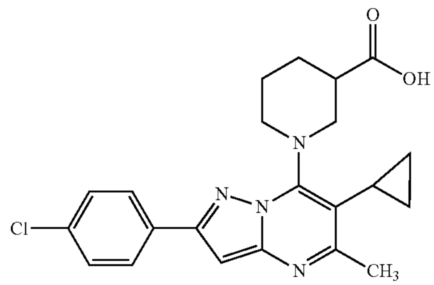 [SMILES: Cc1nc2cc(-c3ccc(Cl)cc3)nn2c(N2CCCC(C(=O)O)C2)c1C1CC1] | 411.1 | 104 |
| 170 | 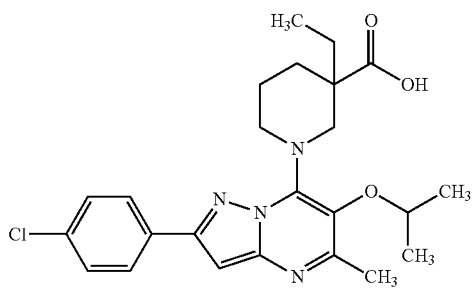 [SMILES: CCC1(C(=O)O)CCCN(c2c(OC(C)C)c(C)nc3cc(-c4ccc(Cl)cc4)nn23)C1] | 457.2 | 87 |

Preparation of Pharmaceutical Compositions

The following formulation examples illustrate representative pharmaceutical compositions of this invention. The present invention however is not limited to the following pharmaceutical compositions.

A) Solid Oral Dosage Forms

| I., Tablets | |
|---|---|
| Active ingredient(s) | 0.01-90% |
| Filler | 1-99.9% |
| Binder | 0-20% |
| Disintegrant | 0-20% |
| Lubricant | 0-10% |
| Other specific excipient(s) | 0-50% |

| II., Orodispersible films | |
|---|---|
| Active ingredient(s) | 0.01-90% |
| Film forming agent | 1-99.9% |
| Plasticizer | 0-40% |
| Other specific excipient(s) | 0-50% |

B) Liquid Oral Dosage Forms

| III., Oral suspensions | |
|---|---|
| Active ingredient(s) | 0.01-50% |
| Liquid vehicle | 10-99.9% |
| Wetting agent | 0-50% |
| Thickener | 0-50% |
| Buffering agent | q.s. |
| Osmotic agent | 0-50% |
| Preservatives | q.s. |

| IV., Syrups | |
|---|---|
| Active ingredient(s) | 0.01-50% |
| Solvent | 10-99.9% |
| Sugar component | 1-20% |
| Flavouring agents | 0-10% |

C) Parenteral Dosage Forms

| V., Intravenous injections | |
|---|---|
| Active ingredient(s) | 0.01-50% |
| Solvent | 10-99.9% |
| Co-solvent | 0-99.9% |
| Osmotic agent | 0-50% |
| Buffering agent | q.s. |

D) Other Dosage Forms

| VI., Suppositories | |
|---|---|
| Active ingredient(s) | 0.01-50% |
| Suppository base | 1-99.9% |
| Surface-active agents | 0-20% |
| Lubricants | 0-20% |
| Preservatives | q.s. |

| VII., Eye drops | |
|---|---|
| Active ingredient(s) | 0.01-50% |
| Water | 0-99.9% |
| Solvent | 0-99.9% |
| Osmotic agent | 0-20% |
| Viscosity enhancer | 0-20% |
| Buffering agent | q.s. |
| Preservatives | q.s. |

The invention claimed is:

1. A compound of formula (I):

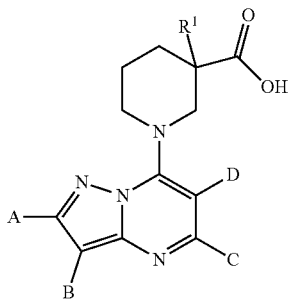

wherein
A is an optionally substituted phenyl or pyridyl group;
B is hydrogen or halogen atom, methyl, cyano group;
C is $C_{1-6}$alkyl,
D is $C_{1-6}$alkyl optionally substituted by a halogen atom or halogen atoms, $C_{3-5}$ cycloalkyl; $C_{3-5}$ cycloalkyl$C_{1-6}$alkyl, dialkylamino, $C_{1-6}$alkoxy, $C_{1-6}$alkoxy$C_{1-6}$alkyl, $C_{1-6}$alkylthio group, tetrahydrofuranyl, tetrahydrofuranyl$C_{1-6}$alkyl, tetrahydropyranyl, tetrahydropyranyl$C_{1-6}$alkyl; or C and D together form a 3 to 7-membered saturated ring, wherein the members of the ring are selected from the group consisting of carbon, nitrogen, oxygen, and sulphur, and wherein the 3 to 7-membered saturated ring is unsubstituted or substituted by one or more of $C_{1-3}$alkyl, $C_{1-3}$alkoxy, halo$C_{1-3}$alkyl, and $C_{1-3}$alkylcarbonyl; and
$R^1$ is hydrogen, halogen atom, $C_{1-6}$ alkyl, hydroxyl, $C_{1-6}$ alkoxy, $C_{1-6}$ alkoxy$C_{1-6}$ alkyl, halo$C_{1-6}$alkyl, or an amino group;

or pharmaceutically acceptable salts, pro-drugs, racemates, enantiomers, diastereomers, thereof.

2. A compound according to claim 1 wherein C is $C_{1-6}$alkyl; and D is $C_{1-6}$ alkyl optionally substituted by a halogen atom or halogen atoms, $C_{3-5}$cycloalkyl, $C_{3-5}$ cycloalkyl$C_{1-6}$alkyl, dialkylamino, $C_{1-6}$alkoxy, $C_{1-6}$alkoxy $C_{1-6}$alkyl, or $C_{1-6}$alkylthio groups.

3. A compound according to claim 1 wherein C and D together form a 3 to 7-membered saturated ring, wherein the members of the ring are selected from the group consisting of carbon, nitrogen, oxygen, and sulphur, and wherein the 3 to 7-membered saturated ring is unsubstituted or substituted by one or more of $C_{1-3}$alkyl, $C_{1-3}$alkoxy, halo$C_{1-3}$alkyl, and $C_{1-3}$ alkylcarbonyl.

4. A compound according to claim 1 wherein C is methyl; and D is isopropyl or $C_{1-6}$alkoxy$C_{1-6}$alkyl.

5. A compound according to claim 1 selected from the group of
(3S)-1-[2-(4-Chlorophenyl)-5-methyl-6-(propan-2-yl)pyrazolo[1,5-a]pyrimidin-7-yl]-3-ethylpiperidine-3-carboxylic acid;
(3S)-3-Ethyl-1-{2-[2-fluoro-4-(trifluoromethyl)phenyl]-5-methyl-6-(propan-2-yl)pyrazolo[1,5-a]pyrimidin-7-yl}piperidine-3-carboxylic acid;
(3R)-3-Ethyl-1-{2-[2-fluoro-4-(trifluoromethyl)phenyl]-5-methyl-6-(propan-2-yl)pyrazolo[1,5-a]pyrimidin-7-yl}piperidine-3-carboxylic acid;
(3S)-1-[2-(4-Chlorophenyl)-5-methyl-6-(propan-2-yl)pyrazolo[1,5-a]pyrimidin-7-yl]-3-(propan-2-yl)piperidine-3-carboxylic acid;
(3S)-1-[5-Methyl-6-(propan-2-yl)-2-[4-(trifluoromethyl)phenyl]pyrazolo[1,5-a]pyrimidin-7-yl]-3-(propan-2-yl)piperidine-3-carboxylic acid;
(3R)-1-{2-[2-Fluoro-4-(trifluoromethyl)phenyl]-5-methyl-6-(propan-2-yl)pyrazolo[1,5-a]pyrimidin-7-yl}-3-(propan-2-yl)piperidine-3-carboxylic acid;
(3S)-3-Methyl-1[5-methyl-6-(propan-2-yl)-2-[4-(trifluoromethyl)phenyl]pyrazolo[1,5-a]pyrimidin-7-yl]piperidine-3-carboxylic acid;
(3S)-1-{2-[2-Chloro-4-(trifluoromethyl)phenyl]-5-methyl-6-(propan-2-yl)pyrazolo[1,5-a]pyrimidin-7-yl}-3-methylpiperidine-3-carboxylic acid;
(3S)-3-Ethyl-1-{2-[3-fluoro-4-(trifluoromethyl)phenyl]-5-methyl-6-(propan-2-yl)pyrazolo[1,5-a]pyrimidin-7-yl}piperidine-3-carboxylic acid;
(3S)-3-Ethyl-1[3-fluoro-5-methyl-6-(propan-2-yl)-2-[4-(trifluoromethyl)phenyl]pyrazolo[1,5-a]pyrimidin-7-yl]piperidine-3-carboxylic acid;
(3R)-1-[2-(4-chlorophenyl)-5-methyl-6-(propan-2-yl)pyrazolo[1,5-a]pyrimidin-7-yl]-3-ethylpiperidine-3-carboxylic acid;
(3R)-1-[2-(4-chlorophenyl)-5-methyl-6-(propan-2-yl)pyrazolo[1,5-a]pyrimidin-7-yl]-3-(propan-2-yl)piperidine-3-carboxylic acid;
(3R)-1-[5-methyl-6-(propan-2-yl)-2-[4-(trifluoromethyl)phenyl]pyrazolo[1,5-a]pyrimidin-7-yl]-3-(propan-2-yl)piperidine-3-carboxylic acid;
(3S)-1-[2-(2,4-dichlorophenyl)-5-methyl-6-(propan-2-yl)pyrazolo[1,5-a]pyrimidin-7-yl]-3-(propan-2-yl)piperidine-3-carboxylic acid;
(3R)-1-{2-[3-fluoro-4-(trifluoromethyl)phenyl]-5-methyl-6-(propan-2-yl)pyrazolo[1,5-a]pyrimidin-7-yl}-3-(propan-2-yl)piperidine-3-carboxylic acid; and
(3S)-1-[3-fluoro-5-methyl-6-(propan-2-yl)-2-[4-(trifluoromethyl)phenyl]pyrazolo[1,5-a]pyrimidin-7-yl]-3-methylpiperidine-3-carboxylic acid.

6. A pharmaceutical composition comprising a therapeutically effective amount of a compound of formula (I) according to claim 1 and a pharmaceutically acceptable carrier.

7. A combination comprising a therapeutically effective amount of a compound of formula (I) according to claim 1 and one or more therapeutically active co-agents.

8. A process for manufacturing a pharmaceutical composition having $GABA_B$ receptor positive allosteric modulator effect comprising mixing a therapeutically effective amount of a compound of formula (I) according to claim 1 and carriers.

9. A compound according to claim 5 selected from the group consisting of:
- (3S)-1-[2-(4-Chlorophenyl)-5-methyl-6-(propan-2-yl) pyrazolo[1,5-a]pyrimidin-7-yl]-3-ethylpiperidine-3-carboxylic acid; and
- (3S)-3-Ethyl-1-{2-[2-fluoro-4-(trifluoromethyl)phenyl]-5-methyl-6-(propan-2-yl)pyrazolo[1,5-a]pyrimidin-7-yl}piperidine-3-carboxylic acid.

10. A compound according to claim 5 selected from the group consisting of:
- (3R)-3-Ethyl-1-{2-[2-fluoro-4-(trifluoromethyl)phenyl]-5-methyl-6-(propan-2-yl)pyrazolo[1,5-a]pyrimidin-7-yl}piperidine-3-carboxylic acid; and
- (3S)-1-[2-(4-Chlorophenyl)-5-methyl-6-(propan-2-yl) pyrazolo[1,5-a]pyrimidin-7-yl]-3-(propan-2-yl)piperidine-3-carboxylic acid.

11. A compound according to claim 5 selected from the group consisting of:
- (3S)-1-[5-Methyl-6-(propan-2-yl)-2-[4-(trifluoromethyl) phenyl]pyrazolo[1,5-a]pyrimidin-7-yl]-3-(propan-2-yl)piperidine-3-carboxylic acid; and
- (3R)-1-{2-[2-Fluoro-4-(trifluoromethyl)phenyl]-5-methyl-6-(propan-2-yl)pyrazolo[1,5-a]pyrimidin-7-yl}-3-(propan-2-yl)piperidine-3-carboxylic acid.

12. A compound according to claim 5 selected from the group consisting of:
- (3S)-3-Methyl-1-[5-methyl-6-(propan-2-yl)-2-[4-(trifluoromethyl)phenyl]pyrazolo[1,5-a]pyrimidin-7-yl]piperidine-3-carboxylic acid; and
- (3S)-1-{2-[2-Chloro-4-(trifluoromethyl)phenyl]-5-methyl-6-(propan-2-yl)pyrazolo[1,5-a]pyrimidin-7-yl}-3-methylpiperidine-3-carboxylic acid.

13. A compound according to claim 5 selected from the group consisting of:
- (3S)-3-Ethyl-1-{2-[3-fluoro-4-(trifluoromethyl)phenyl]-5-methyl-6-(propan-2-yl)pyrazolo[1,5-a]pyrimidin-7-yl}piperidine-3-carboxylic acid; and
- (3S)-3-Ethyl-1-[3-fluoro-5-methyl-6-(propan-2-yl)-2-[4-(trifluoromethyl)phenyl]pyrazolo[1,5-a]pyrimidin-7-yl]piperidine-3-carboxylic acid.

14. A compound according to claim 5 selected from the group consisting of:
- (3R)-1-[2-(4-chlorophenyl)-5-methyl-6-(propan-2-yl) pyrazolo[1,5-a]pyrimidin-7-yl]-3-ethylpiperidine-3-carboxylic acid; and
- (3R)-1-[2-(4-chlorophenyl)-5-methyl-6-(propan-2-yl) pyrazolo[1,5-a]pyrimidin-7-yl]-3-(propan-2-yl)piperidine-3-carboxylic acid.

15. A compound according to claim 5 selected from the group consisting of:
- (3R)-1-[5-methyl-6-(propan-2-yl)-2-[4-(trifluoromethyl) phenyl]pyrazolo[1,5-a]pyrimidin-7-yl]-3-(propan-2-yl)piperidine-3-carboxylic acid; and
- (3S)-1-[2-(2,4-dichlorophenyl)-5-methyl-6-(propan-2-yl) pyrazolo[1,5-a]pyrimidin-7-yl]-3-(propan-2-yl)piperidine-3-carboxylic acid.

16. A compound according to claim 5 selected from the group consisting of:
- (3R)-1-{2-[3-fluoro-4-(trifluoromethyl)phenyl]-5-methyl-6-(propan-2-yl)pyrazolo[1,5-a]pyrimidin-7-yl}-3-(propan-2-yl)piperidine-3-carboxylic acid; and
- (3S)-1-[3-fluoro-5-methyl-6-(propan-2-yl)-2-[4-(trifluoromethyl)phenyl]pyrazolo[1,5-a]pyrimidin-7-yl]-3-methylpiperidine-3-carboxylic acid.

* * * * *